(12) United States Patent
Giobbi et al.

(10) Patent No.: US 10,229,294 B1
(45) Date of Patent: Mar. 12, 2019

(54) IMPLEMENTATION OF A PROXIMITY-BASED SYSTEM FOR OBJECT TRACKING AND AUTOMATIC APPLICATION INITIALIZATION

(71) Applicant: Proxense, LLC, Bend, OR (US)

(72) Inventors: John J. Giobbi, Bend, OR (US); Paul DiSalvo, Lake Worth, FL (US)

(73) Assignee: Proxense, LLC, Bend, OR (US)

( * ) Notice: Subject to any disclaimer, the term of this patent is extended or adjusted under 35 U.S.C. 154(b) by 0 days.

(21) Appl. No.: 15/870,582

(22) Filed: Jan. 12, 2018

Related U.S. Application Data

(63) Continuation of application No. 14/484,090, filed on Sep. 11, 2014, now Pat. No. 9,904,816, which is a continuation of application No. 13/401,710, filed on Feb. 21, 2012, now Pat. No. 8,857,716.

(60) Provisional application No. 61/445,035, filed on Feb. 21, 2011.

(51) Int. Cl.
*G06K 7/10* (2006.01)
*G06K 7/01* (2006.01)

(52) U.S. Cl.
CPC ........... *G06K 7/01* (2013.01); *G06K 7/10267* (2013.01); *G06K 7/10356* (2013.01)

(58) Field of Classification Search
CPC .. G06K 7/00; G06K 7/10356; G06K 7/10386; H01Q 1/24
USPC ................ 235/439; 340/5.52–5.53, 5.8–5.83
See application file for complete search history.

(56) References Cited

U.S. PATENT DOCUMENTS

| | | |
|---|---|---|
| 3,739,329 A | 6/1973 | Lester |
| 4,661,821 A | 4/1987 | Smith |
| 5,623,552 A | 4/1997 | Lane |
| 5,886,634 A | 3/1999 | Muhme |
| 5,910,776 A | 6/1999 | Black |
| 6,104,290 A | 8/2000 | Naguleswaran |
| 6,728,397 B2 | 4/2004 | McNeal |
| 6,879,966 B1 | 4/2005 | Lapsley et al. |
| 6,930,643 B2 | 8/2005 | Byrne et al. |
| 7,049,963 B2 | 5/2006 | Waterhouse et al. |
| 7,079,079 B2 | 7/2006 | Jo et al. |
| 7,123,149 B2 | 10/2006 | Nowak et al. |
| 7,231,068 B2 | 6/2007 | Tibor |
| 7,319,395 B2 | 1/2008 | Puzio et al. |
| 7,333,002 B2 | 2/2008 | Bixler et al. |
| 7,336,181 B2 | 2/2008 | Nowak et al. |

(Continued)

*Primary Examiner* — Dameon E Levi
*Assistant Examiner* — Hasan Z Islam
(74) *Attorney, Agent, or Firm* — Patent Law Works LLP

(57) ABSTRACT

Various apparatuses for use in a wireless network are disclosed. A first apparatus comprises two antennae oriented orthogonally, a biosensor capable of reading a user's fingerprint, and a housing comprising a groove for guiding a user's finger, the groove physically separating the antennae, effectively creating a radome for each antenna. A second apparatus comprises a printed circuit board (PCB) a port, a shell enclosing the PCB, and at least one horseshoe gasket, the shell and gasket creating a waterproof seal isolating the port and the external environment from the rest of the PCB. A third apparatus comprising a bracket for attaching a housing to a building material, an aiming annulus for aiming the housing and the housing. Wherein two or more of the bracket, aiming annulus and housing may be joined in order to mount and aim the housing using one or more structures on the components.

20 Claims, 48 Drawing Sheets

(56) References Cited

U.S. PATENT DOCUMENTS

| | | |
|---|---|---|
| 7,336,182 B1 | 2/2008 | Baranowski et al. |
| 7,349,557 B2 | 3/2008 | Tibor |
| 7,361,919 B2 * | 4/2008 | Setlak ............... G06K 9/00013 250/208.1 |
| 7,565,329 B2 | 7/2009 | Lapsley et al. |
| 7,573,382 B2 | 8/2009 | Choubey et al. |
| 7,652,892 B2 | 1/2010 | Shiu et al. |
| 7,764,236 B2 | 7/2010 | Hill et al. |
| 7,943,868 B2 | 5/2011 | Anders et al. |
| 7,961,078 B1 | 6/2011 | Reynolds et al. |
| 8,026,821 B2 | 9/2011 | Reeder et al. |
| 8,081,215 B2 | 12/2011 | Kuo et al. |
| 8,082,160 B2 | 12/2011 | Collins, Jr. et al. |
| 8,089,354 B2 | 1/2012 | Perkins |
| 8,193,923 B2 | 6/2012 | Rork et al. |
| 8,215,552 B1 | 7/2012 | Rembadt |
| 8,248,263 B2 | 8/2012 | Shervey et al. |
| 8,258,942 B1 | 9/2012 | Lanzone et al. |
| 8,325,011 B2 | 12/2012 | Butler et al. |
| 8,390,456 B2 | 3/2013 | Puleston et al. |
| 8,410,906 B1 | 4/2013 | Dacus et al. |
| 8,421,606 B2 | 4/2013 | Collins, Jr. et al. |
| 8,519,823 B2 | 8/2013 | Rinkes |
| 8,558,699 B2 | 10/2013 | Butler et al. |
| 8,678,273 B2 | 3/2014 | McNeal |
| 8,931,698 B2 * | 1/2015 | Ishikawa ............. G07F 19/2055 235/435 |
| 2006/0001525 A1 | 1/2006 | Nitzan et al. |
| 2006/0014430 A1 | 1/2006 | Liang et al. |
| 2006/0290580 A1 | 12/2006 | Noro et al. |
| 2007/0285212 A1 | 12/2007 | Rotzoll |
| 2008/0012767 A1 | 1/2008 | Caliri et al. |
| 2008/0111752 A1 | 5/2008 | Lindackers et al. |
| 2008/0238625 A1 | 10/2008 | Rofougaran et al. |
| 2009/0045916 A1 | 2/2009 | Nitzan et al. |
| 2010/0134257 A1 | 6/2010 | Puleston et al. |
| 2010/0188226 A1 | 7/2010 | Seder et al. |
| 2010/0277286 A1 | 11/2010 | Burkart et al. |
| 2010/0328033 A1 * | 12/2010 | Kamei ................. A61B 8/0875 340/5.82 |
| 2011/0227740 A1 | 9/2011 | Wholtjen |
| 2011/0266348 A1 * | 11/2011 | Denniston, Jr. .... G06K 7/10722 235/454 |
| 2012/0212322 A1 * | 8/2012 | Idsoe ...................... G06F 21/32 340/5.53 |

\* cited by examiner

IMPLEMENTATION OF A PROXIMITY-BASED SYSTEM FOR OBJECT TRACKING AND AUTOMATIC APPLICATION INITIALIZATION

CROSS-REFERENCE TO RELATED APPLICATIONS

This application is a continuation of and claims priority to U.S. application Ser. No. 14/484,090, filed Sep. 11, 2014, titled "Design and Implementation of a Proximity-Based System for Object Tracking and Automatic Application Initialization," which is a continuation of and claims priority to U.S. application Ser. No. 13/401,710, filed Feb. 21, 2012, titled "Design and Implementation of a Proximity-Based System for Object Tracking and Automatic Application Initialization," which claims priority, under 35 U.S.C. § 119, of U.S. Provisional Patent Application No. 61/445,035, filed Feb. 21, 2011 and entitled "ProxAccess and ProxNet Design and Implementation" each of which is incorporated by reference in its entirety.

BACKGROUND

Field of Art

This disclosure generally relates to the field of radio frequency identification (RFID) and electronic authentication, and more specifically, to systems and methods for object tracking and automatic and secure authentication of users.

Description of the Related Art

Optimizing sales transactions, providing secure access to physical and digital assets, uniquely identifying individuals, and generally improving communications and data exchange are challenges faced by many businesses and organizations. Ensuring that these processes are safe, efficient, reliable, and simple is important to companies, merchants, service providers, users, and consumers. Well-known technologies such as user-specific magnetic cards (e.g., credit and debit cards, employee badges), and more recent developments such as contactless cards designed to allow access or authorization when placed near a compatible reader, are examples of attempts to address the need to instill efficiency and integrity in, for example, the general classes of transactions described above.

SUMMARY

According to at least one aspect of one or more embodiments of the present invention, coverage wireless network system utilizes at least one of the following apparatuses. A first apparatus comprises a plurality of antennae wherein at least two of the plurality of antennae are oriented orthogonal to each other, a biosensor and a housing. The biosensor is located between the at least two orthogonal antennae and capable of reading a user's fingerprint. The housing comprises a groove for guiding a user's finger regardless of the finger's dimensions to the biosensor so that the biosensor can read the user's fingerprint and the groove physically separating the two orthogonal antennae and effectively creating a radome for each of the orthogonal antennae.

In some embodiments, the housing further comprises a chamfered the front edge at an end of the groove. The chamfer prevents the user's finger from tipping the apparatus during a finger swipe.

A second apparatus comprising a printed circuit board (PCB) including a plurality of antennae and a port, a shell and at least one horseshoe gasket. At least two of the plurality of antennae oriented orthogonal to each other. The port enables physically connection and communication with another device. The shell comprises two pieces sealed except at the port to enclose the PCB, wherein the seal between the two pieces is waterproof. The at least one horseshoe gasket surrounds the port and creates a waterproof seal isolating the port and the external environment from the rest of the PCB sealed within the shell.

In some embodiments, the port is a USB port. In some embodiments, the two pieces of the shell are plastic. In one such embodiment, the two pieces of the shell are sealed by fusing the plastic where the two pieces interface.

In some embodiments, two horseshoe gaskets are used to create a waterproof seal. In one such embodiment, a first horseshoe gasket is located between the PCB and a first piece of the shell on a first side of the PCB surrounding the port and a second horseshoe gasket is located between the PCB and a second piece of the shell on the second side of the PCB and wherein the first and second horseshoe gaskets are compressed when the two pieces of the shell are sealed thereby isolating the port and the external environment from the rest of the PCB sealed within the shell.

In some embodiments, at least one piece of the shell further comprises structure that contacts the horseshoe gasket and compresses the horseshoe gasket into the PCB. In one such embodiment, the structure is a horseshoe shaped ridge on an internal side of the at least one piece of the shell.

A third apparatus comprises a bracket, an aiming annulus and a housing. The bracket attaches the housing to a building material. The bracket comprises an annular shape and a plurality of structures protrude from the inner circumference of the bracket, the structures having a first shape.

The aiming annulus aims the housing. The aiming annulus comprises an extruded annulus having a first and second annular plane at opposite ends of the aiming annulus, wherein the first annular plane is non-parallel with the second annular plane. The aiming annulus further comprises a plurality of protruding structures from the inner circumference of the aiming annulus the plurality of structures having the first shape, and a plurality of structures extending beyond the first annular plane having a second shape. The structures of the aiming annulus having the second shape are capable of interacting with the structures of the first shape on one or more of the bracket and another aiming annulus in order to join the aiming annulus to one or more of the other aiming annulus and the bracket.

The housing encloses electronics. The housing comprises a first exterior surface comprising structures having the second shape which protrude from the first exterior surface. The structures of the housing having the second shape are capable of interacting with the structures of the first shape on one or more of the bracket and the aiming annulus in order to join the housing to one or more of the aiming annulus and the bracket.

In some embodiments, the bracket further comprises a backing piece and a face plate that are fastened together in order to mount the bracket to the building material. In some embodiments, one or more of the backing piece and the face plate include a structure having a third shape, the third structure limiting the minimum distance between the face plate and the backing piece. In some embodiments, the third shaped structure comprises a plurality of posts.

In some embodiments, the first shaped structure comprises a tooth-like structure and wherein the second shaped structure comprises an upside-down capital "L" shape. In some embodiments, the first and second shaped structures interact to lock two or more of the bracket, aiming annulus and housing together when the two or more components are pressed and twisted together causing the first and second shaped structures to interlock. In some embodiments, the first and second shaped structures interact and join two or more of the bracket, aiming annulus and housing such that two or more joined components cannot rotate relative to each other. In some embodiments, wherein causing the interaction of the first and second shaped structures to join two or more of the housing, the aiming annulus and the bracket can be done without the use of a specialized tool. In some embodiments, causing the interaction of the first and second shaped structures to join two or more of the housing, the aiming annulus and the bracket can be done by hand.

Figure 1:
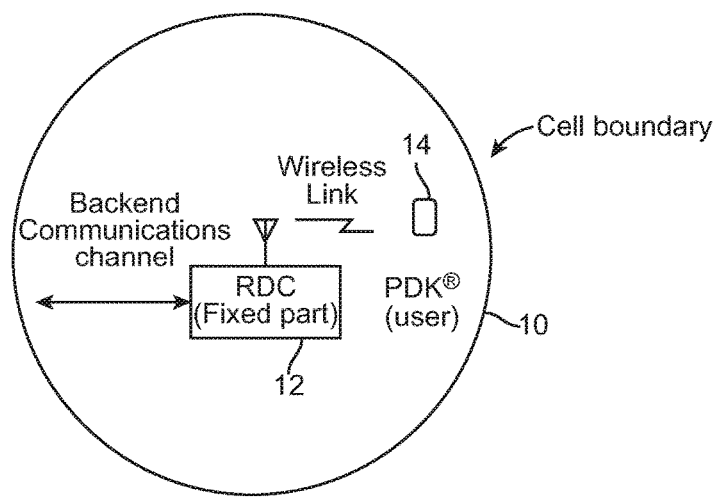
FIG. 1 shows a single wireless cell in which a reader decoder circuit (RDC) and a personal digital key (PDK) are present.

Each of the figures referenced above depict an embodiment of the present invention for purposes of illustration only. Those skilled in the art will readily recognize from the following description that one or more other embodiments of the structures, methods, and systems illustrated herein may be used without departing from the principles of the present invention.

DETAILED DESCRIPTION

In the following description of embodiments of the present invention, numerous specific details are set forth in order to provide a more thorough understanding of the present invention. However, it will be apparent to one skilled in the art that the present invention may be practiced without one or more of these specific details. In other instances, well-known features have not been described in detail to avoid unnecessarily complicating the description.

In general, embodiments of the present invention relate to a technique for synchronizing (or "coordinating") multiple wireless cells, in any one of which an individual (or "user") can reliably and securely conduct one or more wireless transactions with some device in one or more of the cells. Particularly, in one or more embodiments, wireless cells are synchronized in order to prevent wireless collisions and extend the battery life of individual user units.

At perhaps a most basic level, one or more embodiments includes a personal digital key ("PDK") and a reader decoder circuit ("RDC"). In general, a PDK is a portable wireless device that may be conveniently carried by an individual to facilitate wireless tracking and/or allow the individual to wirelessly access various applications, assets, and/or services. As further described in detail below with reference to FIGS. 5-7, a PDK may be any device that (i) may be worn, placed in a pocket, wallet, or purse of a user, or attached to equipment, (ii) has a bi-directional wireless communications transceiver, and (iii) stores public and/or secret electronic identification numbers, as possibly some set of cryptographic keys. The form factor of the PDK is not limiting, so long as the PDK may be portably, and preferably conveniently and seamlessly, carried by an individual. For example, a PDK may be in the form of a "key fob" or a card, or in certain embodiments, a PDF may actually be integrated with or implemented in another device, such as a watch or mobile computing device (e.g., cellular phone, personal digital assistant (PDA)).

An RDC, as used in one or more embodiments, is a device that can wirelessly interact with a PDK to link the PDK user with various applications, assets, and/or services. The RDC may be a fixed access point serving as a gatekeeper for a PDK requesting access to a particular system. An RDC may be used in various settings and/or applications. For example, an RDC may be physically incorporated into a casino floor itself, an electronic game, a doorway, a pedestrian traffic monitoring point, a personal computer application, an e-commerce device (e.g., an automatic teller machine (ATM)), or any other application requiring a secure transaction or access control.

Further, secure data exchange for various financial and/or retail applications may be facilitated through use of a PDK and RDC in accordance with one or more embodiments. For example, a purchasing system may be implemented whereby a consumer can purchase goods or services using his/her personal "key" (e.g., a PDK) based on the key being in detectable wireless proximity of a reader device (e.g., an RDC). The purchase transaction may then be carried out based on some data exchange between the key and the reader device, where the key stores accessible, and possibly encrypted or encoded, information about the consumer (e.g., name, address, phone number, bank account information, biometric information, credit or debit card information). The validation or authentication of the consumer may occur either on the key itself and/or by the reader device. In the case of "on-key" validation, for example, the reader device may pass some information about the consumer (e.g., a biometric input, such as fingerprint data) to the key, which then matches the data provided by the reader device with permanently stored secure data about the consumer.

Various other applications or uses involving any number of PDK and RDC devices are possible in accordance with one or more embodiments. Accordingly, while examples of scenarios and applications are described herein for purposes of illustration and clarity, the present invention is not limited to any particular application, scenario, setting, or use.

Single Cell Operation of the RDC and PDK

Now referring to FIG. 1, it shows a single cell 10 in which, at some point in time, an RDC 12 and a PDK 14 are present. The RDC 12 may be some fixed device that has a cell radius defined by its wireless coverage boundary. When an individual carrying the PDK 14 comes into proximity of the RDC 12 by entering a coverage area of the RDC 12, a wireless communications session is initiated between the PDK 14 and the RDC 12. If the RDC 12 determines that the PDK 14 is authorized to communicate, information between the PDK 14 and the RDC 12 may be securely exchanged. Information securely obtained from the user's PDK 14 may then be used locally or sent through a back-end communications channel to a central server (not shown). When the transaction completes or when the PDK 14 leaves the coverage area of the RDC 12, wireless communication between the RDC 12 and the PDK 14 ceases. Thereafter, the RDC 12 may remain idle (i.e., be in a "tracking" mode) until a PDK again enters the cell 10.

Unsynchronized Multi-Cell Operation of Multiple RDCs and PDKs

Figure 2:
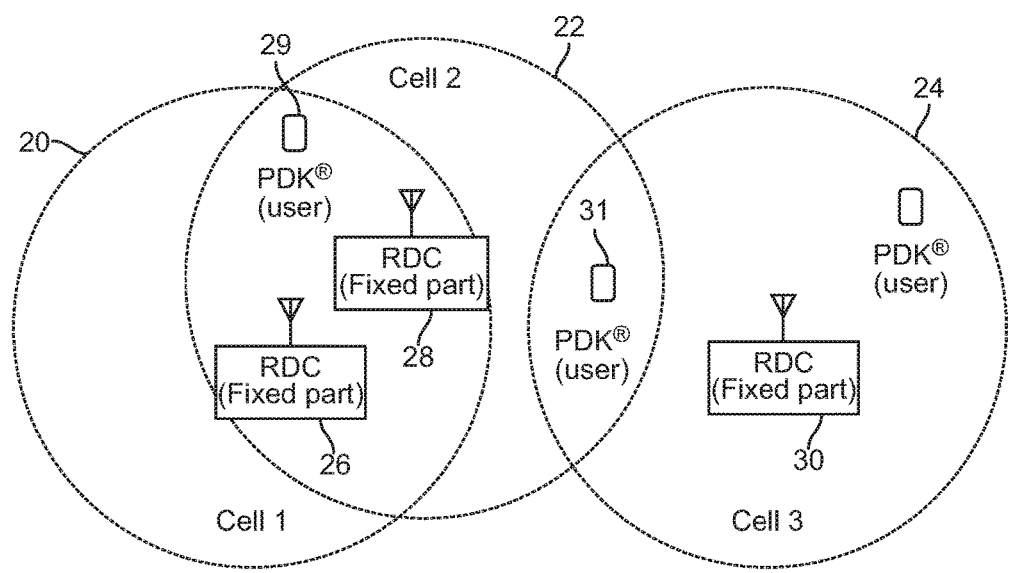
FIG. 2 shows partially overlapping RDC cells.

Now referring to FIG. 2, in certain implementations, multiple RDC cells 20, 22, 24 may exist in an area. The RDCs in the multiple cells 20, 22, 24 may or may not be aware of each other, but are able to interact with one or more PDKs. The PDKs, in turn, are capable of interacting with the RDCs. As shown in FIG. 2, there are three partially overlapping RDC cells 20, 22, 24. An RDC 26, 28, 30 in cells 20, 22, 24, respectively, is independent and may not be in association with the other RDCs. Although the cells 20, 22, 24 partially overlap, each RDC 26, 28, 30 is capable of wirelessly communicating with any PDK 29, 31 within its cell boundary.

In one or more embodiments, the RDC 26, 28, 30 is capable of determining if energy is present on any given wireless channel. The RDC 26, 28, 30 may then determine the best channel to operate on and continue to place an identification marker (or "beacon") out for any PDK 29, 31 that enters its cell boundary.

The PDK 29, 31 itself may be responsible for locating an RDC 26, 28, 30 by searching through available wireless channels, communicating with an RDC 26, 28, 30, and notifying the RDC 26, 28, 30 of its presence. In an implementation where two RDCs can communicate with one another (e.g., RDCs 26, 28 in cells 20, 22 shown in FIG. 2), the RDCs may select different communication frequencies. However, in the case where cells overlap, but each RDC cannot directly communicate with one another (e.g., RDCs 28, 30 in cells 22, 24 shown in FIG. 2), any PDK intending to access an RDC, may have to alert the RDC of possible collisions on the wireless channel on which the RDC is operating.

Synchronized Multi-Cell Operation of Multiple RDCs and PDKs

In certain implementations, multiple RDCs may be placed to allow an overlap of cells between each adjacent RDC within a confined area. This permits each RDC to be aware of its surrounding RDCs, thereby allowing synchronization of each RDC to the other. For example, now referring to FIG. 3, there are shown three partially overlapping RDC cells 40, 42, 44 with RDCs 46, 48, 50. The cell 40, 42, 44 of each respective RDC 46, 48, 50 overlaps the cell of the adjacent RDC 46, 48, 50. In such a manner, each RDC 46, 48, 50 may initiate wireless communication with an adjacent RDC 46, 48, 50. This begins a negotiation process among the RDCs 46, 48, 50 to determine which RDC 46, 48, 50 should be the coordinator and on what channel to communicate.

Figure 3:
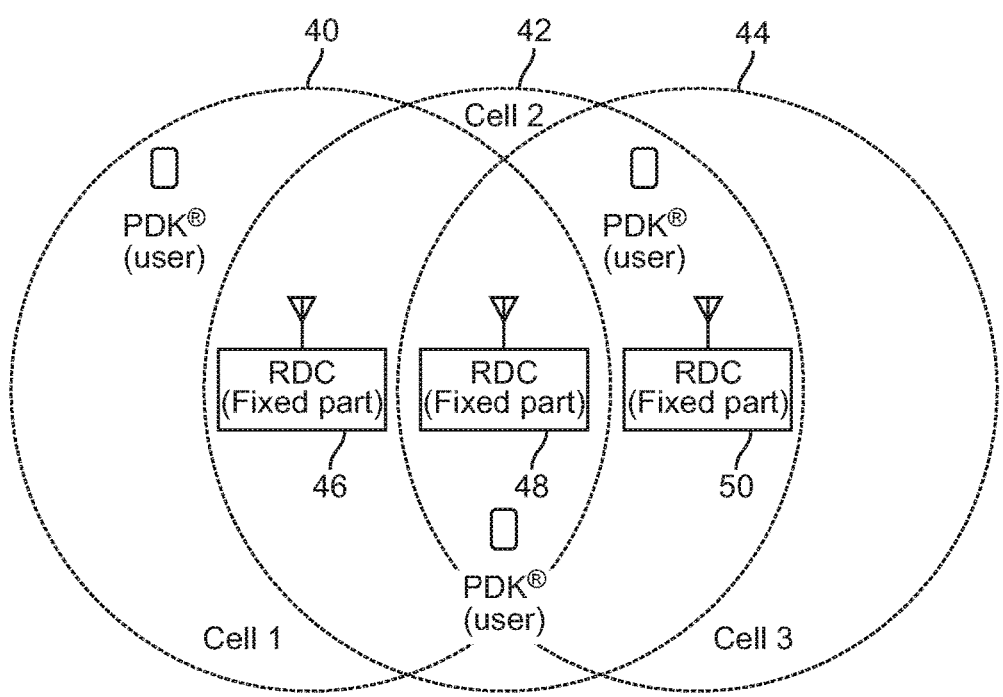
FIG. 3 shows synchronized partially overlapping RDC cells.

Although any of the RDCs 46, 48, 50 may be the coordinator, in the example shown in FIG. 3, RDC 48 in cell 42 may be a favorable candidate. Its selection permits ubiquitous coverage of the RDCs 46, 48, 50 shown in FIG. 3, additionally providing multiple transactions and timing alignment through a "daisy chain" whereby RDC 46 synchronizes RDC 48 and RDC 48 synchronizes RDC 50.

Still referring to FIG. 3, each RDC 46, 48, 50 may also share frequency and timeslot information among each other and with one or more PDKs. It is noted that if a PDK is located at an edge of, for example, cell 40, that PDK may still monitor the other channels that adjacent RDCs 48, 50 are operating on, but may not have access to these RDCs. Thus, in a configuration such as that shown in FIG. 3, a PDK may be forced to consume more energy due to the monitoring of multiple channels. Further, it is noted that as cell density increases, more collisions may begin occurring and/or active communication times may increase.

Coordinated Multi-Cell Operation

Figure 4:
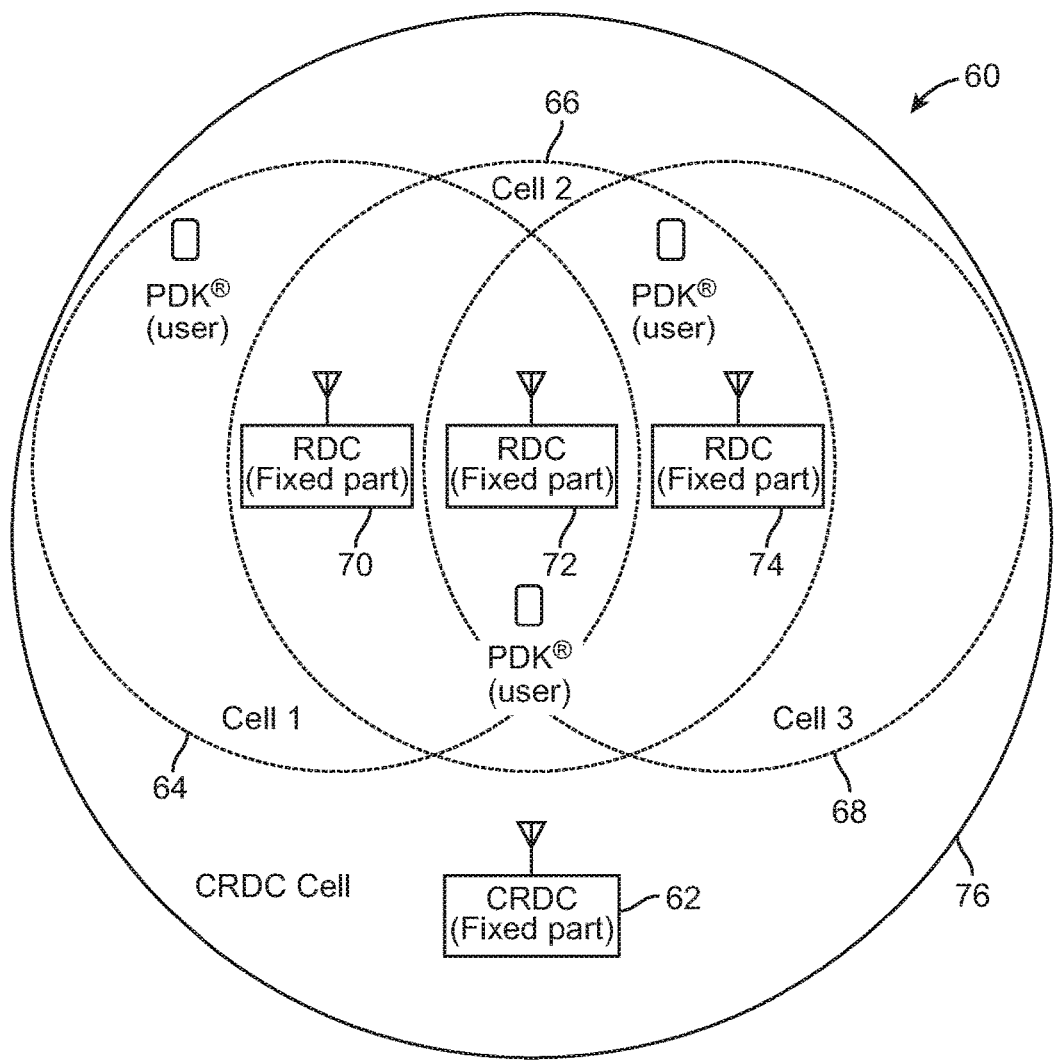
FIG. 4 shows a synchronized multi-cell system in accordance with one or more embodiments of the present invention.

Now referring to FIG. 4, it shows an exemplar synchronized (or "coordinated") multi-cell system 60 in accordance with one or more embodiments. As will be apparent from the description below, a synchronized multi-cell system may provide ubiquitous PDK and RDC synchronization as well as PDK battery conservation within the system 60. Further, in addition to ubiquitous synchronization, channel and frequency capacity may both be coordinated, thereby reducing collisions while increasing system throughput.

Turning now to FIG. 4 particularly, a coordinator RDC ("CRDC") 62 has ubiquitous coverage of a plurality of cells 64, 66, 68 in the system 60. In one or more embodiments, the CRDC 62 provides beacon transmissions, which can be used to synchronize a plurality of devices within the coverage area 76 of the CRDC 62. In other words, by providing wide-area coverage, a plurality of devices, both RDCs 70, 72, 74 and PDKs (shown, but not labeled in FIG. 4), in the coverage area 76 are able to monitor a wireless transmission beacon broadcast by the CRDC 62 and determine how and when to communicate in a coordinated manner. Further, in one or more embodiments, the CRDC 62 may broadcast additional information including, but not limited to, a beacon transmission rate, framing information, channel information, system identification, and/or cluster identification. Moreover, it is noted that although the CRDC 62 may provide timing and certain system related information, RDCs 70, 72, 74 and PDKs may still communicate among themselves.

As described above with reference to FIGS. 1-4, there are at least three different types of devices (or software entities) that may be used, for example, in a synchronized multi-cell system, such as that shown in FIG. 4. A PDK is a trackable device having secure electronic keys and that may be portably carried by a user. An RDC is a device that acts as a gatekeeper controlling access of a PDK to a particular system. A CRDC is a device that is used to synchronize one or more RDCs and PDKs within a particular geographic area formed of either a single cell or multiple cells. A more detailed description of each of these components is now provided below.

PDK

Figure 5:
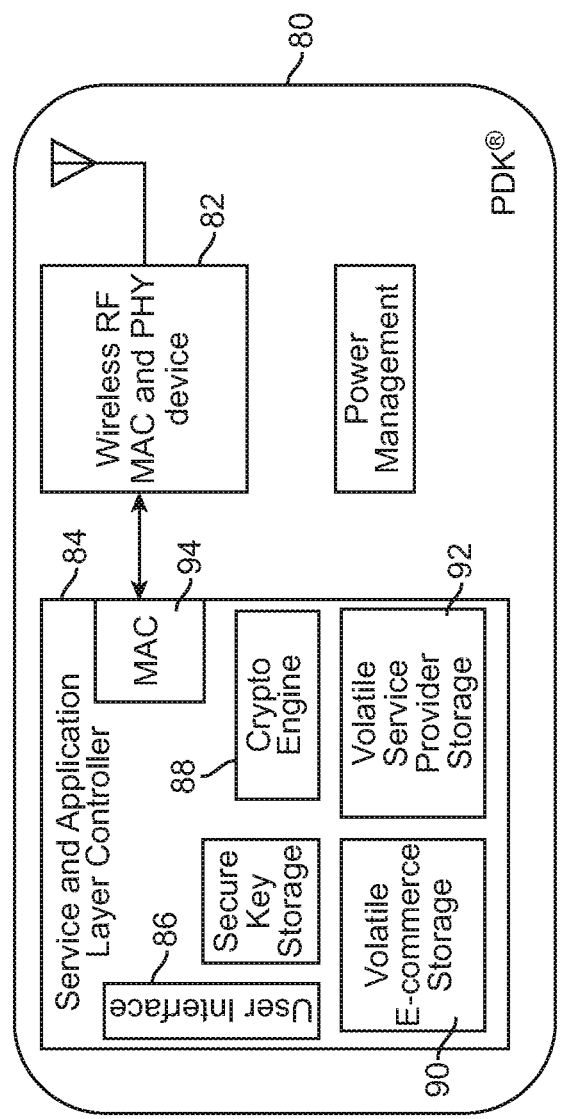
FIG. 5 shows a PDK in accordance with one or more embodiments of the present invention.

Now referring to FIG. 5, it shows an example PDK 80 in accordance with one or more embodiments. Based on a specific application or use of the PDK 80, the PDK 80 may have different configurations for interacting with the PDK user. For example, the PDK 80 may have no user input mechanism or display, may have a single button input mechanism, may have a multi-button input mechanism, may have a biometric input mechanism, and/or may have an interactive user input mechanism and/or display.

As shown in FIG. 5, the PDK 80 has a wireless radio frequency (RF) media access control (MAC) and physical layer device 82 that facilitates bi-directional communications with external wireless RF devices, such as an RDC (not shown). In one or more embodiments, the wireless RF MAC and physical layer device 82 may communicate according to an IEEE 802.15.4 protocol. However, in one or more other embodiments, the PDK 80 may be capable of communicating according to one or more different wireless protocols.

The PDK 80 also has a service and application layer controller 84 that includes a MAC portion 94 that serves as an interface with the wireless RF MAC and physical layer device 82. Further, the service and application layer controller 84 also includes portions that provide specific functions used to protect electronic keys and services of the PDK 80. Further still, the service and application layer controller 84 may support an optional user interface 86, which if implemented, allows user interaction with the PDK 80. A cryptography engine 88 may also be resident on the PDK 80.

Figure 6:
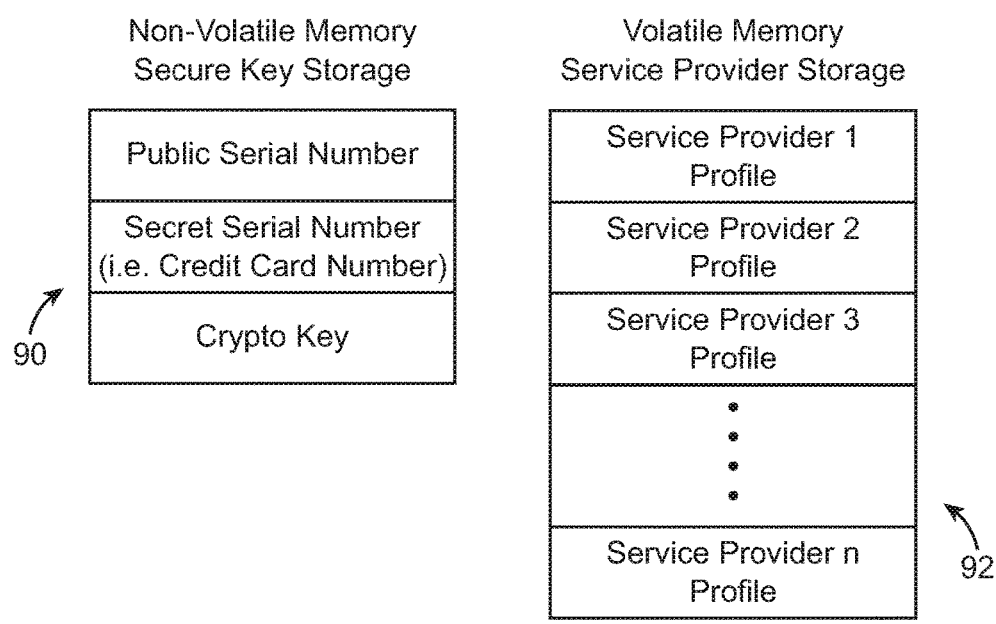
FIG. 6 shows a portion of the PDK shown in FIG. 5.

Now also referring to FIG. 6, it shows a non-volatile memory storage 90 and a volatile memory storage 92 of the PDK 80. These two devices 90, 92 are related to security storage. In one or more embodiments, these devices 90, 92 may be accessible by an RDC (not shown) having the appropriate security algorithms and by private service providers having the correct security information. However, in one or more other embodiments, certain secured data may not be wirelessly communicated at all, in which case, validation or authorization occurs on the PDK 80 itself.

Specifically as to the non-volatile memory storage 90, a public serial number may be used to identify the PDK 80 and allow secure look-up of a secure serial number and a cryptography key via a remote server (not shown). The secure serial number may be thought of as being equivalent to, for example, encoded user identification information stored in a magnetic strip of a credit card, whereby such information is not visible to the outside world. The cryptography key may be used to allow decoding of the secure serial number from, for example, an RDC (not shown).

Further, it is noted that in one or more embodiments, the non-volatile memory storage 90 and associated parameter lengths may be dynamically assigned, with overall constraints depending on, for example, available memory in the PDK 80.

Now, specifically as to the volatile memory storage 92, this area may be used for security and may allow a service provider to store a profile containing secret keys and other secure information, such as privilege information. A service provider identification value may be stored to allow the service provider to easily identify the user. In addition, a service provider service identification value may be stored and used to allow that service provider to access that information. The PDK 80 validates that service provider identification value via the service provider secret key before allowing access to that service provider's profile area in the PDK 80. Further, as shown in FIG. 6, the volatile memory storage 92 may have a number of service provider profiles.

Figure 7:
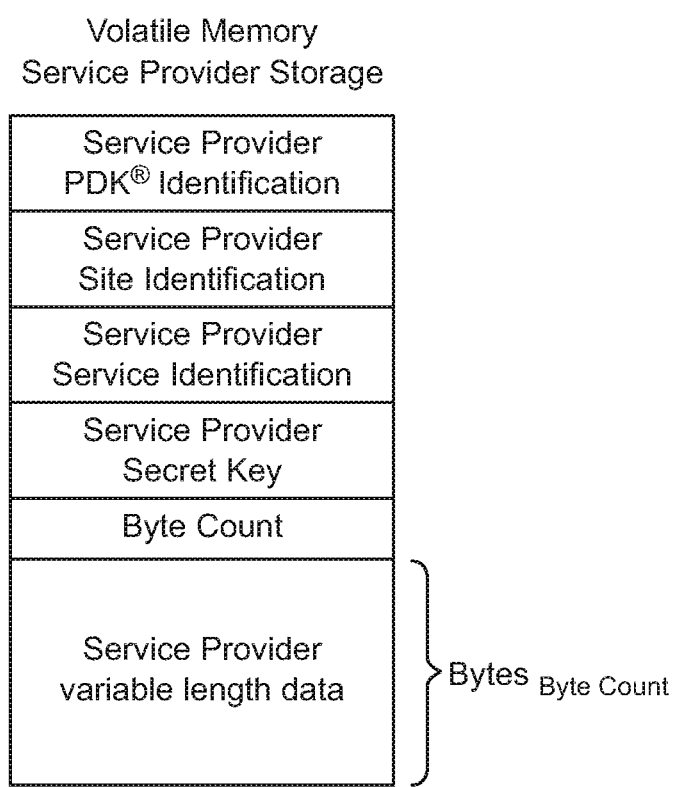
FIG. 7 shows a portion of the PDK shown in FIG. 5.

Now also referring to FIG. 7, the service provider profile area may be of a variable length and allow a service provider the flexibility to store various parameters. The length may be determined by a byte count following the service provider's secret key in the memory area as shown in FIG. 7.

RDC

Next, turning to a more detailed description of an RDC 100 according to one or more embodiments, reference is made below to FIGS. 8 and 9. In general, an RDC 100, as described above, may be fixed and used to allow a PDK access into a particular system (e.g., gaming/casino system, financial institution, retail system). The RDC 100 may have different configurations to support different types of secure transactions. Some examples of applications and uses of RDCs include, but are not limited to, casino slot machines and gaming consoles, secure entryway control, user/equipment location tracking, personal computers and components thereof (e.g., disk drives), financial institution interactions, and retail purchasing. In the case of a personal computer, or any computer system for that matter, a reader device, such as an RDC, may be used to control access to certain data stored in the computer system. Thus, in such embodiments, an RDC 100 may be thought of as providing a form of digital content management.

In certain cases, the RDC 100 effectively acts as a gatekeeper allowing authorized individuals access to specific information or transactions. In other cases, because an RDC 100 may use proximity detection for determining if a PDK is within a particular geographical area, the RDC 100 may also be used for tracking one or more PDKs within a given area or network. In still other cases, an RDC 100 may be used for both location tracking and secure transaction purposes.

Figure 8:
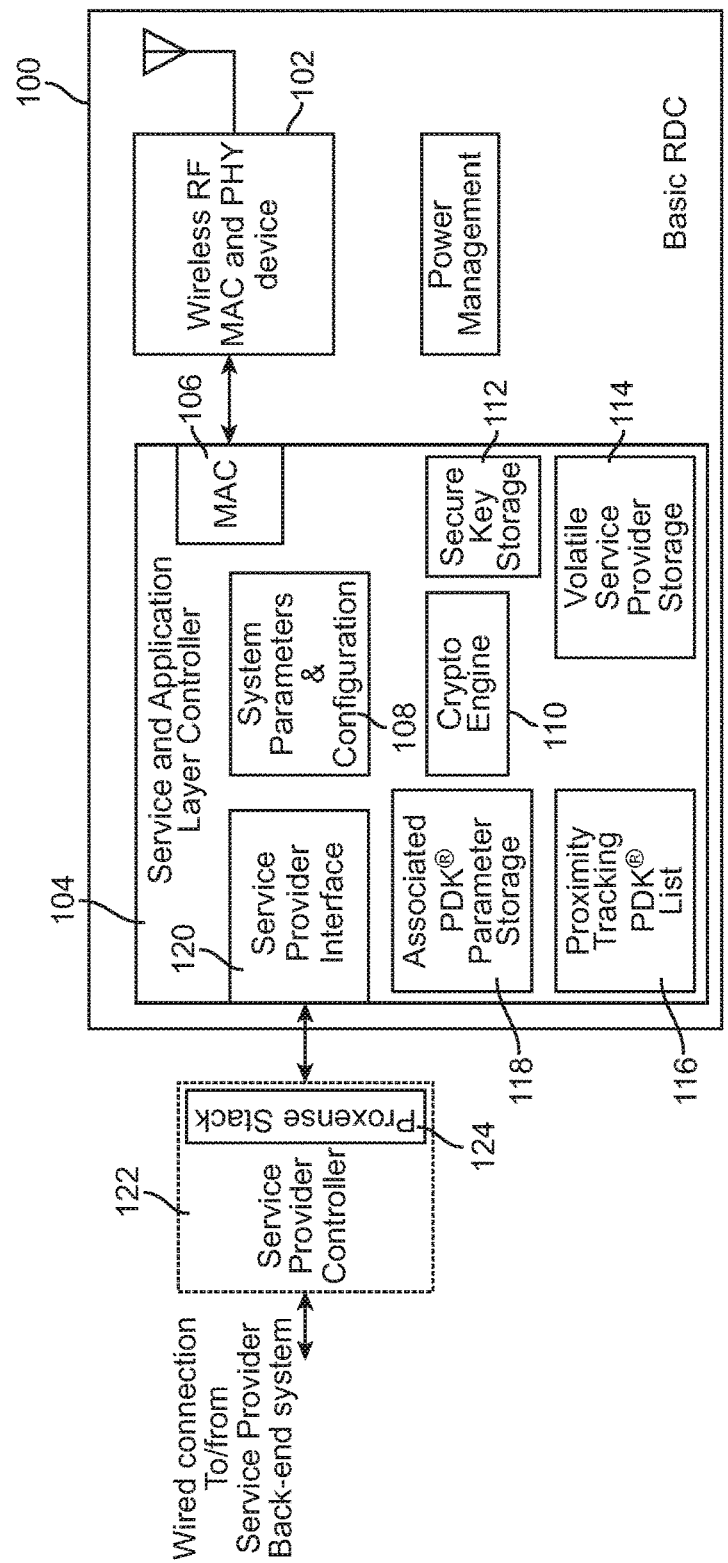
FIG. 8 shows an RDC in accordance with one or more embodiments of the present invention.

FIG. 8 shows a type of RDC 100 that uses a single wireless RF MAC and physical layer device 102. In RDC 100, communications are passed through the single wireless RF MAC and physical layer device 102. The single wireless RF MAC and physical layer device 102 facilitates bi-directional communication with one or more external RF wireless devices, such as a PDK (not shown). Thus, the single wireless RF MAC and physical layer device 102 may communicate with both PDKs according to assigned time slots (further described below) and one or more CRDCs (described in further detail below). Further, it is noted that in one or more embodiments, the single wireless RF MAC and physical layer device 102 may wirelessly communicate according to an IEEE 802.15.4 protocol. However, in one or more other embodiments, the RDC 100 may be capable of communicating according to one or more different wireless protocols.

The RDC 100 also has a service and application layer controller 104. The service and application layer controller 104 has a MAC portion 106 specific to a wireless protocol of the RDC 100. The service and application layer controller 104 may further provide functions related to associating and tracking PDKs (not shown), as well as providing information back to a service provider.

The service and application layer controller 104 includes system parameters and configuration information 108 that may be used to identify the RDC 100 and define how the RDC 100 operates within a given environment. Further, the system parameters and configuration information 108 may define how the RF link is time slotted and/or how RF frequencies are used in the system. In one or more embodiments, these values may be optimized to reduce power consumption within one or more PDKs (not shown).

Still referring to the RDC 100 shown in FIG. 8, a cryptography engine 110 may also be present. One or more of various storage elements may also exist in the service and application layer controller 104. A secure key storage area 112 may be programmed to define public, secret, and/or cryptography keys for the RDC 100.

Further, in one or more embodiments, the service and application layer controller 104 may have additional memory areas, one or more of which may dynamically change dependent on system changes and wireless PDK connections. A volatile service provider storage 114 may allow a service provider to store semi-static information related to a specific PDK (not shown) or group of PDKs (not shown) for real-time access for those devices. An example might relate to a hotel room door lock. With a hotel room door, service provider information related to a PDK may be stored in the RDC. When a user comes within proximity of the door, the door could unlock. Thus, in this example, the RDC is not required to interface with a back-end server in real-time, thereby reducing bandwidth consumption to the back-end server, while allowing the user immediate access. Moreover, in one or more embodiments, the RDC may have a connection to a network or other infrastructure for receiving control signals as to which PDKs should be allowed to unlock the door.

The service and application layer controller 104 may also have a proximity tracking PDK list 116 that includes PDK identity information, signal quality metrics, and/or time stamps for each PDK (not shown) that is in proximity of the RDC 100. Such information may be used in the RDC 100 to perform an operation and/or may be relayed to a back-end server when, for example, location tracking is desired.

Still referring to FIG. 8, the service and application layer controller 104 may also have an associated PDK parameter storage 118. The associated PDK parameter storage 118 may contain a list of one or more PDKs (not shown) actively performing transactions with the RDC 100. It is noted that in one or more embodiments, although such transactions are performed with the RDC 100, the actual processing result of the RDC 100 to/from PDK transaction may be passed to a back-end server for further processing.

A service provider interface 120 may allow both control and query of the RDC 100. The service provider interface

120 may further provide the transport for keys from a PDK (not shown). In one or more embodiments, the service provider interface 120 may use a universal asynchronous transmitter receiver (UART) interface and may allow some level of control and status of the RDC 100.

An external service provider controller 122 may be attached to the service provider interface 120 with a system stack 124 residing in the external service provider controller 122. The system stack 124 may allow a third party to easily interface with the RDC 100, possibly requiring function calls to the system stack 124. Further, the external service provider controller 122 may provide translation of data. It is still further noted that the external service provider controller 122 and the RDC 100 may reside on the same physical component (e.g., circuit board).

Figure 9:
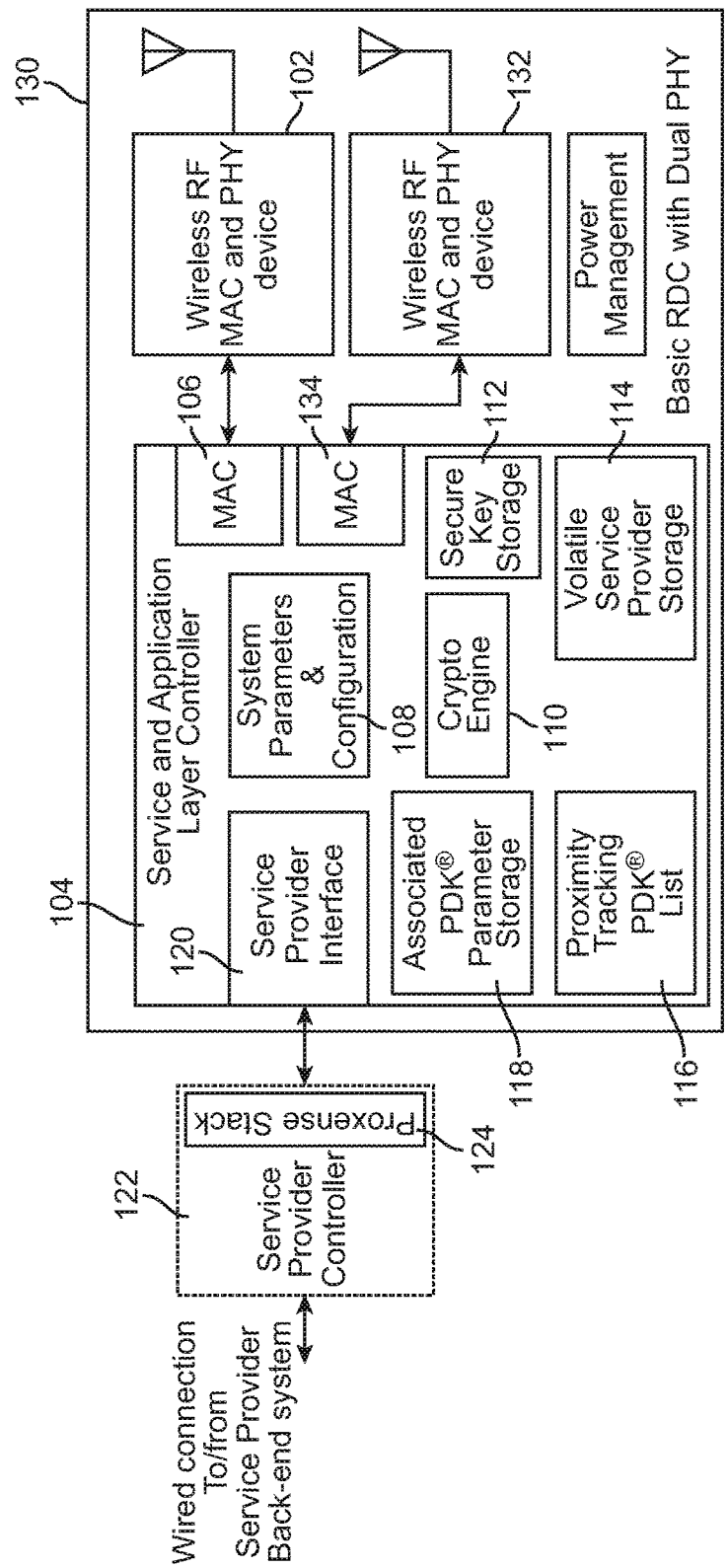
FIG. 9 shows an RDC in accordance with one or more embodiments of the present invention.

Now referring to FIG. 9, it shows another type of RDC 130, which has an additional wireless RF MAC and physical layer device 132. In this configuration, components having like reference numbers as those reference numbers in FIG. 8 function identically or similarly to the corresponding components in FIG. 8. The additional wireless RF MAC and physical layer device 132 may be used to maintain synchronization with a CRDC (not shown) and pass networking related information, while the other wireless RF MAC and physical layer device 102 may be used to communicate with one or more PDKs (not shown) within a cell of the RDC 130. Further, the service and application layer controller 104 may have an additional MAC portion 134 to interface with the additional wireless RF MAC and physical layer device 132.

Still referring to the RDC 130, the use of dual wireless transceivers 102, 132 may allow for increased throughput and efficient use of the RF spectrum available to the system. Thus, in other words, these multiple wireless links allow simultaneous reception of data from client devices (e.g., PDKs) and of CRDC timing information on separate channels, thereby eliminating the need for back-channel synchronization of the network. Further, the multiple wireless links may allow for the simultaneous proximity sensing of multiple client devices (e.g., PDKs) in a "tracking" mode, along with the association of a client device with one particular cell for wireless application (e.g., secure transaction) purposes. For example, an RDC serving as a wireless player tracking device on a casino floor may, while keeping track of multiple transient players entering and leaving the zone of coverage of that particular tracking device, invite a particular player to begin a gaming session. This session may also include the exchange of player information with, for example, both the game and its back-end server to allow credit for games played and money spent. In another scenario, the system may facilitate another entire suite of applications, such as, for example, unlocking a hotel room door, while simultaneously keeping track of unrelated client devices coming and going within its coverage range.

CRDC

Next, turning to a more detailed description of a CRDC according to one or more embodiments, a CRDC may, for example, be an RDC of either of the types described above with reference to FIGS. 8 and 9. At least one difference, however, between a CRDC and an RDC is that the CRDC has increased RF power output, or more generally, casts a broader range of wireless coverage. Another difference is that, in one or more embodiments, a CRDC may not communicate bi-directionally with a PDK, whereas an RDC of the types described above with reference to FIGS. 8 and 9 may. Moreover, a CRDC may be capable of communicating with another CRDC, and may also be capable of communicating with an RDC. It is noted that CRDC-CRDC communication may allow for frame synchronization and frequency planning without requiring a wired connection between the CRDCs. The same may be true for CRDC-RDC communications. In certain implementations, it may occur that CRDC cell boundaries do not overlap, and thus, the corresponding CRDCs may not be able to directly communicate with another. In this case, an RDC that is between the cells may communicate with both CRDCs and act as a communication bridge to pass frequency and other control information in an effort to coordinate the system.

Still describing the general application and use of a CRDC in accordance with one or more embodiments, the CRDC may serve as a stand-alone wireless beacon that may be used to coordinate the timing and activities of individual, physically separated wireless providers (e.g., RDCs) with defined coverage areas, along with their clients (e.g., PDKs) in an autonomous, wireless proximity sensing and data transfer network. A CRDC may also be used to propagate system-wide information (e.g., periodic changes in cryptographic keys), thereby relieving traffic otherwise loading a wired back-end network linking individual cells to the back-end system. Thus, the CRDC may act as a system-wide master clock across multiple cells that may not be close enough to synchronize with each other directly without a wired connection.

Wireless Protocol

Figure 10:
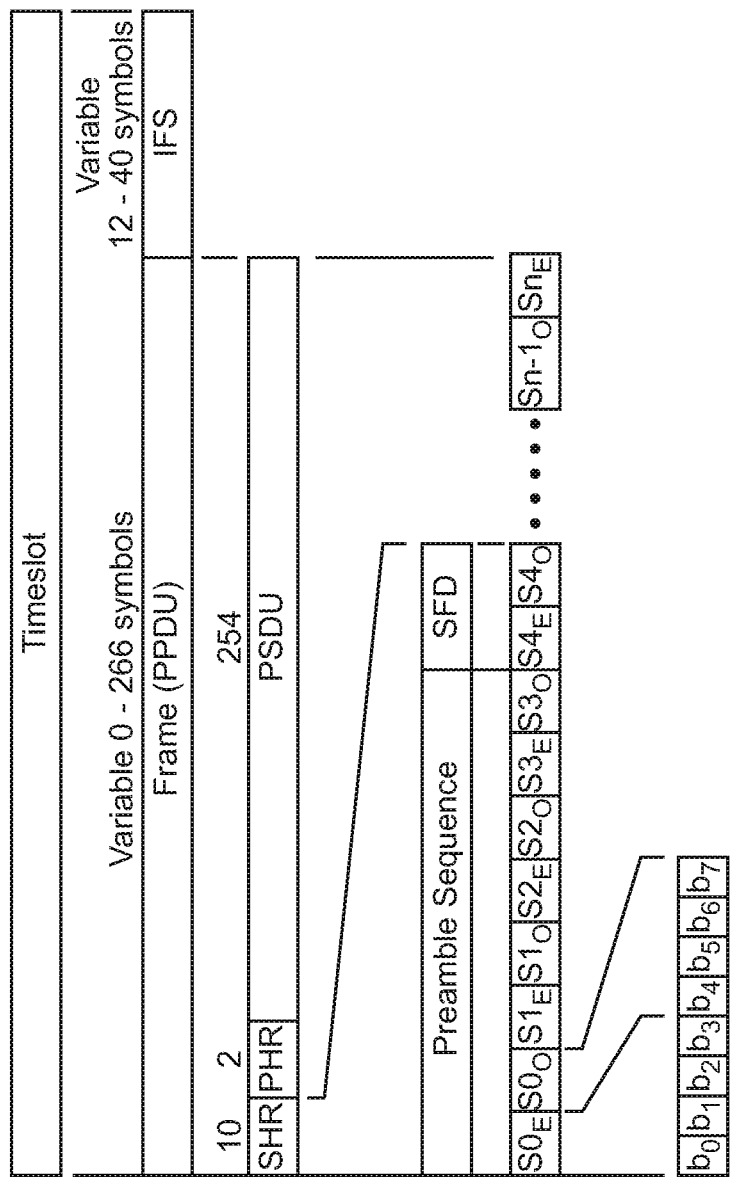
FIG. 10 shows an arrangement of a timeslot in accordance with one or more embodiments of the present invention.

As described above, a system in accordance with one or more embodiments may rely, or at least partly be based, on an IEEE 802.15.4 protocol. In relation to a protocol usable in one or more embodiments, a "timeslot" is defined as a period of time that information is communicated between two devices. FIG. 10 shows an example of portions of a timeslot in accordance with one or more embodiments. The timeslot is divided into a frame (or physical packet data unit (PPDU)) and inter-frame spacing (IFS). The frame includes synchronization information and carries the payload of data. The IFS allows time for a receiving end unit to process the data in the frame and transmitter turn-around time. Both the PPDU and the IFS may be variable in length as determined by an amount of data carried in the frame.

The frame is broken down into a sync header (SHR), a physical header (PHR), and a physical service data unit (PSDU). The SHR may contain a preamble sequence and start-of-frame delimiter (SFD) that allows a receiving device to acquire the RF signal and synchronize to the frame. The PSDU may then be used to carry both 802.15.4 MAC and user data information. Further, it is noted that the PSDU may be of a variable length that is determined by the type of MAC and data information being carried.

Still referring to FIG. 10, the frame may be further divided into symbols, which, in turn, are divided into bits. In one or more embodiments, each symbol may include 4 bits that are sent least significant bit to most significant bit at the base band level.

Figure 11:
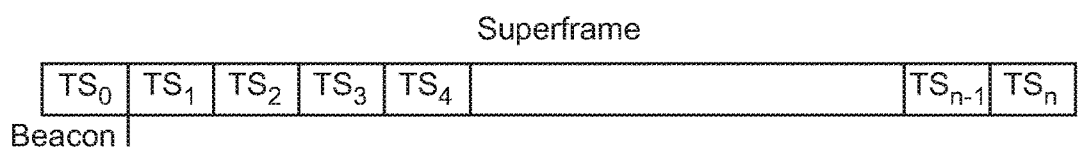
FIG. 11 shows a superframe in accordance with one or more embodiments of the present invention.

Now referring to FIG. 11, a "superframe" is formed of multiple timeslots. The superframe may be used in a beacon-enabled synchronous network where PDKs can find an RDC and/or CRDC fixed device. The superframe may allow a PDK to efficiently determine if an RDC is present on any given frequency.

The superframe may be configured such that timeslot 0 ($TS_0$) is the "beacon timeslot." Each superframe that is transmitted may start with a beacon timeslot. Further, each timeslot may be equally spaced so that a PDK and RDC can communicate.

Further, it is noted that in one or more embodiments, a superframe may be of a variable length dependent on the resolution to a timeslot. The initial number of timeslots within a superframe may be, for example, 16; but, in one or more other embodiments, a superframe may have a different number of timeslots.

Figure 12:
FIG. 12 shows a coordinator superframe in accordance with one or more embodiments of the present invention.

Now referring to FIG. 12, a "coordinator superframe" (c-superframe) may be formed of multiple superframes. In one or more embodiments, a c-superframe may be generated by a CRDC. A c-superframe may provide one or more advantages over a superframe. For example, a c-superframe may provide better battery management for a PDK, as well as provide distributed superframe and timeslots in a high density networking environment.

As shown in FIG. 12, a c-superframe may have multiple superframes. Because each superframe may have a beacon, as described above with reference to FIG. 11, multiple beacons may be transmitted per c-superframe. This may allow a PDK to quickly determine if it is within a system. A c-superframe may also number the superframes, so that both an RDC and a PDK can realize their position within the framing structure.

Figure 13:
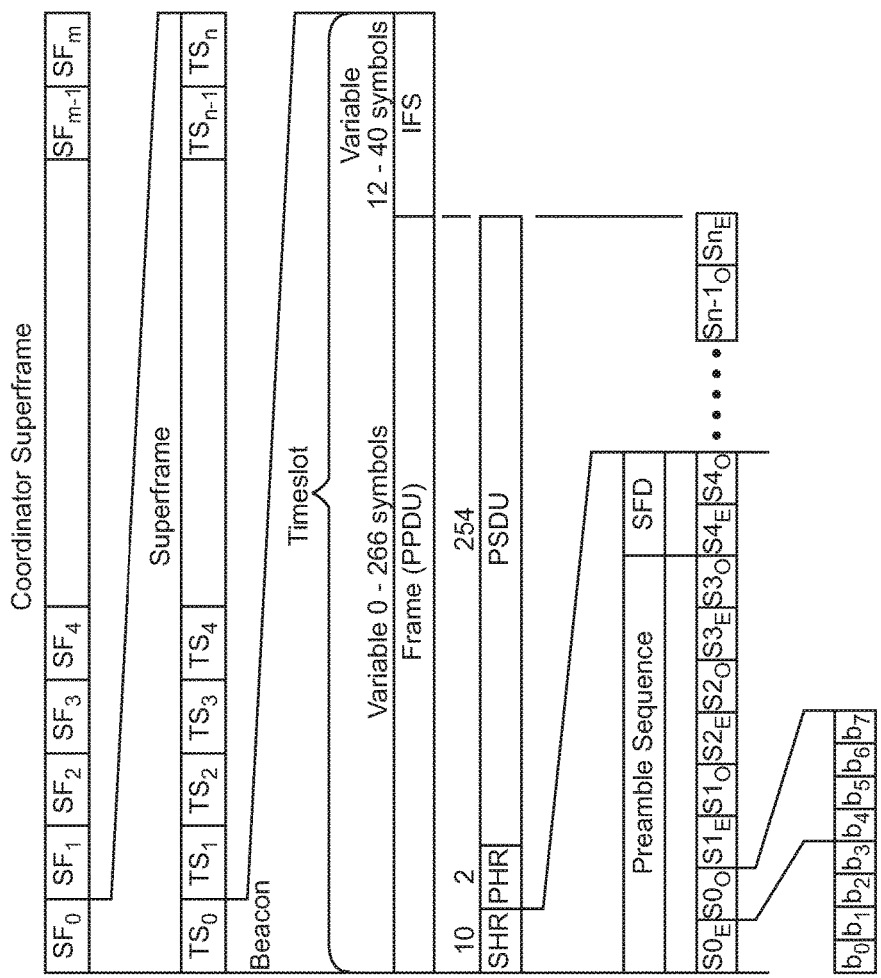
FIG. 13 shows an overall framing structure in accordance with one or more embodiments of the present invention.

FIG. 13 shows an overall framing structure of a timeslot as described above with reference to FIG. 10, a superframe as described above with reference to FIG. 11, and a c-superframe as described above with reference to FIG. 12.

Beacons

As discussed above with reference to FIG. 11, a beacon may be sent in every superframe. The beacon is used to alert PDKs (and RDCs when a CRDC is present) of system information and timing of the framing structure employed. In one or more embodiments, such a configuration may be implemented using an IEEE 802.15.4 protocol. However, in one or more other embodiments, communication may occur according to one or more different wireless protocols.

In a single cell configuration in which one RDC is present (shown, for example, in FIG. 1), the beacon may be transmitted in timeslot 0 of a superframe boundary. By transmitting the beacon periodically, a PDK may wake up and find the beacon within a short period of time and realize that it is within some particular network.

In an unsynchronized multi-cell configuration in which multiple RDCs are geographically located near each other, but no synchronization between RDCs is implemented (shown, for example, in FIG. 2), a PDK may still wake up, detect the presence of the RDCs, and synchronize and communicate with each RDC due to the presence of the beacon on each RDC.

In a high density area in which multiple RDCs are present, a CRDC may most likely be present. In such a configuration, the CRDC may transmit the beacon, and all RDCs and PDKs in the coverage area of the CRDC align to the CRDC beacon. The CRDC may send a beacon on each superframe, as well as a c-superframe and other configuration information to the RDCs and PDKs.

Figure 14:
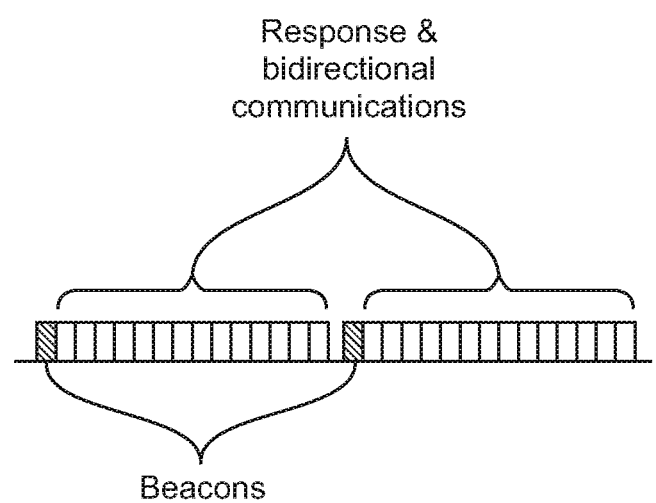
FIG. 14 shows an RDC beacon for use in a single cell system in accordance with one or more embodiments of the present invention.

Now referring to FIG. 14, in a single cell configuration (shown, for example, in FIG. 1), a beacon is periodically output based on a specific number of timeslots. Further, in one or more embodiments, the beacon may be used in accordance an IEEE 802.15.4 protocol, with additional data attached indicating it is an RDC. At the end of each superframe, there may exist an additional idle period that allows tolerance in an over-the-air protocol.

After a beacon is transmitted, a PDK may immediately respond provided it follows the rules of what is know in the art as "carrier sense multiple access—collision avoidance" (CSMA-CA). If a PDK finds that the channel is busy in the current timeslot, the PDK may back-off and attempt again to access the RDC in another timeslot following the same rules.

In the case the PDK is not able to communicate with the RDC, the PDK may wait for the next beacon and attempt again.

Figure 15:
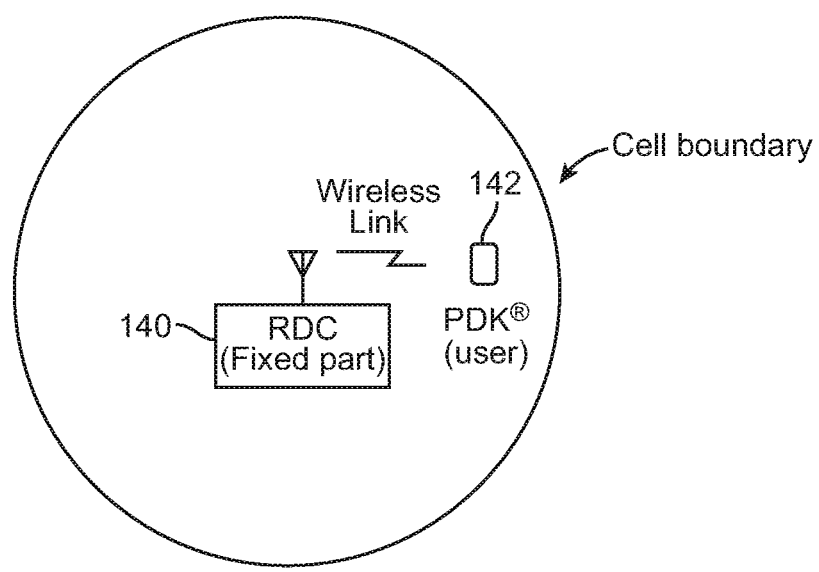
FIG. 15 shows a single cell system in accordance with one or more embodiments of the present invention.

FIG. 15 shows a single cell configuration in accordance with one or more embodiments. As shown in FIG. 15, a single fixed RDC 140 may be connected to a back-end server (not shown). The single cell system shown in FIG. 15 includes, for example: a computing controller with an operating system, an application, a back-end server interface, and a system stack; the RDC 140, which is the gateway for a PDK and performs authorization (the system stack and RDC 140 together allow a user who has a PDK to access the application dependent on authorization from the back-end server); and a PDK 142 that includes necessary security information and is within reasonable proximity to wirelessly communicate with the RDC 140.

Figure 16:
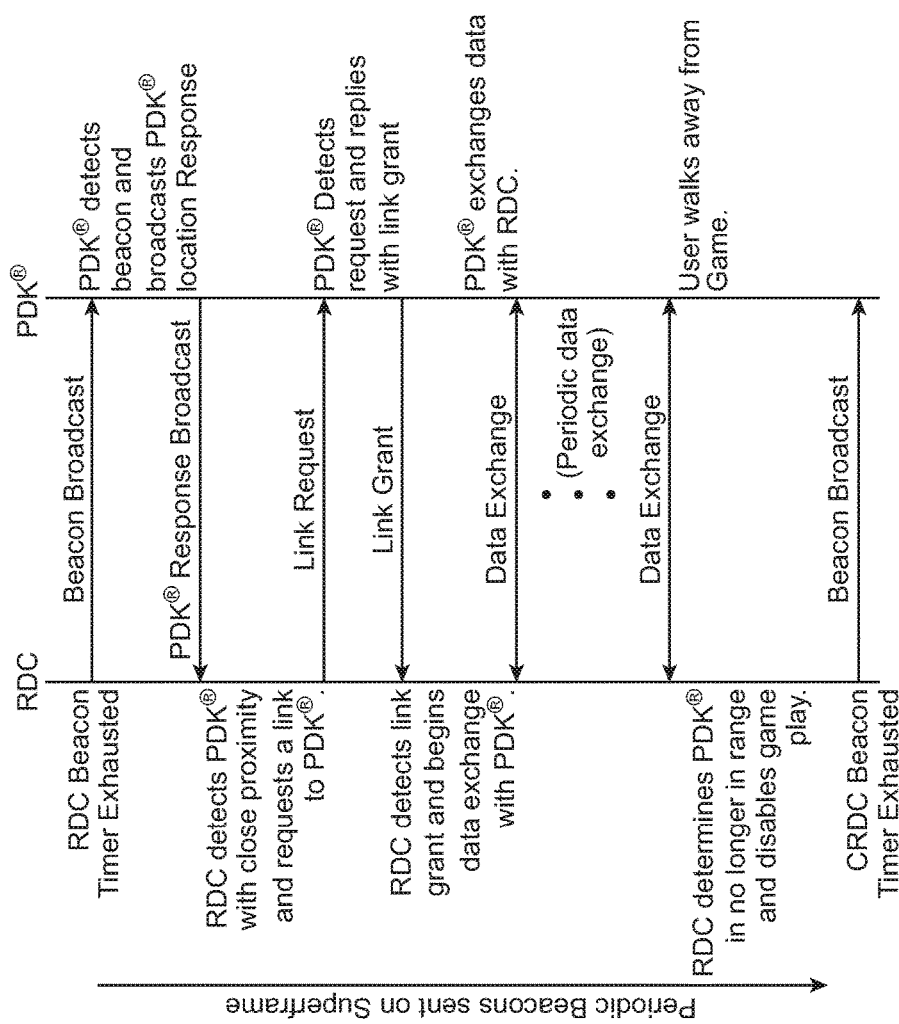
FIG. 16 shows a PDK-RDC handshake in accordance with one or more embodiments of the present invention.

An example handshake of the PDK 142 with the RDC 140 is shown in FIG. 16. The RDC 140 outputs a periodic beacon based on timeslot 0 of a superframe. Eventually, a user walks within the coverage area of the RDC 140, and the user's PDK 142 detects the beacon from the RDC 140. The PDK 142 determines if it is registered to this RDC 140 (or network), and, if so, responds with a PDK location response. The RDC 140 then detects the PDK location response and performs a link request to the PDK 142. The PDK 142 then accepts the request by replying with a link grant, and the two devices 140, 142 are now in data exchange mode. In data exchange mode, the two devices 140, 142 may transfer specific security information that result in the RDC 140 enabling access to the system through the system stack, computing controller, and/or back-end central server.

Periodically, data may be exchanged between the RDC 140 and the PDK 142 to ensure that the PDK 142 is still within close proximity of the RDC 140. As long as data exchange continues on a periodic basis, the application may remain enabled and the user can continue to access the application.

After some amount of time, the user walks away from the RDC 140 causing the data exchange to cease, in which case, the system stack indicates to the computing controller that the PDK 142 is out of range. The computing controller then disables the application to prevent unauthorized access. Regardless of data exchange, the RDC 140 may continue to transmit periodic beacons to guarantee that other PDKs may gain access to the application.

Figure 17:
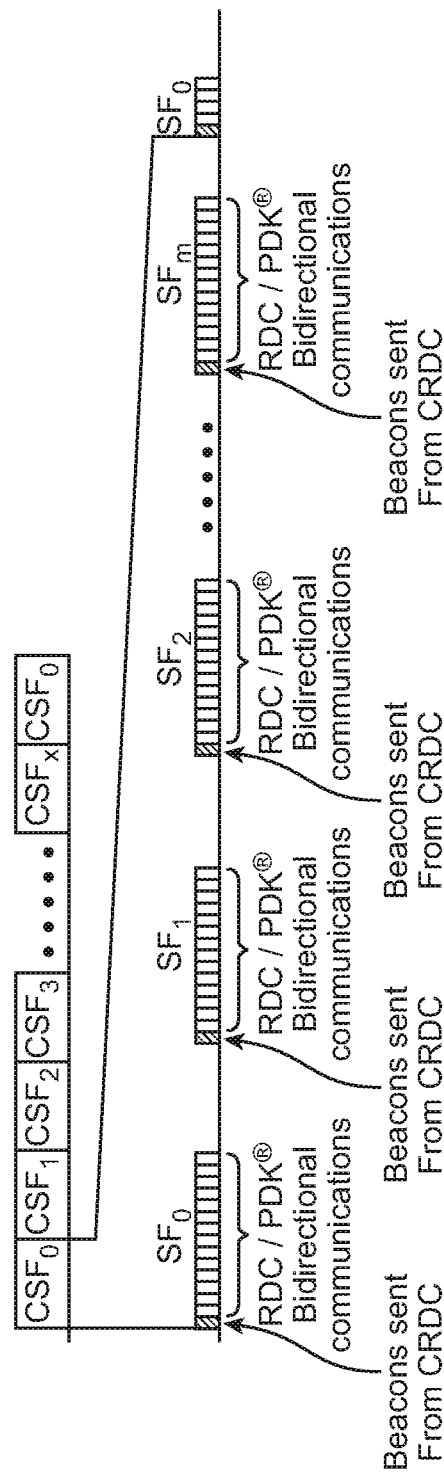
FIG. 17 shows a coordinator beacon configuration in accordance with one or more embodiments of the present invention.

Now referring to FIG. 17, a configuration of a "coordinator beacon" (c-beacon) is shown. The coordinator beacon may be generated by a CRDC, or RDC behaving like a CRDC. As described above, a CRDC may cover a large geographic area covering a plurality of RDCs and PDKs within that area. The c-beacon may be a standard beacon sent in the first timeslot of each superframe as shown in FIG. 17.

A c-beacon, in accordance with one or more embodiments, may have properties that are different than those associated with an IEEE 802.15.4 standard beacon. For example, the standard c-beacon carries a field indicating the beacon is a c-beacon. Further, a c-beacon, in normal operation, is a unidirectional transmission from a CRDC. Further still, a c-beacon may contain other c-beacon related information: number of slots in a superframe; number of superframes in a c-superframe; the channels on which adjacent CRDCs operate; current superframe number; current c-superframe number; site ID; CRDC ID; PDK superframe mask; and PDK timeslot mask.

Further, it is noted that while beacons may be transmitted from a CRDC on timeslot 0 of each superframe, remaining timeslots of a superframe may be left open for unsynchronized communications between PDKs and RDCs. The term "unsynchronized" is used to describe communications between the PDKs and the RDCs because the RDC and PDK share a common CRDC beacon, but the PDK may not get synchronized directly to an RDC beacon. In this manner, the PDK and RDC may appear to represent a peer-to-peer network.

C-beacon information described above relates to configuration fields that allow the system to operate efficiently when using a CRDC. In the case of, for example, a large scale system, a service provider of the system may have knowledge of RDC coverage relative to the CRDC. The following description provides details of these fields.

A "superframe_len" field may be governed by an IEEE 802.15.4 protocol. The number of slots may be from, for example, 21 to 214. The number of slots in a superframe may be used to define the repetition rate for the beacon.

A "c-superframe_len" field may be used to define a higher layer counter used for extended power savings in a PDK. The c-superframe_len value may also define the number of beacons within a superframe. If the superframe is configured to not have a beacon, then this field may be ignored.

| Name | Type | Valid Range | Description |
| --- | --- | --- | --- |
| C-Superframe_Len | Integer | 0 to 15 | Defines the number of Superframes in a C-Superframe. Number of Superframes is defined as $2^{C\text{-}Superframe\_Len}$ |

A "CRDC_chan_flags" field may be used to indicate to a PDK what channels are used by adjacent CRDCs.

| Name | Type | Bit | Description |
| --- | --- | --- | --- |
| CRDC_Chan_Flags | Binary | | When any bit in this field is set to a 1, an adjacent CRDC is transmitting on that frequency. |
| | Binary | 0 | 1 = Channel 0 available<br>0 = Channel 0 not available |
| | Binary | 1 | 1 = Channel 1 available<br>0 = Channel 1 not available |
| | Binary | 2 | 1 = Channel 2 available<br>0 = Channel 2 not available |
| | Binary | 3 | 1 = Channel 3 available<br>0 = Channel 3 not available |
| | Binary | 4 | 1 = Channel 4 available<br>0 = Channel 4 not available |
| | Binary | 5 | 1 = Channel 5 available<br>0 = Channel 5 not available |
| | Binary | 6 | 1 = Channel 6 available<br>0 = Channel 6 not available |
| | Binary | 7 | 1 = Channel 7 available<br>0 = Channel 7 not available |
| | Binary | 8 | 1 = Channel 8 available<br>0 = Channel 8 not available |
| | Binary | 9 | 1 = Channel 9 available<br>0 = Channel 9 not available |
| | Binary | 10 | 1 = Channel 10 available<br>0 = Channel 10 not available |
| | Binary | 11 | 1 = Channel 11 available<br>0 = Channel 11 not available |
| | Binary | 12 | 1 = Channel 12 available<br>0 = Channel 12 not available |
| | Binary | 13 | 1 = Channel 13 available<br>0 = Channel 13 not available |
| | Binary | 14 | 1 = Channel 14 available<br>0 = Channel 14 not available |
| | Binary | 15 | 1 = Channel 15 available<br>0 = Channel 15 not available |

A "superframe_cnt" field may be used to define a current superframe (or beacon) count within a c-superframe. If the superframe is configured to not have a beacon, then this field may not be transmitted.

| Name | Type | Valid Range | Description |
| --- | --- | --- | --- |
| Superframe_Cnt | Integer | 0 to 65535 | Defines the current Superframe count. |

A "c-superframe_cnt" field may be used to define a current c-superframe count. If the superframe is configured to not have a beacon, then this field may not be transmitted.

| Name | Type | Valid Range | Description |
| --- | --- | --- | --- |
| C-Superframe_Cnt | Integer | 0 to 65535 | Defines the current C-Superframe count. |

A "PDK_sf_ts_msk" field may be used to define the bits of a superframe count and the timeslot count to use for PDK superframe and timeslot sequencing while in a tracking mode. If the superframe is configured to not have a beacon, then this field may not be transmitted.

| Name | Type | Valid Range | Description |
| --- | --- | --- | --- |
| PDK ®_SF_TS_Msk | | | Defines which bits are to be used for determining PDK ® superframes and timeslots to communicate with an RDC during location tracking. |
| Superframe Mask | Binary | 0000000000000 to 1111111111111 | Defines the Superframe mask<br>1 = enable bit<br>0 = mask bit |
| Timeslot Mask | Binary | 000 to 111 | Defines the Timeslot mask<br>1 = enable bit<br>0 = mask bit |

Figure 18:
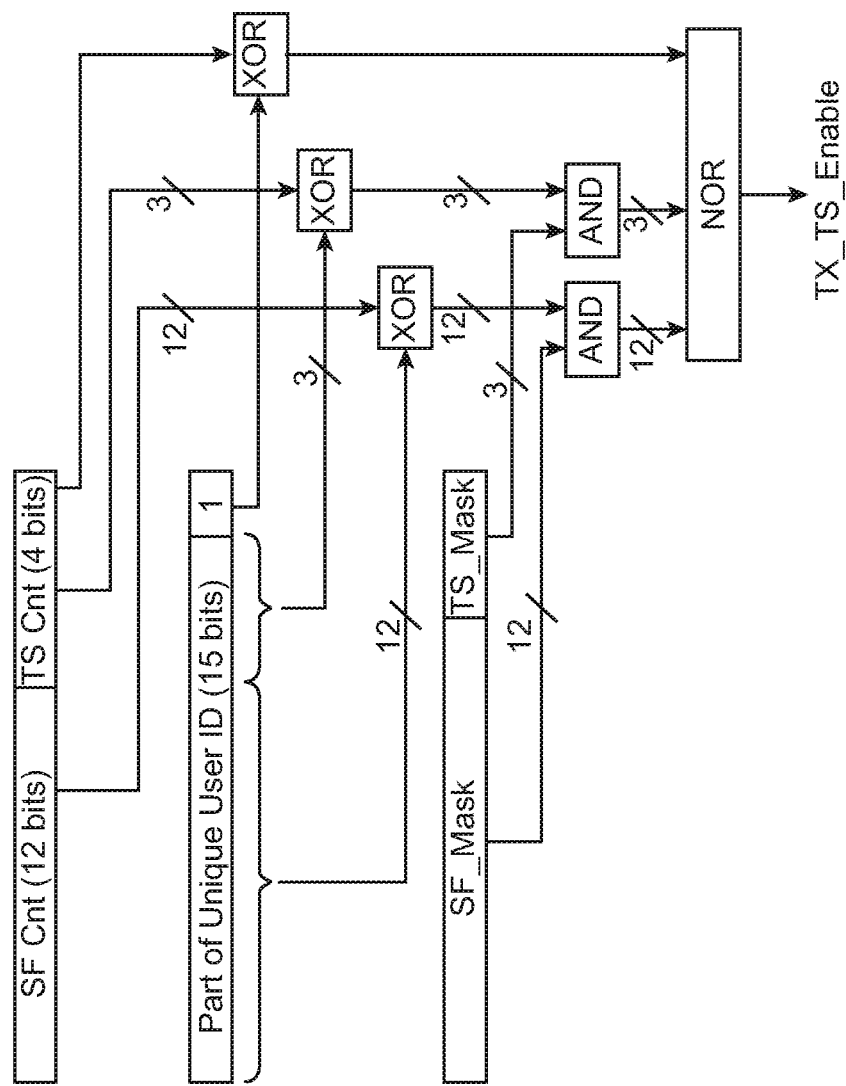
FIG. 18 shows a PDK transmit timeslot enable operation in accordance with one or more embodiments of the present invention.

The PDK_sf_ts_msk value may be used in conjunction with a portion of the service provider unique PDK identification value and may be used to determine the exact superframe and timeslot the PDK is permitted to transmit a location identifier back to the RDCs. The necessary logic and variables required to perform this operation are illustrated in FIG. 18.

Further, in one or more embodiments, to set the mask value of a particular PDK, a "set_pdk_msk_val" function may be used. The mask may be used over the superframe and timeslot counts and service provider's PDK ID to determine the superframe and timeslot the PDK is active on in the framing structure. In other words, the set_pdk_msk_val function may be used to set a mask for the PDK in an effort to establish at what times the PDK can communicate with an RDC. The function may return a pass or fail indication to indicate whether the mask has been successfully set. Conversely, to obtain the mask value being used by a particular PDK, a "get_pdk_msk_val" function may be used to retrieve the current PDK superframe and timeslot mask parameters.

Using, for example, the masking approach described above, individual client devices (e.g., PDKs) within a given cell (e.g., an RDC's wireless coverage area) may be addressed via real-time re-provisioning on command. Thus, in other words, by reserving time slots for both client device transmission and reception (based on masks established by the network), client transmission and reception time slots may be efficiently coordinated to reduce collision likelihood and allow for tiered client access, assignment of specific classes, and/or targeting an individual user for preferential, non-contended system access. Further, in one or more embodiments, bit masks may be changed to include or exclude specific users (or classes of users). Still further, in one or more embodiments, bit masks may be changed to dynamically alter access to the network by users or classes of users as traffic load on the network changes. Moreover, it is noted that once a specific client exits the network, previously reserved time slots of that client may be reassigned to one or more other client devices in the network.

To provide an example, there may be multiple client devices (e.g., PDKs) in proximity of a particular fixed reader device (e.g., an RDC). Each of these client devices, other than providing a location response, may request some data exchange with the reader device in order carry out a secure transaction. In an effort to reduce collision and coordinate the time slots that each client device "talks" with the reader device, a mask may be communicated to each client device to set the times at which the client device is to communicate with the reader device. Further, certain ones of the client devices may be afforded some level of priority, in which case the masks would be set accordingly. For example, masks may be set according to a class of a user of a PDK or to a class of the PDK itself. To facilitate such differentiation, priority level or tier level data may be present in an RDC or CRDC to be used when setting a mask for a particular client device or group thereof. Thus, in such a manner, there is provided a technique for dynamic real-time tiered client access. Moreover, it is noted that in one or more embodiments, a CSMA-CA mechanism may be implemented as a backup approach to facilitate data exchange.

Further, in one or more embodiments, utilization of a tiered access system to transfer and receive data to/from a specific user or client device anywhere within a wireless network may allow for simultaneously operating network-wide two-way communications without altering the network. Thus, in other words, although one or more embodiments relate to an autonomous wireless proximity sensing and data transfer network, such a network may be used to notify, page, or transfer data possibly unrelated to one or more of the applications which a majority of the client devices on the network are using (or typically use) (such applications being for the purposes of, for example, tracking, access control, and/or digital rights management). In another example, a network device may be able to associate a PDK ID to a particular user and then provide messaging capability based on the identity of the user. Thus, in this case, one or more embodiments may be combined with tiering to provide multiple messaging levels for different users.

The ability to assign tiers to the network may also enable low latency responses from targeted client devices. Accordingly, by integrating features into the client device that may take advantage of a two-way network capability, a system in accordance with one or more embodiments may allow for the simultaneous communication and control of external devices via real-time client command along with a general purpose low data rate two-way network.

Continuing with the description of c-beacon information in accordance with one or more embodiments, a "site_ID" field may carry a value that each CRDC transmits to all PDKs and RDCs within a coverage area of the CRDC. The site_ID value allows a PDK to determine if it can access the current site or if it needs to request permissions to access the site's network.

| Name | Type | Valid Range | Description |
| --- | --- | --- | --- |
| Site_ID | Integer | 0 to 65535 | Defines the current sites ID. |

A "CRDC_JD" field may carry a value that each CRDC transmits to all PDKs and RDCs within a coverage area of the CRDC. The CRDC JD may be used, for example, for geographical reference.

| Name | Type | Valid Range | Description |
| --- | --- | --- | --- |
| CRDC_ID | Integer | 0 to 65535 | Defines the current CRDC ID. |

Figure 19:
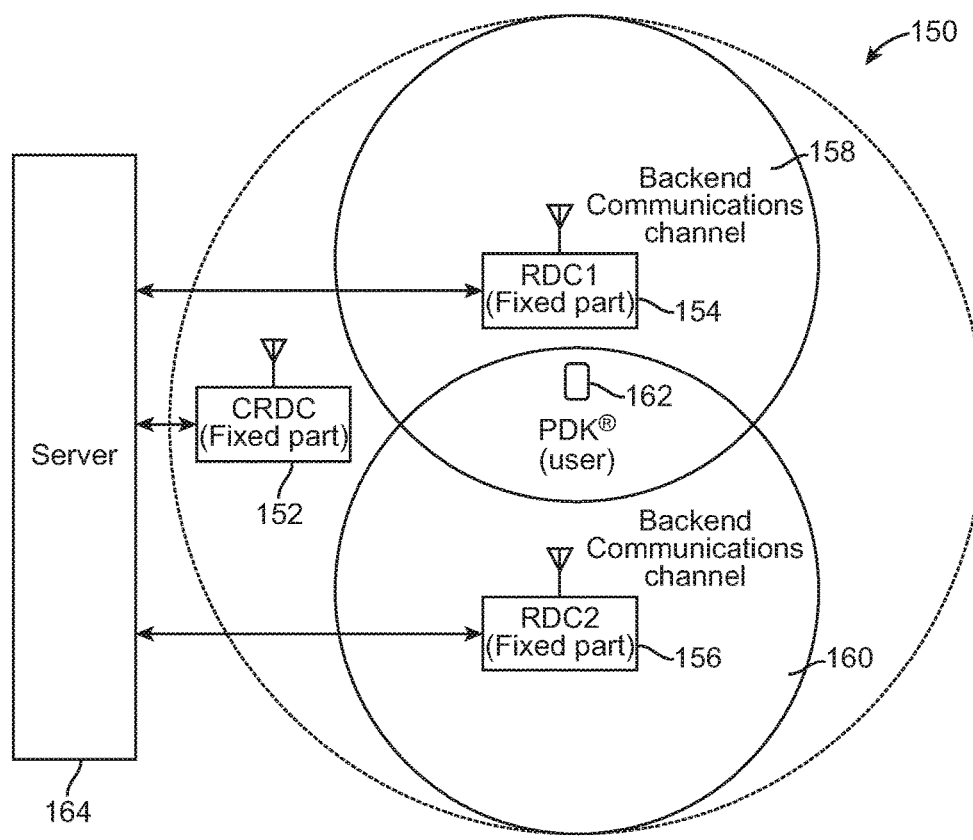
FIG. 19 shows a location tracking system configuration in accordance with one or more embodiments of the present invention.
Figure 20:
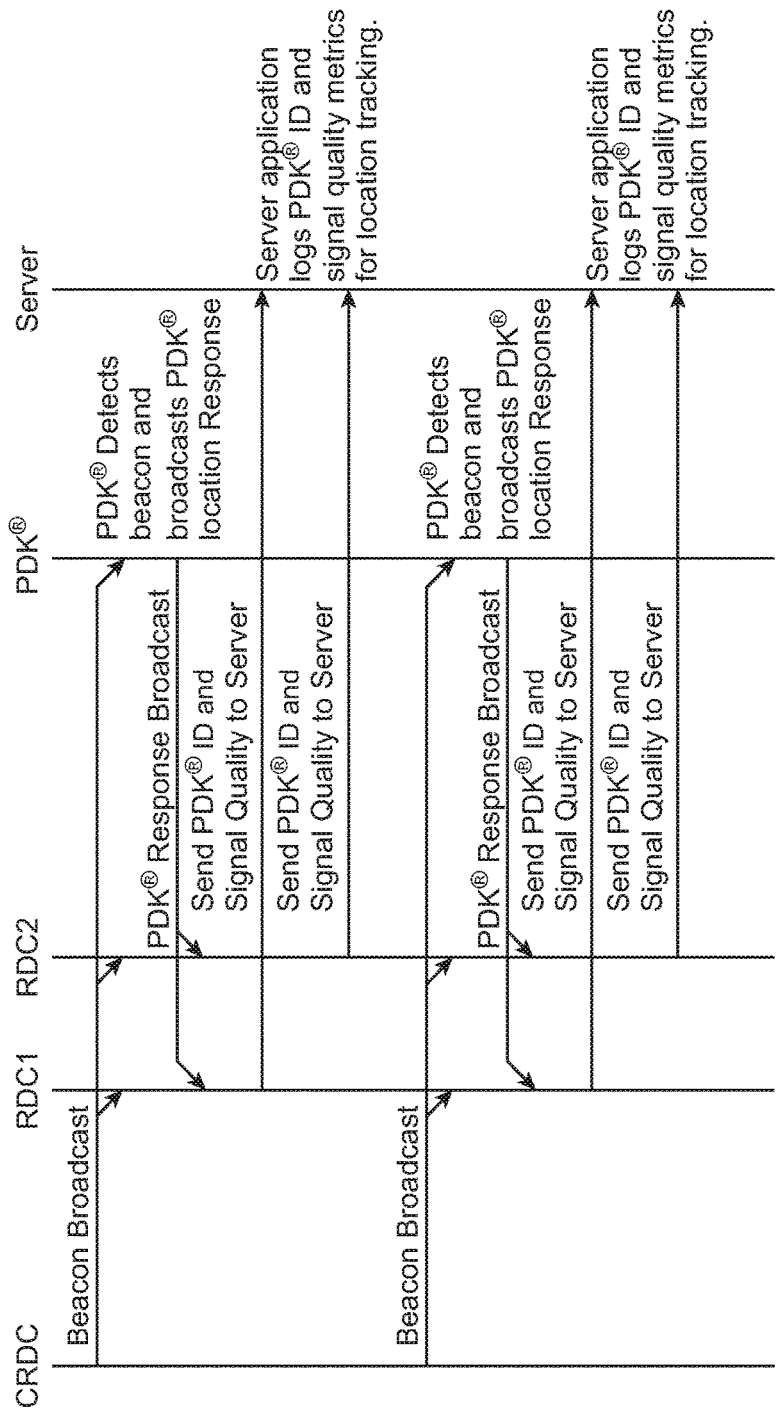
FIG. 20 shows a coordinator RDC (CRDC) location tracking handshake in accordance with one or more embodiments of the present invention.

Now turning to a description of a use of a c-beacon, reference is made to FIGS. 19 and 20. A location tracking example in accordance with one or more embodiments is shown in FIG. 19. There are various different types of devices in the system 150 shown in FIG. 19. First, there is a CRDC 152 that may provide system information and facilitate synchronization for RDCs and PDKs. The system 150 also has RDCs 154, 156, which listen for PDKs and report the status of each PDK found within its respective cell 158, 160. The system 150 further includes a PDK 162 that is mobile and capable of being moving around. Further, the system 150 has a server 164, which is the back-end computer that controls the CRDC 152, acquires information from the RDCs 154, 156, and may provide a graphical representation to monitoring personnel via a computer monitor (not shown).

Accordingly, FIG. 19 shows how location tracking of a PDK is possible and a handshake between different parts of the system 150. A handshake example of PDK location tracking in a CRDC configuration is shown in FIG. 20. The CRDC 152 periodically broadcasts a beacon in timeslot 0 of each superframe. Enabled client devices within the CRDC cell boundary receive the beacon. After the PDK 162 receives the beacon and determines that the beacon is from a system that it is registered to, the PDK 162 broadcasts a PDK location response that is received by the RDCs 154, 156. Both RDC 154 and RDC 156 receive the response, log the PDK ID, the signal quality metrics, and timestamps the information. The packet of information may then be sent to the server 164, where the server 164 processes the data from each RDC 154, 156 and performs a location estimation that may then be presented to an operator. At the beginning of the next superframe, the beacon is again transmitted and the process is repeated until the PDK 162 can no longer be heard due to it being out of range.

In some embodiments, signal quality metrics are used to determine the proximity of a PDK to a location. For example, the proximity of a PDK to a biosensor, in one embodiment, may be determined when the server 164 compares the location estimation of the PDK to the location of the biosensor. For another example, assume a RDC is located at or near a biosensor, in one embodiment, that RDC alone may determine the proximity of a PDK to the sensor based on signal quality metrics (e.g. signal strength).

In some embodiments, the signal quality metrics are used to determine one or more of a PDK's approach to and departure from a location. For example, the approach/departure of a PDK to/from a biosensor, in one embodiment, may be determined when the server 164 compares location estimations of the PDK to the location of the biosensor over time. For another example, assume a RDC is located at or near a biosensor, in one embodiment, that RDC alone may determine the approach/departure of a PDK to/from the sensor based on signal quality metrics (e.g. signal strength) over time. Such embodiments may be advantageous, for example, detecting the approach of a PDK to a biosensor may allow for the buffering of biometric data and enable the user to perform any subsequent biometric authentication more quickly. For another example, a benefit may be allowing for a pending transaction to be cancelled or suspended when the PDK is no longer in proximity or is departing.

Figure 21:
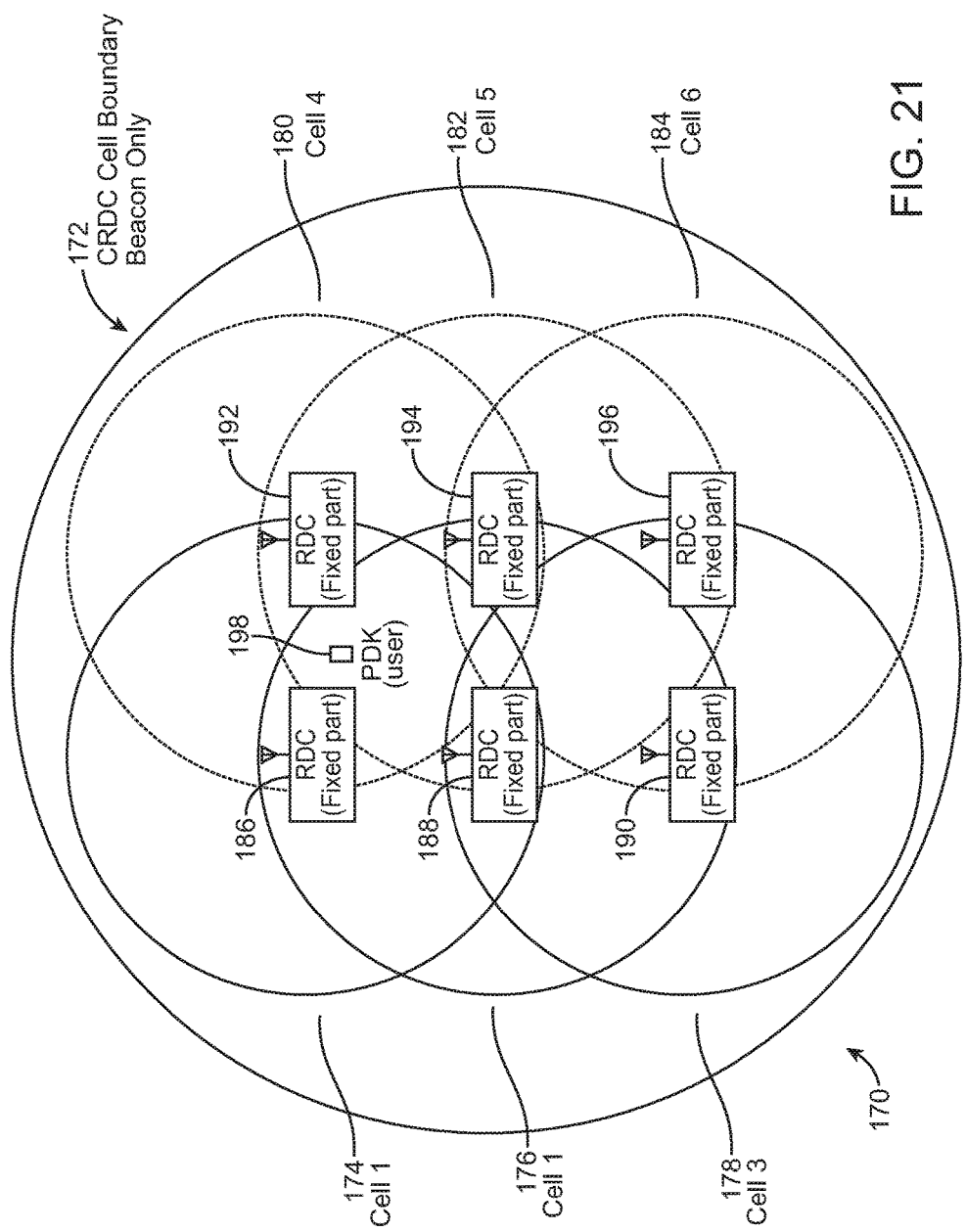
FIG. 21 shows a configuration in which RDCs and PDKs are coordinated within a CRDC cell in accordance with one or more embodiments of the present invention.

Now referring to FIG. 21, it shows a system 170 in which both PDKs and RDCs are coordinated within a CRDC cell boundary. Because, in one or more embodiments, RDCs are stationary devices and may occasionally be relocated, the RDCs may be initially coordinated by manually configuring both timeslots and frequencies they operate on.

As shown in FIG. 21, one CRDC cell 172 and 6 smaller RDC cells 174, 176, 178, 180, 182, 184 exist. The CRDC cell 172 provides ubiquitous coverage to the RDC cells 174, 176, 178, 180, 182, 184. Each RDC cell 174, 176, 178, 180, 182, 184 overlaps its adjacent RDCs in a manner resulting in a high rate of collisions if the RDCs 186, 188, 190, 192, 194, 196 attempt to communicate with a PDK 198 on the same channel. It is envisioned that all the RDCs 186, 188, 190, 192, 194, 196 could be on different frequencies, but then the PDK 198 would be required to access each frequency for some duration, resulting in reduced battery life. To eliminate interference between the RDCs 186, 188, 190, 192, 194, 196 and provide the PDK 198 with an efficient means to conduct secure transactions, the system 170 shown in FIG. 21 may be used.

To optimize the system 170 for battery conservation of the PDK 198, each RDC 186, 188, 190, 192, 194, 196 may be provided with a dual RF physical interface. The primary interface is for monitoring a c-beacon and the PDK 198 located in close proximity, and to signal the PDK 198 to switch to another channel for further communications with that particular RDC. In this case, the CRDC (not shown) may transmit c-beacons, whereby all RDCs and PDKs will gain timing synchronization.

Based on the configuration shown in FIG. 21, the c-beacon fields described above may be configured as follows: superframe_len=4 (2↑4=16 timeslots); c-superframe_len=4 (2↑4=16 superframes); CRDC_chan_flags=b0000000000000010 (most significant bit to least significant bit—CRDC channels); PDK_sf_ts_msk=b000000000011111 (mask all but 2 least significant bits of the superframe count and don't mask any timeslot bits); site_ID=0x1234 (arbitrary site identification); and CRDC_ID=0x0001 (arbitrary CRDC_ID).

Another piece of information that may be inherent to the PDK is a unique service provider PDK ID. The unique service provider PDK ID is located in the PDK and may be compared with the superframe and timeslot count prior to applying the mask, but may not affect the superframe and timeslot counts from a time reference standpoint. In this case, the unique service providers PDK ID for this PDK may be equal to 0x0003.

Using the above described values for the c-beacon, the following system attributes result (the superframe is 16 timeslots long, so once out of every 16 timeslots, a c-beacon is created allowing the PDK to determine if a system with the correct system ID exists): the c-superframe length is set to 16; the CRDC_chan_flags indicate to the PDK the number of CRDC channels available in the system; the PDK_sf_ts_msk indicates which bits to logically AND with the superframe and timeslot count to determine which slots to respond on (in this case, the PDK_sf_ts_msk is a hex value of 0x001F that is ANDed with the superframe and timeslot count resulting in one response timeslot); and the site_ID and CRDC ID are arbitrary values and may be left to the service provider for selecting unique identification values.

Figure 22:
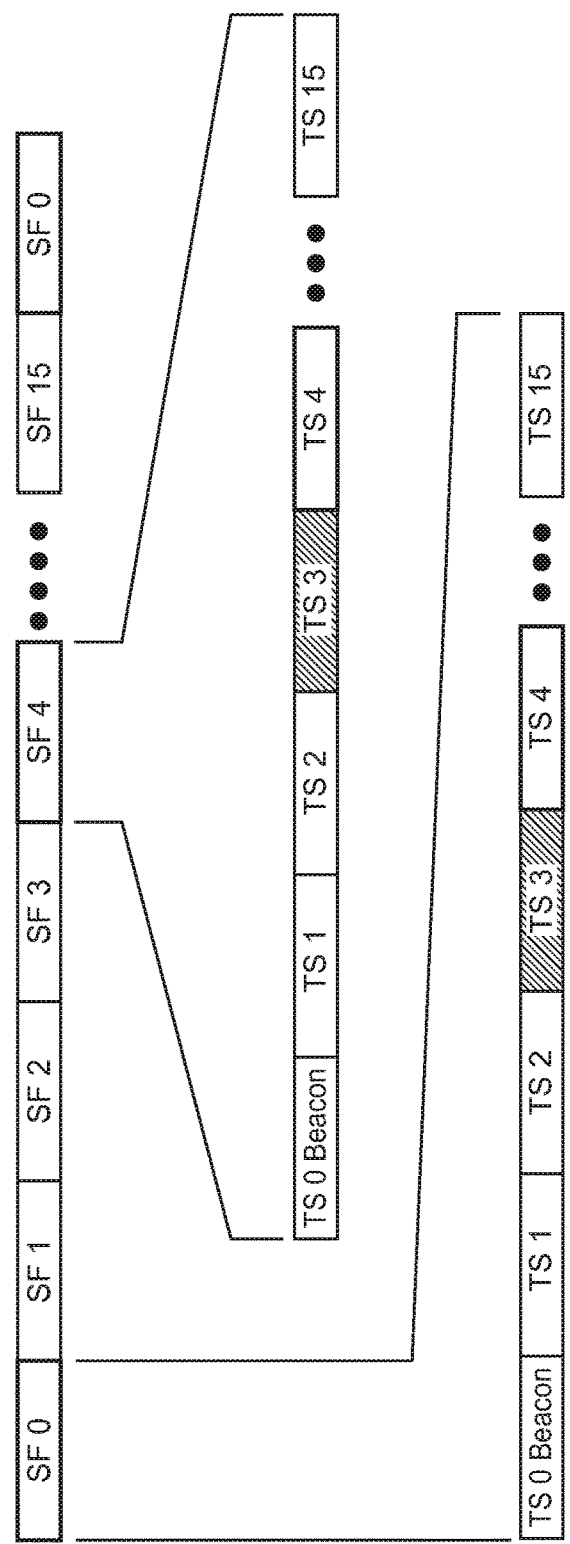
FIG. 22 shows a CRDC framing and PDK timeslot response operation in accordance with one or more embodiments of the present invention.

Using the above described exemplar system configuration information and having a PDK with a unique service provider ID of 0x0003, FIG. 22 shows how the PDK may operate in a CRDC framing structure. As shown in FIG. 22, the c-superframe_len is set to 16—thus, the superframe count counts from 0 to 15 and then starts over at 0. Each superframe then includes 16 timeslots of which the first timeslot is timeslot 0 and includes the beacon. The superframe_len is also set to 16—thus, there are 16 timeslots for each superframe. Again, the timeslots are numbered from 0 to 15, and restart at 0 for each superframe.

In one or more embodiments, based on the parameters set by the system and the unique service provider PDK ID, the PDK may periodically transmit a PDK location response in timeslot 3 of each superframe on a modulo 4 basis. This causes the PDK to respond in timeslot 3 of superframes 0, 4, 8, and 12 of a c-superframe. It is noted that the PDK may follow the CSMA-CA standard and if the PDK cannot respond in its timeslot, it may wait for its next designated superframe and timeslot to respond.

If an RDC requests to begin communication with a PDK, the RDC may immediately respond on the next even timeslot, which, in this case, is timeslot 4. Any RDC may respond, but RDCs may have to use the CSMA-CA rule prior to responding to the PDK transmission. If an RDC begins communications with a PDK, the following timeslot may be used to instruct the PDK to go to another channel, where bi-directional communications may commence.

Further, in one or more embodiments, an active superframe may occur when unmasked bits in the superframe count equal the corresponding unmasked bits in the unique service providers PDK ID. In this case, the superframe mask is a value of 0x003 and the unique service provider PDK ID is 0x0003.

With this information, the following calculation occurs:
b000000000000 superframe count[15:4]
xor b000000000000 unique Service Provider PDK® ID[14:3]
b000000000000 result of xor function
and b000000000111 Superframe Mask[11:0]
b000000000000 result of AND function
nor all bits
1 result is true As shown above, a portion of the superframe count is exclusive-ORed with a portion of the unique service provider PDK ID. The result of the exclusive-OR is all 0's. Then, the superframe mask is ANDed with the result of the exclusive-OR function. The AND operation also results in all 0's. The result of the AND function is then compared to zero by NORing all of the bits together and results in a 1 or "true" output, indicating the bits compared between the superframe count and the unique service provider PDK ID are a match.

An active timeslot occurs when the unmasked bits in the 3 most significant positions of the timeslot count equal the unmasked bits in the unique service provider PDK ID's 3 least significant bits and the timeslot count least significant bit is a 1 (the PDK transmits on odd frames). In this case, the timeslot mask is a value of 0x7 and the unique service providers PDK ID's 3 least significant bits are 0x3.

With this information, the following calculation occurs:
b011 timeslot count[3:1]
xor b011 unique Service Provider PDK® ID[2:0]
b000 result of xor function
and b111 Timeslot Mask
b000 result of AND function
nor all bits
1 result is true As shown above, the timeslot count is exclusive-ORed with a portion of the unique service provider PDK ID. The result of the exclusive-OR is all 0's. Then, the timeslot mask is ANDed with the result of the exclusive-OR function. The AND operation also results in all 0's. The result of the AND function is then compared to zero by NORing all of the bits together and result in a 1 or "true" output, indicating the bits compared between the timeslot count and the unique service provider PDK ID are a match.

The last portion of the calculation that needs to be completed (as described above) is to verify the last bit of the slot count is a '1,' indicating an odd slot. If the unmasked superframe and timeslot bits do not match the appropriate unique service provider PDK ID, the results will be "false" and no match will occur. In the examples described above, the superframe mask was set to unmask the 2 least significant bits of the superframe count to show that it is possible to allow a PDK to come up more frequently than the c-superframe count. By increasing the superframe mask to 4 bits, this example would allow the PDK to respond once per c-superframe (because the c-superframe was set to 16) and the modulo for the mask would be 24, or 16.

The timeslot mask may be set to allow all timeslot bits to be correlated to determine the timeslot, allowing the PDK to respond once per superframe. Further, it is noted that it may be possible to mask some of the timeslot bits to increase the number of times a PDK can respond within a superframe.

In one or more embodiments, a PDK may periodically wake up to determine whether it is within a particular system. Upon a periodic wake up, the PDK will detect a c-beacon indicating that the particular system is present, along with system information. The PDK will collect the system information and determine the current superframe count of a c-superframe. The PDK may also put parameters (e.g., PDK_sf_ts_msk) in place to start immediate battery save in the system.

Based on an approximate time, the PDK may awake just prior to where it believes the next superframe is that it should communicate on, and will listen for the beacon and begin responding with the PDK location response message.

Figure 23:
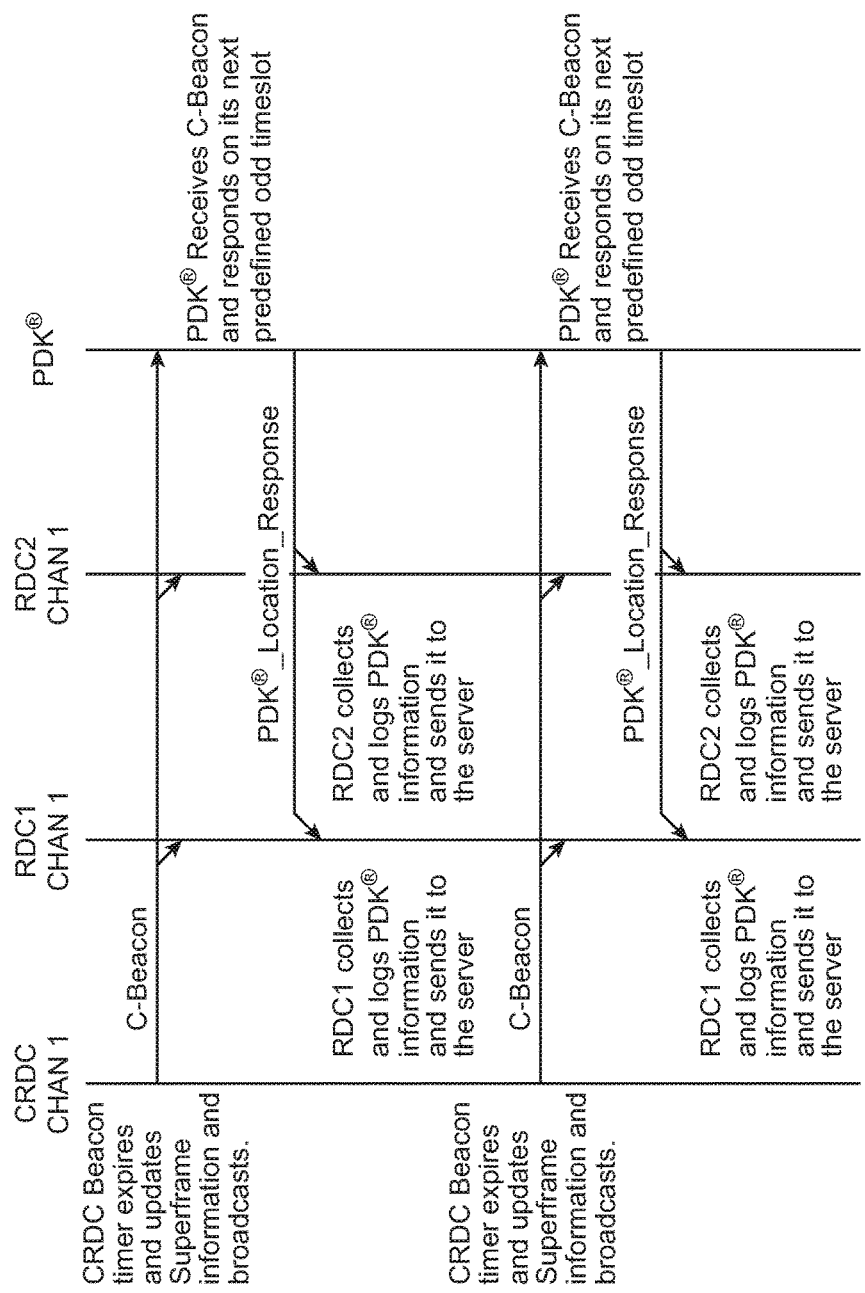
FIG. 23 shows a CRDC beacon and PDK response handshake in accordance with one or more embodiments of the present invention.

As shown in FIG. 23, a CRDC may update its system information on each superframe and output a c-beacon with current information to all PDKs and RDCs. The PDK then waits for its predefined superframe and timeslot and responds. This scenario continues to occur until the PDK leaves the CRDC cell or an RDC responds to the PDK.

Figure 24:
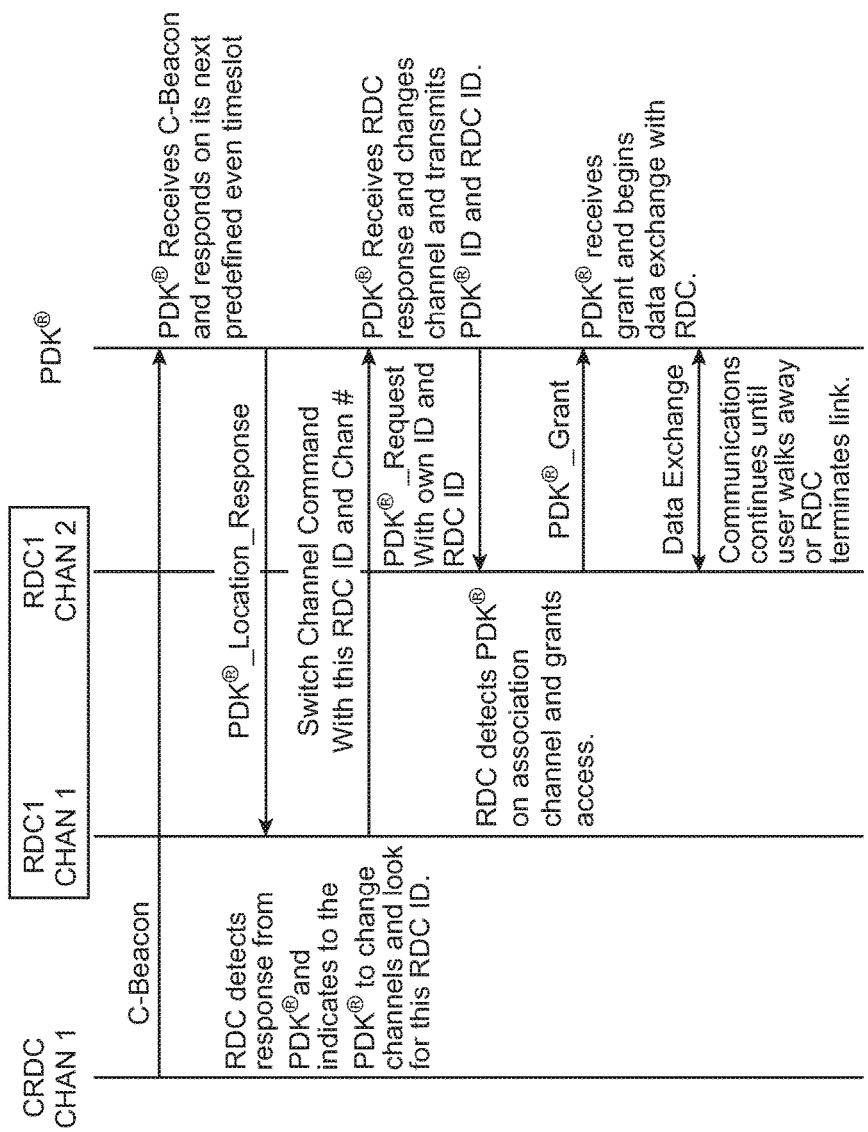
FIG. 24 shows a PDK/RDC association in a CRDC cell in accordance with one or more embodiments of the present invention.

As described above, a CRDC may continue to output a c-beacon, and the PDK periodically awakes to re-align to the superframe and respond to the c-beacon. If a RDC is present and wants to communicate with the PDK, the RDC may respond on the even timeslot immediately available after the PDK's transmission. FIG. 24 shows how the communications handshake between the PDK and RDC may occur. Particularly, FIG. 24 depicts one CRDC, one RDC with two active channels (i.e., using two wireless links), and a PDK.

With continued reference to FIG. 24, the CRDC outputs a c-beacon of which the RDC and PDK are aligned. The PDK realizes that the c-beacon's superframe count correlates to its internal predefined active superframe count, and then waits for the appropriate timeslot to respond to the system with its PDK location response. When the PDK responds on the c-beacon channel, the RDC detects the response and determines that it wants to associate with the PDK. The RDC then creates a message including its own RDC ID, the PDK's ID, a command to switch to channel 2, and a predicted superframe and timeslot the PDK should respond on. The PDK, in response, switches to channel 2 and waits for the appropriate superframe and timeslot count and transmits a link request along with its PDK ID and the destination RDC ID. The destination RDC then receives the information and responds back to the PDK with a link grant. Communications may now begin between the two devices exchanging the appropriate information to maintain the PDK-RDC link. To maintain synchronization, the RDC may define the periodic communication frequency with the PDK and will periodically generate a request to the PDK to exchange information. The PDK may then reconfigure its wake parameters to that of the RDC, as the RDC is maintaining superframe synchronization.

It is noted that in one or more embodiments, such as that described immediately above, the RDC may have a dual physical interface, maintaining synchronization with the CRDC on channel 1, while associating with one or more PDKs on channel 2. The physical interface connected to channel 1 provides timing to the physical interface on channel 2.

Further, because the RDC may have intelligence on both channels, the RDC may provide coordination of PDKs that it wants to redirect to channel 2 and PDKs that are on channel 2. More specifically, the RDC may move the superframe and timeslot that a PDK communicates to the RDC on, if another PDK with the same timeslot requirements is present on channel 1 and the RDC wants to associate with it.

CRDC Slot and Channel Coordination

In one or more embodiments, a CRDC may be configured via a remote connection to a server or automatically. Using remote configuration, the server may have knowledge of RDCs located within the CRDC cell boundary and may perform optimum channel and timeslot planning.

When the CRDC is configured automatically, the CRDC may scan all channels and find the channel with the least interference. The CRDC may then begin transmitting a c-beacon.

All RDCs located within a CRDC cell boundary may place the CRDC into its local CRDC database and complete scanning all other channels to determine if other CRDCs are present. In the case multiple CRDCs are found, the RDC may communicate to each CRDC its findings if possible.

Each CRDC may coordinate through that RDC to setup channels and timeslots to prevent interference between CRDCs. In one or more cases, the CRDC may select another channel and disregard the timeslot information because CRDCs may not be required to be timing coordinated. Further, it is noted that any RDC that detects more than one CRDC may select the CRDC with the best signal quality.

Protocol Operation

The following describes a protocol operation in a single cell coordinated system using a CRDC configuration. In one or more embodiments, there may be additional protocol fields required to allow interoperability between single cell and coordinated multi-cell configurations. Such additional protocol fields may provide information to RDCs and PDKs that are located in near proximity to each other, or within a CRDC cell.

A network format field may provide information to RDCs and PDKs related to the specific configuration the single cell or coordinated cells are operating in.

| Name | Type | Valid Range | Description |
| --- | --- | --- | --- |
| Proxense_NWK_FMT | | | Defines the network configuration employed for an RDC or CRDC |
| Network Type | Integer | 0 to 7 | Defines the network type employed.<br>0 = Single Cell<br>1 = Multi-Cell coordinated<br>2 = Multi-Cell coordinated w/ CRDC<br>3-7 = RFU |
| Beacon Source | Binary | 0 or 1 | Defines the source of the beacon.<br>0 = RDC<br>1 = CRDC |
| Broadcast Flag | Binary | 0 or 1 | Defines if this is a broadcast message.<br>0 = not broadcast<br>1 = broadcast |
| Timeslot Select | Integer | 0 to 3 | Defines how an RDC and PDK ® utilize timeslots in a system.<br>0 = no timeslots assigned<br>1 = 802.15.4 Beacon enabled<br>2 = PDK ® uses even timeslots/RDC uses odd timeslots<br>3 = PDK ® uses odd timeslots/RDC uses even timeslots |

A network type value may be used to define a cell network configuration. An RDC receiving this field may determine its operating mode based on this field. If an RDC receives a network type of single cell from another transmitting RDC, the RDC may tune to another channel to avoid collisions with the other RDC. If the RDC receives a network type of coordinated multi-cell, the RDC may join the multi-cell coordinated system. If the RDC receives a network type of coordinated multi-cell with CRDC, the RDC may join the CRDC network if the site ID is the same.

The PDK may also receive this information and adjust its operating mode to comply with the system employed. If the PDK detects the system to be single cell, the PDK may conform to more of an IEEE 802.15.4 protocol, communicating with the RDC in such a manner. The PDK may be aware that it is required to communicate with a specific RDC ID. The PDK may still have the capability to periodically monitor other channels for other RDCs in the local vicinity.

If a PDK detects the system is multi-cell coordinated, the PDK may receive further information indicating the other RDC frequencies in use in the coordinated network and may adjust its system operating parameters appropriately.

If the PDK determines the system is multi-cell CRDC coordinated, the PDK may adjust its operating parameters appropriately. The PDK may acknowledge that a c-beacon is present and may broadcast a PDK location response. The PDK may also understand that an RDC with a different ID other than a CRDC ID may attempt to communication with the PDK.

A "beacon source" field may indicate to all RDCs and PDKs in the general proximity of the type of beacon being generated. This information may be helpful, specifically when in a multi-cell CRDC system, and allows RDCs to distinguish between RDC generated beacons and CRDC generated beacons.

A "broadcast flag" may indicate to all recipients that the information being sent is intentionally being broadcast to all devices that can receive particular protocol information. In some cases, a message that may be sent to a specific PDK may also be broadcast to all PDKs. This flag assists the PDKs in determining how to treat the information.

A timeslot select field may indicate to PDKs and RDCs how the timeslots are configured in the system. This field may further be used to determine if an RDC and PDK are to use even-based or odd-based timeslots for responding.

In order for an RDC or PDK to determine that a network is of a particular type, a network identifier may be used.

| Name | Type | Valid Range | Description |
| --- | --- | --- | --- |
| Proxense Network Identifier | ASCII | Proxense | An 8 byte ASCII value identifying the network to be a Proxense network |

Single Cell Standalone Operation

The following description is based on, for example, an electronic game (such as one that may be found in a casino) operating in a single cell configuration and attached to some central server. However, it is noted that as described above, examples of applications and uses are for purposes of illustration and clarity and do not limit the present invention.

The game has a resident RDC integrated into its hardware and has a system stack that allows access to the game. The RDC may be attached to the game controller, or may use a separate controller containing the system stack and an interface to the central server.

For clarity, any interactions between the RDC and the server will assume that the reader understands that the system stack and server interface application are taken into account in the transactions described.

This description covers the basic initialization of the system and RDC/PDK interactions that occur while associated in the system. The following concept defines how, for example, a casino game in a single cell configuration may be setup with multiple player PDKs. Upon power being applied to the game and RDC, the internal circuits perform an initialization function and the operating system and game load. The game and RDC indicate to the central server that power has been applied. The system stack also loads in the controller and the RDC device is started in a static mode with its transceiver disabled. The RDC may first be configured to operate in a single cell environment and requires some basic setup requirements as will be understood by those skilled in the art.

The server places the game into a particular configuration mode where it can set the RDC for auto-discover mode, or may choose to manually configure parameters related to the RDC's operation. If the server places the RDC into auto-discovery mode, the RDC generates a random value for its RDC ID and its password, which is then passed back to the server.

If the server chooses to manually setup the RDC, the server may supply the RDC ID and password. The server may also send the network topology and preferred channels the RDC will operate on. The central server may then send its site information to the game controller, which is also used by the RDC to allow access to the game. Once the server has configured the RDC, the server will enable the RDC and game.

The configuration information shown in the table immediately below may be used for RDC provisioning.

| | | |
|---|---|---|
| Site ID | 0x0100 | Generic value for a single cell RDC. |
| RDC ID | 0x1234 | Arbitrary value |
| C-Superframe Length | 32 | 2.5 second superframe period for PDK ® wakeup |
| Superframe Length | 16 | 16 slots per superframe |
| Proxense Network Identifier | Proxense | Defines system as a Proxense system |
| Proxense Network Format | | |
| Network Type | 0 | Single Cell |
| Beacon Source | 0 | RDC |
| Broadcast Flag | 1 | Broadcast |
| Timeslot Select | 1 | 802.15.4 timeslots |

In this configuration of a standalone RDC (without a site identifier): the site ID is set to 0 because this is a single cell RDC and no site information is required; the RDC ID is arbitrarily selected; the c-superframe length is set to 32 superframes indicating to the PDK that it needs to wake up once every 32 superframes in superframe 0 to exchange information with the RDC to remain associated; the superframe length is set to 16, which may be the standard value for a superframe in a particular system; the network identifier allowing a PDK to understand the beacon is from an enabled RDC; and the network format indicates one or more of several parameters (e.g., the network type indicates to the PDK that it is a single cell network—indicating to the PDK no other RDC is associated with this RDC and therefore no other RDC should be attempting access on this channel, the beacon source indicates to the PDK that the beacon is from an RDC and not a CRDC device, the broadcast flag indicates to the PDK that the message is being broadcast from the RDC, the timeslot select field indicates that a PDK should use IEEE 802.15.4 beacon-based handshaking with the RDC). The RDC then scans all channels (or preconfigured channels) to determine if any other IEEE 802.15.4 or client devices are present or if any other interference is found.

With the pre-configured information, the RDC then begins beacon transmission on the least interfered channel with a c-superframe count, superframe count, and the information located in the table immediately described above.

Figure 25:
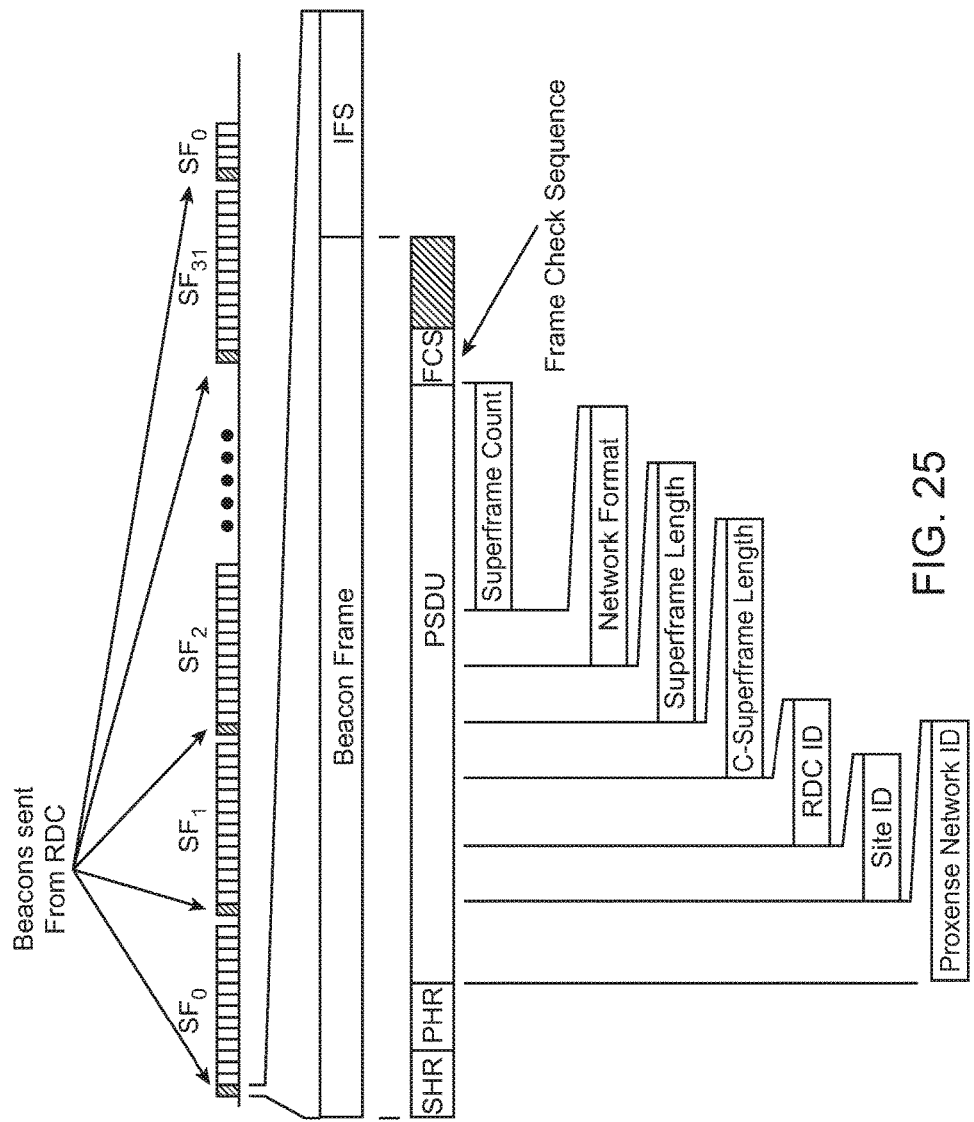
FIG. 25 shows an RDC beacon transmission in accordance with one or more embodiments of the present invention.

Now, as shown in FIG. 25, in standalone mode, the RDC will continue to transmit beacons on every superframe. The information in the table immediately described above may be transmitted along with the superframe count in every superframe to allow the PDK to configure and synchronize with the system. When the superframe count is the superframe length minus one, the superframe count will start counting from 0 for the next c-superframe.

At the end of each beacon transmission, a frame check sequence (FCS) may be appended as part of the IEEE 802.15.4 physical layer. The FCS provides protection for the data carried in the frame. Because the beacon may not occupy the entire frame (or timeslot), hashed lines are shown indicating additional idle time between the FCS and IFS. The RDC maintains the beacon transmission until the RDC is disabled or power is removed. At this point in the sequence of operations, there are no PDKs registered with the RDC, so no PDK can gain access without registering and receiving authorization from the RDC.

Figure 26:
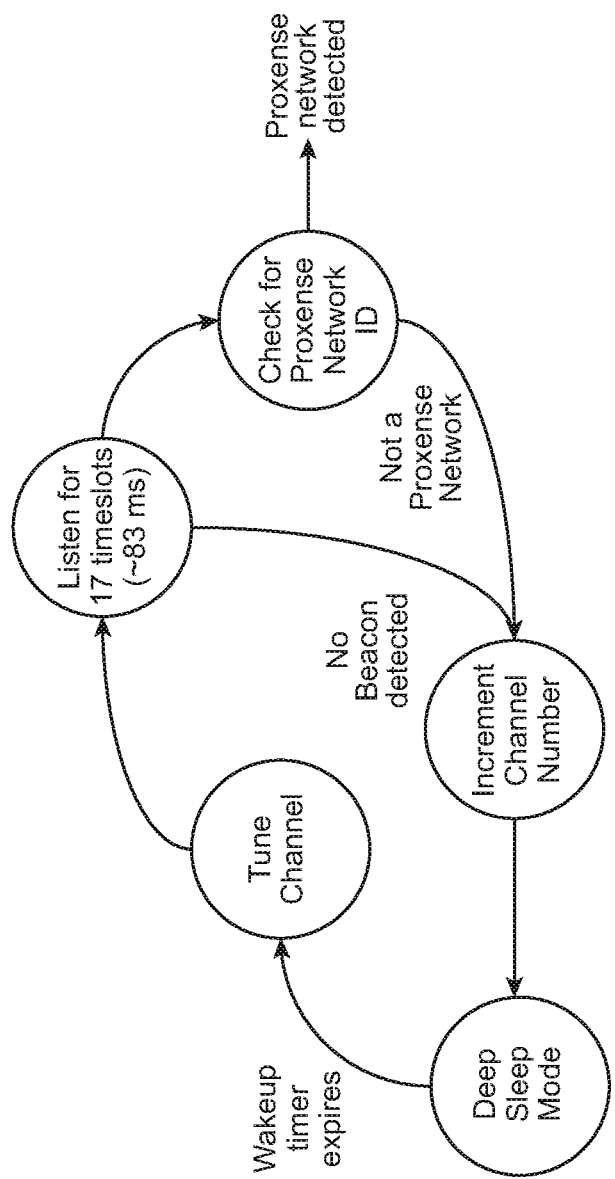
FIG. 26 shows a deep sleep state diagram in accordance with one or more embodiments of the present invention.

Again referring to the casino game example described above, a player with a PDK that has not yet been registered to the property enters the RDC cell. The PDK is in battery save mode and periodically wakes up looking for a network. As shown in FIG. 26, the PDK starts in a deep sleep state. The wakeup timer eventually expires, causing the PDK to enable and tune its receiver. The PDK then monitors the channel that it tuned to for a period of one 17 timeslots (one superframe plus one slot), or approximately 83 milliseconds. The 17 timeslot limit is based on a superframe of 16 timeslots, and the fact that the PDK, upon initial reception, could miss the beginning of a beacon. The additional slot provides the overlap necessary to guarantee reception of a beacon if one is present.

If no beacon is detected, the channel number is incremented (modulo 16) and the PDK resets its wakeup timer and returns to deep sleep mode. If a beacon is detected, the PDK checks for a network ID and if one is not found, it again increments the channel number, resets its wakeup timer, and returns to deep sleep mode. If the network ID is detected, the PDK attempts to establish a communications link with the RDC. At this point, the PDK has found a single cell network on channel 1 with an RDC ID of 0x1234, and the RDC is in broadcast mode indicating that it is attempting to gain the attention of any PDKs in the local proximity.

Figure 27:
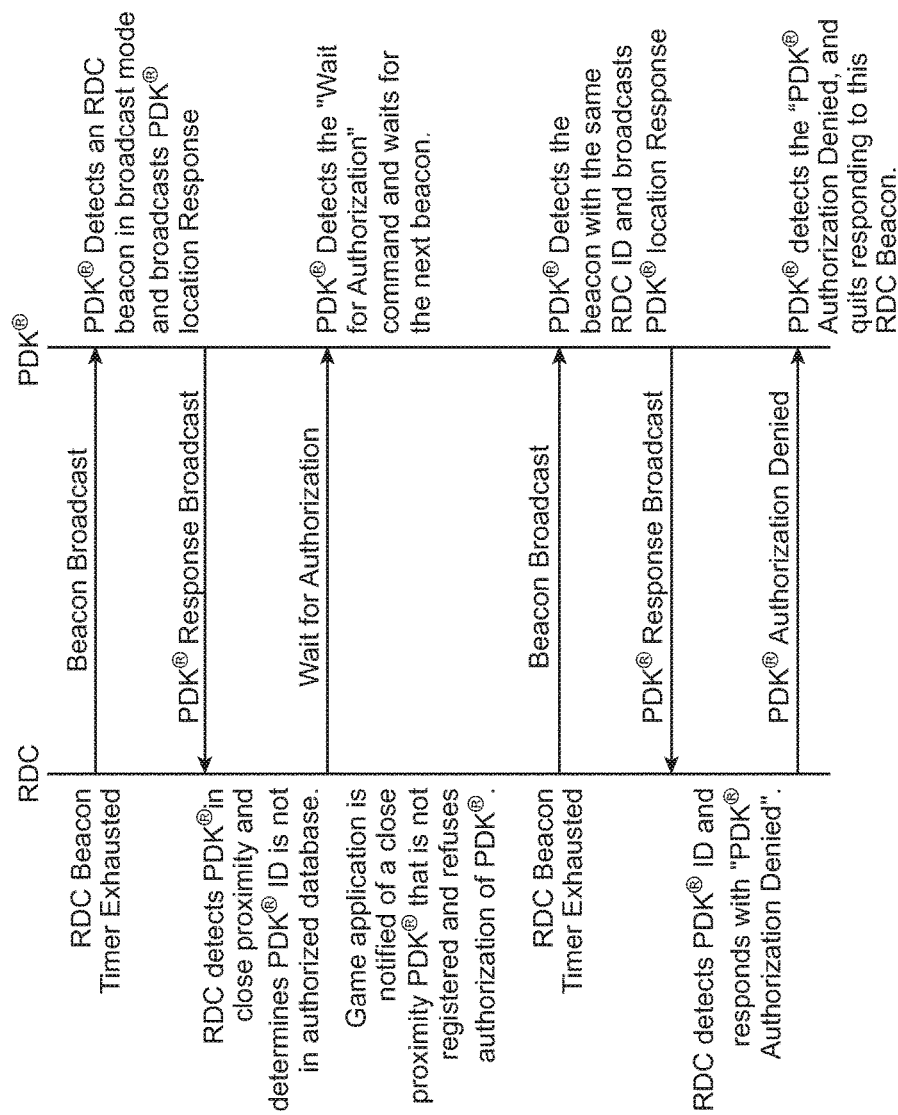
FIG. 27 shows an authorization denial handshake operation in accordance with one or more embodiments of the present invention.

Now referring to FIG. 27, in which an authorization denial handshake is shown, the RDC broadcasts its beacon with the information as described above. The PDK detects the beacon in broadcast mode, determines the network configuration and RDC ID and returns a PDK location response with the RDC ID and PDK ID included. The RDC detects the response from the PDK and alerts the central server that a PDK with a public ID of 0x9876 (arbitrary) wants to attach and enable the game for play. In the meantime, the RDC may immediately respond back to the PDK indicating that the PDK should wait for authorization. This keeps the PDK responding to beacons as defined by the fields located in the beacon until the beacon is no longer present (i.e., the PDK is no longer in the RDC cell), or until a response is returned by the RDC.

The central sever, in conjunction with the system stack, may then choose to not recognize a particular PDK's public ID that has not yet been registered to the property. The RDC continues to output its beacon. Upon the next wakeup and PDK location response from the PDK, the RDC detects the PDK ID and, within its database, looks up the authorization parameters for this PDK. It determines that authorization has been denied and sends an "authorization deny" command to the PDK. In the case that a particular PDK is not recognized or not authorized, a notification may sent to a staff member of the property to register a user of the PDK, and/or, in one or more embodiments, one or more machines may be used to prompt the user to register with the property.

The PDK temporarily stores the RDC ID in its local memory with a flag indicating that it shall no longer respond to this RDC ID. The PDK may then go back into battery save mode and periodically scans all channels as previously described above with reference to FIG. 26.

Still referring to FIG. 27, because the PDK may not constantly be aware of its geographical location, the PDK may continue to monitor each channel and decode each beacon. Eventually, the PDK returns to the channel that the RDC is still transmitting beacons on, decodes the beacon information including the RDC ID, and determines that it is not to respond.

Further, the PDK may maintain the RDC ID in its local database until the beacon is no longer present during scanning, at which time the RDC ID is removed from the database. The period of time that the beacon is absent before removing the RDC ID from the database may be determined during prior system testing.

Assuming the RDC beacon is absent for a given period of time indicates to the PDK that the PDK has left the RDC cell. Upon the next detection of that RDC beacon, the PDK may again attempt to gain access to the RDC as shown in FIG. 27. The difference this time is the PDK ID is in the RDC's local database and the RDC may deny authorization without alerting the host system. The PDK may then operate as previously described after authorization has been denied.

Figure 28:
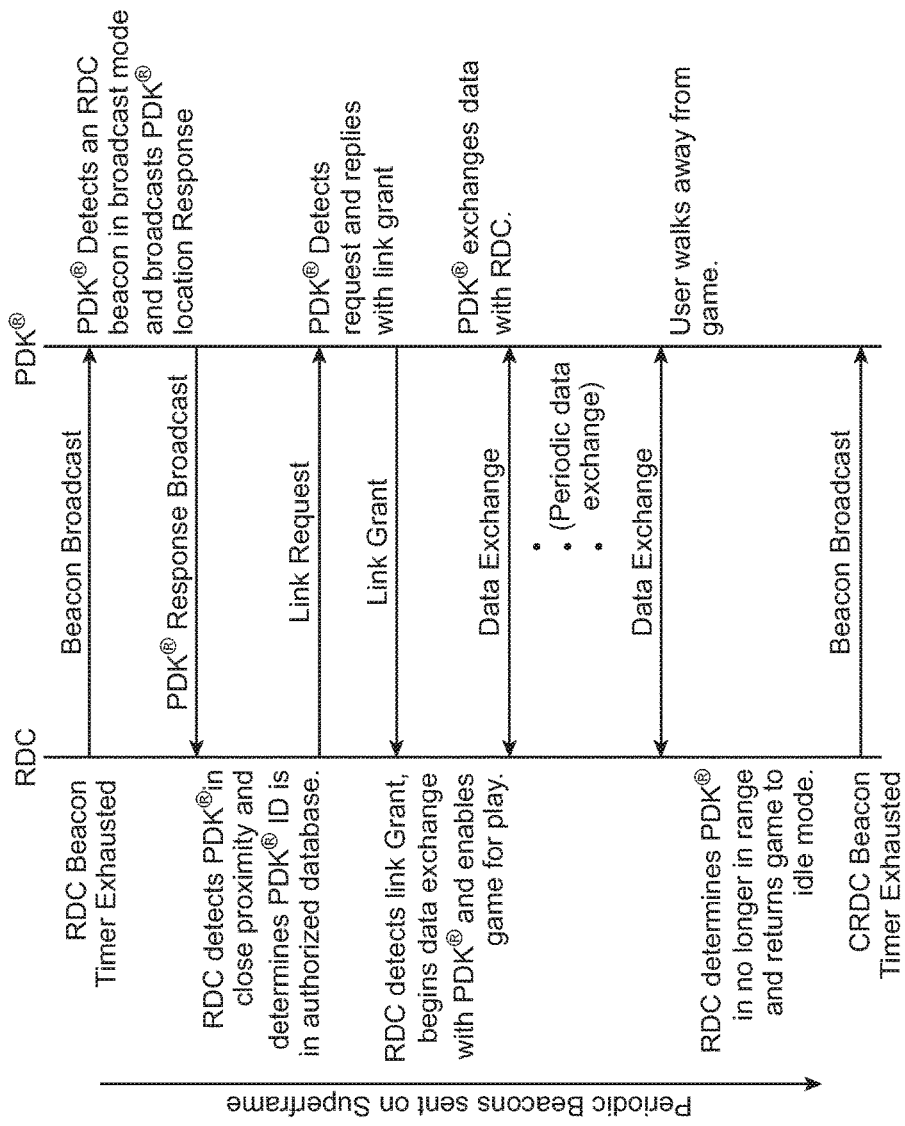
FIG. 28 shows an authorization grant and association handshake in accordance with one or more embodiments of the present invention.

In one or more embodiments, once a host system grants authorization for the PDK to operate within the property, then one or more different scenarios may exist. In one scenario, the RDC may transmit the PDK ID as part of the beacon transmission, alerting the PDK that the RDC wants to communicate, and the PDK may then respond with a PDK location response. In another scenario, the PDK returns to the RDC cell, and after detection of the beacon (with or without the PDK ID), it returns the PDK location response. In either case, after the RDC detects the PDK location response with the PDK's public ID, the RDC then issues a link request attempting to initiate a link between the RDC and PDK. FIG. 28, for example, shows a handshake between the RDC and PDK for a PDK authorization grant.

As shown in FIG. 28, the RDC may broadcast the beacon on every superframe. Although not shown, the superframe counter value is also included, which the PDK may use for battery conservation. The beacon may be broadcast in one of more different methods. The system may have just authorized a PDK and the beacon includes the PDK's public ID for a period of time or, in another method, the beacon may be transmitted without the PDK's public ID. As described above, if the PDK is in the RDC cell and has deactivated its response, when the PDK detects its ID in the beacon, it may reactivate its response to the RDC and transmit both the RDC ID and PDK public ID in its PDK location response.

If the PDK has just re-entered the RDC cell and detects the RDC beacon (with or without the PDK's public ID), the PDK may again respond with the RDC ID and its own PDK public ID. The RDC may then detect its RDC ID and the PDK public ID and immediately sends a link request to the PDK with both its RDC ID and the PDK's public ID indicating it wants to initiate a link with the PDK. The PDK may detect the request and respond with a link grant with both IDs included. The RDC and PDK may enter into association mode and then provide data exchange on a periodic basis insuring the PDK remains in range of the RDC. This periodic data exchange may occur based on parameters previously described above. Interleaved between the data exchange may be beacons that other PDKs may use to access the RDC. Eventually, the RDC may terminate the data exchange based on inactivity, as determined by the server, or as based on the PDK leaving the RDC cell, in which case the RDC realizes the PDK is no longer in range.

Further, it is noted that due to radio interference issues that might occur in wireless systems, the RDC and PDK may not relinquish the link based on the lack of a single data exchange. Because the RDC is not necessarily battery limited, the RDC may continue to monitor all timeslots in a superframe with the exception of those frames it transmits on. In contrast, it is noted that a PDK is likely battery limited and therefore may need to intelligently choose when to receive and transmit.

In the case the RDC and PDK lose communications during the predefined period they are attempting to communicate, both devices may have equal knowledge of such an event. Because the PDK is battery limited, the PDK may try on the next available timeslot to regain synchronization with the RDC. After a period of time in the RDC, or a predefined number of attempts by the PDK, the link may be considered lost.

Referring again to the casino game example, in one or more embodiments, an enabled single cell game facilitates multi-player access via the central server. Individual players may consecutively play the game provided they have the appropriate PDK, or in some instances, multiple players may be able to simultaneously play the game. The RDC allows for simultaneous multi-player access, so long as the central server supports and authorizes such play.

Figure 29:
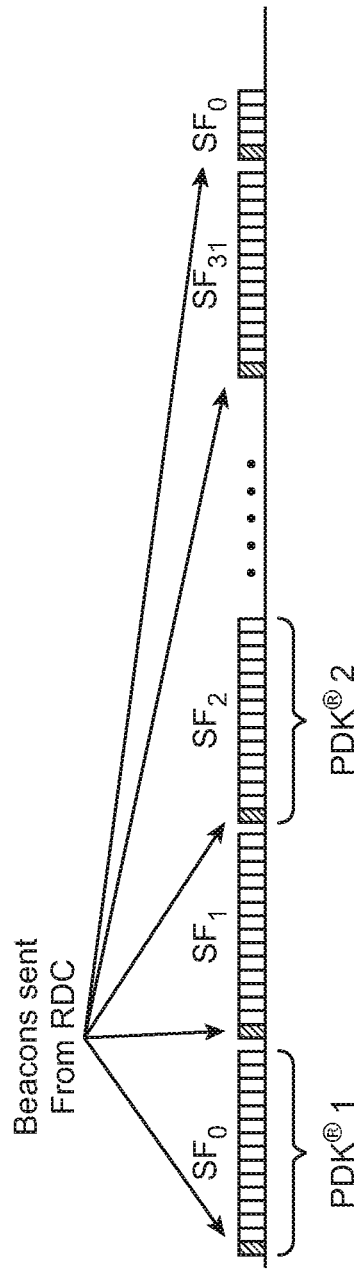
FIG. 29 shows a single cell with multiple PDK access in accordance with one or more embodiments of the present invention.

In the case where multiple PDKs may simultaneously access an RDC, the RDC may provide superframe coordination information to the PDKs to interleave them in a manner to avoid contention between RDC and PDK communications. For example, as shown in FIG. 29, the RDC may assign a superframe and timeslot count to each PDK accessing the RDC. Through link setup and data exchange, the RDC may direct the PDK to use a specific superframe and timeslot (or multiple superframes and timeslots) for periodic data exchange. By using such a technique, the RDC may alter the wakeup superframe for each PDK and may efficiently distribute them so as to reduce contention between the PDKs. Because the PDKs are given a specific superframe and timeslot (or superframes and timeslots), the PDK is required to wake up during that superframe(s) and timeslot(s) to communicate with the RDC. This technique, in turn, may greatly extend PDK battery life.

Figure 30:
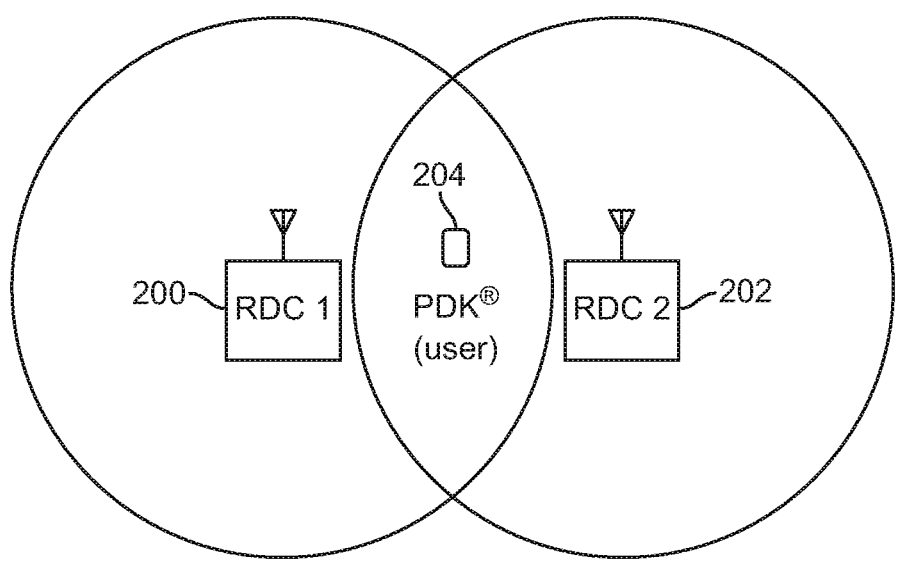
FIG. 30 shows multiple single cell RDCs with cell overlap in accordance with one or more embodiments of the present invention.

Now referring to FIG. 30, it shows a configuration in which multiple games operating as single cell RDCs are co-located in close proximity with overlapping RDC cell coverage. In such a configuration, each RDC 200, 202 may not be aware of the presence of the other RDC 200, 202 but a PDK 204 that resides in the area of overlapping coverage may detect the presence of both RDCs 200, 202. A technique of restricting or allowing PDK access to one or more of the RDCs 200, 202, and the technique of enabling game play may depend on the system stack for that specific configuration.

In a configuration where multiple RDCs are co-located without the knowledge of each other, and where a PDK is registered to both RDCs, a technique of determining and gaining access to each RDC may be enforced. There are one or more possible scenarios that may occur. For example, in one case, a player may desire simultaneous access to a game and another device, such as a drink or food purchase device, with both being physically located near each other and without disrupting the game play. In another case, a player may be registered to multiple RDCs, but wants to associate with one RDC at any given time.

In addition to an RDC granting permission to the PDK for access, the RDC may also dictate to the PDK the number of simultaneous associations allowed. The purpose of defining the number of associations permitted may reduce the possibilities that the PDK can simultaneously associate with and enable two or more RDCs within close proximity of each other. This may prevent unauthorized use of a player's PDK on adjacent enabled devices, thereby disallowing a player from using another player's identity. The capability of configuring the number of associations for a particular RDC may be implemented in a system stack and controlled by the attached controller's application.

Referring again to the case where a player desires simultaneous access to a game and another device, a PDK may be capable of associating to multiple RDCs based on the physical limitation of the maximum number of simultaneous connections the PDK can handle and based on the number of associations the RDC permits.

Further, it is noted that under the conditions the PDK is associated with more than one RDC, the PDK may relay information back to each RDC indicating its timing relative to the other RDC. This information may be important in the event a single PDK is associated with more than one RDC because the clock frequency error between the RDCs may cause eventual timing drift that will eventually cause timeslot and superframe overlap and prevent the PDK from communicating with both units on a periodic basis. This situation is also noted: where two PDKs are associated with the same RDC and each PDK is also associated with a different second RDC. Additionally, each of the second RDCs may also have other PDKs associated with them that are also associated with even different RDCs. Eventually, such an uncoordinated system may appearing like a mesh network. A system of such complexity may require a CRDC to be used to address synchronization issues.

As to the case where a player may be registered to multiple RDCs, but wants to associate with one RDC at any given time, there may one or more techniques that may be employed to control how a PDK associates with a specific RDC. In one way, a PDK is associated with a single RDC. Using this technique, the PDK may attempt to associate to other RDCs, but the other RDCs will deny association through the back-end central server, causing the PDK to ignore the other RDCs as previously described above. It is noted that such a technique may eliminate a cell size issue, where the cell must be constrained to prevent other RDCs the PDK is registered to from accessing the PDK.

In another technique for directing a PDK to communicate to one RDC in a configuration where multiple RDCs exist of which the PDK is registered to, by significantly reducing the RF power level from the RDC and providing this information along with a request for the PDK to reduce its RF power, a close proximity communications channel may be created. The close proximity communications channel may then operate as if a single cell network exists. More particularly, if the RDC is configured to have a reduced RF power output, the RDC's cell boundary shrinks causing the PDK to have to be within closer proximity of the RDC to receive a beacon from that RDC. If, in turn, the RDC indicates in the beacon that it is at reduced RF power, the PDK is aware that the RDC is in extremely close proximity. In addition, if the beacon includes a command to instruct the PDK to reduce RF power, the chance of surrounding RDCs receiving a response or interference from the PDK may be minimized. When the communications channel is terminated and the PDK no longer sees the beacon from that RDC, the PDK may readjust its RF power level to normal levels for a larger cell coverage area. Such dynamic RF power level adjustment may be implemented in the system stack.

Thus, in one or more embodiments, there exists a scheme to dynamically adjust a transmission power and/or reception sensitivity of a wireless reader device along with an ability to command a client device to do likewise to permit both cell coverage and client device response area programmability. This may enable the dynamic tracking of transient client devices within and through the cell's extended or default coverage area with full power and sensitivity at both ends, while concurrently allowing the association of a particular client device in close proximity to the reader device for command and control of an application or service during a session. Those skilled in the art will note that by dynamically varying a size of a cell in which a secure transaction takes place between a PDK and an RDC (or in which a PDK accesses an application via an RDC), at least some level of security may be achieved in that eavesdropping may be prevented. Moreover, unnecessary and potentially unsafe propagation of a wireless signals beyond a certain distance may be avoided.

For example, a plurality of PDKs may be located in a default wireless coverage range of an RDC. This default wireless coverage range may represent a cell of the RDC at full power. As the plurality of PDKs enter and exit the RDC's cell, the RDC reports corresponding location tracking information back to, for example, a central server. When one of the PDKs requests access to an application secured by the RDC, the RDC may follow by reducing its RF power and commanding the requesting PDK to also lower its RF power, thereby in effect requiring that the requesting PDK be "drawn in" to the RDC in order for the PDK to access the application. It is noted that while the RDC may communicate with the requesting PDK via low power RF signals, the RDC may continue to maintain its default wireless coverage range for tracking other PDKs. When the requesting PDK is moved away from the RDC or the session is otherwise terminated, both ends return to their default full RF power settings.

As described above, reception sensitivity of the RDC and/or PDK may be changed as part of a cell size variation technique in accordance with one or more embodiments. Reception sensitivity may be adjusted using an RF attenuator (e.g., a step, variable, or programmable RF attenuator) that is either specific to a receive path or common to both receive and transmit paths. It is noted that even if the attenuator is common to both receive and transmit paths, transmit power may be independently controlled. Further, in one or more embodiments, a separate attenuator may be used to allow for independent control of transmission power and reception sensitivity.

To determine how much to adjust the size of a wireless cell without severing a wireless connection between an RDC and a PDK, one or more of various metrics may be used. For example, in one or more embodiments, a signal strength of the PDK may be monitored to determine by how much to power down a transmission power of the RDC and/or the PDK. If the signal strength is determined to be relatively strong, then the RDC may cause a reduction in transmission power that is greater than if the signal strength were detected as being weak. Conversely, if the signal strength is detected as being weak, the RDC may lower transmission power by a small amount or not at all. Instead of or in addition to relying on signal strength, a bit error rate may be assessed to determine by how much to power down the transmission power. For example, if the bit error rate of communications between the RDC and PDK is determined to be low, then the RDC may lower transmission power by an amount greater than if the bit error rate was determined to be relatively high.

Further, as described above, the transmission power and/or reception sensitivity of either or both of an RDC and a PDK may be adjusted. In one or more embodiments, only a transmission power of the PDK may be adjusted. This may done to, for example, "bring in" the PDK and reduce the likelihood of that PDK interfering with other RDCs. In one or more other embodiments, the transmission power of both the RDC and the PDK may be adjusted in an effort to draw in the PDK to the RDC. In still one or more other embodiments, in addition to or instead of adjusting transmission power, reception sensitivity of either or both of the RDC and the PDK may be changed.

Moreover, in one or more embodiments, an RDC may have multiple wireless transceivers, whereby at least one of the transceivers is at full power for PDK location tracking purposes, while one or more of the other transceivers are used to establish adjustable wireless cells for particular associations with PDKs. For example, in the case of an ATM machine having an RDC, the RDC may carry out a secure transaction with a PDK in an adjusted wireless cell, while at the same time, casting a broader wireless cell to monitor and identify one or more PDKs around the transacting PDK. In such a manner, for example, a security measure may be implemented by which the RDC can identify individuals behind a transacting user. Further, as an added or alternative security measure, transmission power may be adjusted dependent on a sensitivity of the type of data requested to be exchanged in a particular transaction. Such data sensitive transactions may be conducted at low power with additional security measures such as password entry or biometric input.

Application Utilizing Multi-Cell Coordination

Figure 31:
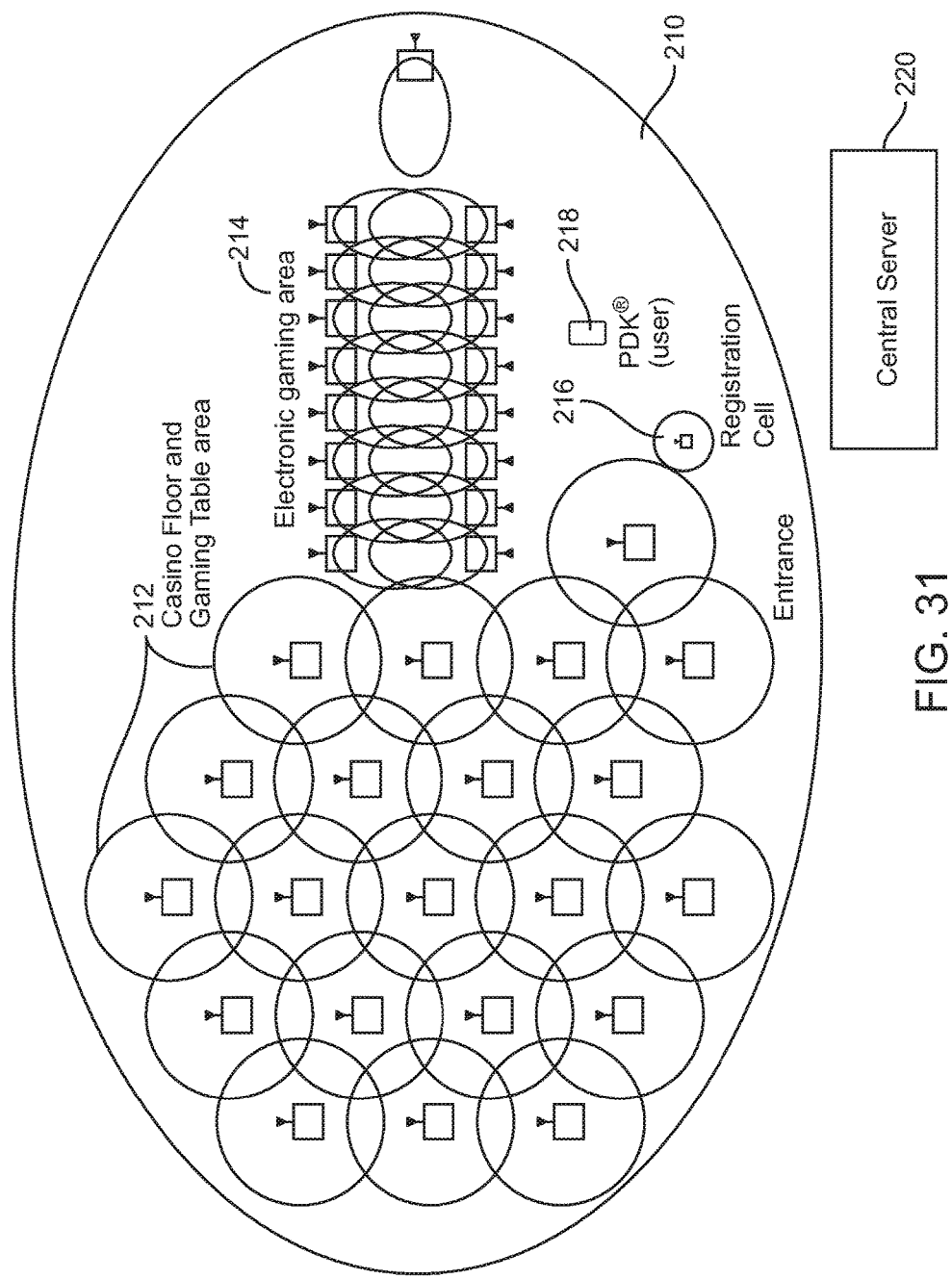
FIG. 31 shows a floor layout and cell distribution in accordance with one or more embodiments of the present invention.

The following describes a system architecture and operation of a system within, for example, a casino application. Referring to FIG. 31, a CRDC (not shown) and multiple RDCs (shown, but not individually labeled) are distributed throughout a casino floor. In such embodiments, a single CRDC generates a cell 210 that provides ubiquitous coverage of the entire floor. On the left side of FIG. 31, multiple RDCs (shown, but not labeled) provide overlapping cell coverage and blanket the casino floor and gaming table area 212 all the way to an entrance of the casino with continuous wireless service coverage. These RDCs may be dedicated to PDK location tracking, allowing the casino operator to know where a player carrying his/her PDK is geographically located on the floor. These RDCs may be mounted in the floor or ceiling, creating, for example, relatively symmetrical cells.

Another set of RDC cells (shown, but not labeled) are shown to exist in the right side of FIG. 31 and are integrated in gaming machines (shown, but not labeled) within an electronic gaming area 214. The cell orientation for these RDCs is more oblong and focused at players that are within close proximity and in front of the electronic gaming machines, noting that cell orientation and shape may be set according to antenna position and/or configuration. The cells extend outward towards the center of the isle to detect the presence of a player that may be walking by. Toward the lower right part of FIG. 31 is a registration cell 216 that sits at a registration desk (shown, but not labeled) where a player may register and acquire a PDK the first time the player enters the casino. The registration cell 216 may be smaller in size to enable local communications between the RDC and PDK without allowing external RF monitoring devices to capture and record the interaction between the devices.

It is noted that in FIG. 31, a PDK 218 that is currently out of the range of all RDCs, but still in range of the CRDC. This represents a PDK carried by a player, which is being used to track the player's position and provide additional services. Such services are further described below.

Further, still referring to FIG. 31, there is a central server 220. The central server 220 may contain a player's financial information (credit card numbers, gambling limits, and other information related to a player). In addition, the central server 220 may be physically wired (not shown) to all RDCs and/or CRDCs located throughout the casino.

Although not shown in FIG. 31, within the PDK location tracking system, RDCs may be gambling tables that also have RDCs embedded within the table itself. A representative gambling table is shown in FIG. 32.

Figure 32:
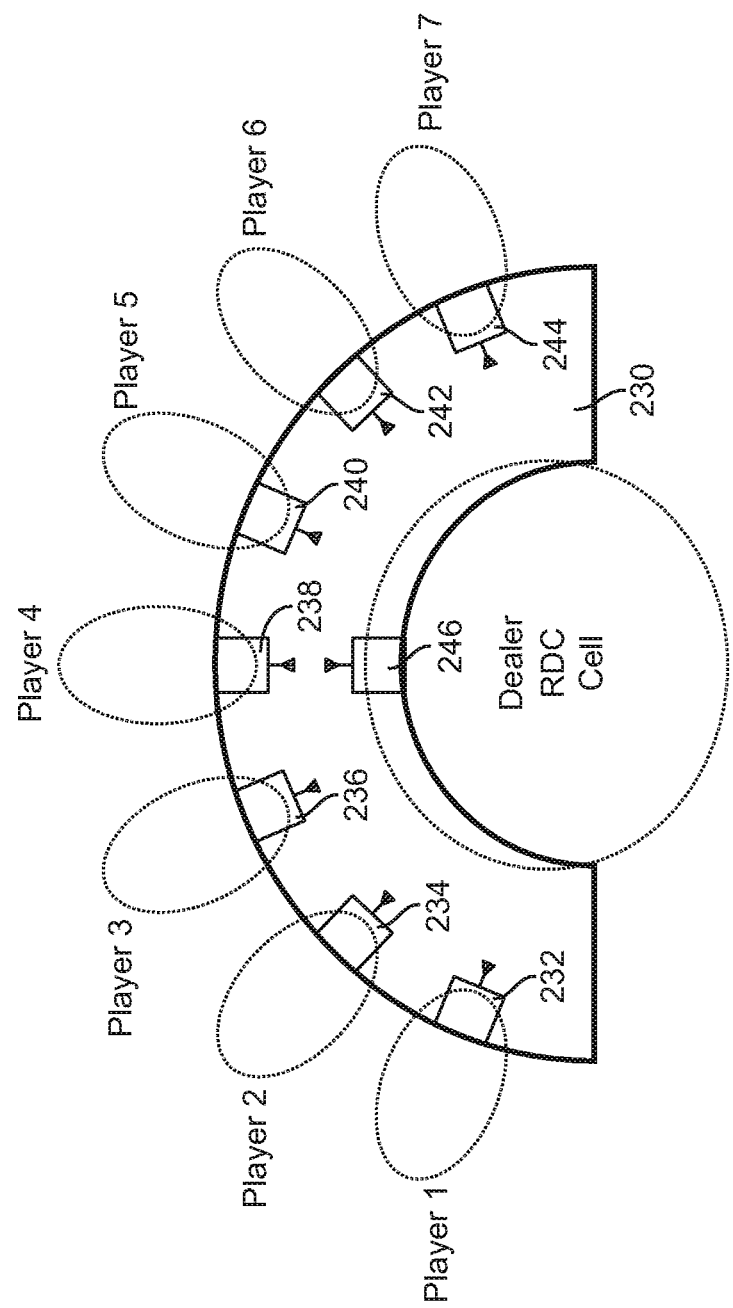
FIG. 32 shows a gambling table with RDCs in accordance with one or more embodiments of the present invention.

As shown in FIG. 32, a gambling table 230 has RDCs 232, 234, 236, 238, 240, 242, 244, 246 embedded within it. RDC 246 may be a dealer RDC that has a cell geometry covering the dealer's area, allowing the dealer to freely move around in this area. There are an additional RDCs 232, 234, 236, 238, 240, 242, 244 that are located at each player position. Each of these RDC cell's coverage areas are oblong and are directed to where the player would be sitting/standing. It is noted that each player position's RDC 232, 234, 236, 238, 240, 242, 244 allows for some coverage of the region directly behind each player position, allowing the RDC 232, 234, 236, 238, 240, 242, 244 to report back through the system the presence and identity of anyone behind the player. The RDC cell's coverage areas may be minimized to cover the area where a dealer or player may be located relative to the table. Those skilled in the art will note that the actual cell footprints may vary from those shown in FIG. 32. Utilizing distributed RDCs with directional, highly attenuated, antennas allows the casino operator to know the location of both dealers and players, and the amount of time they remained at the table.

Figure 33:
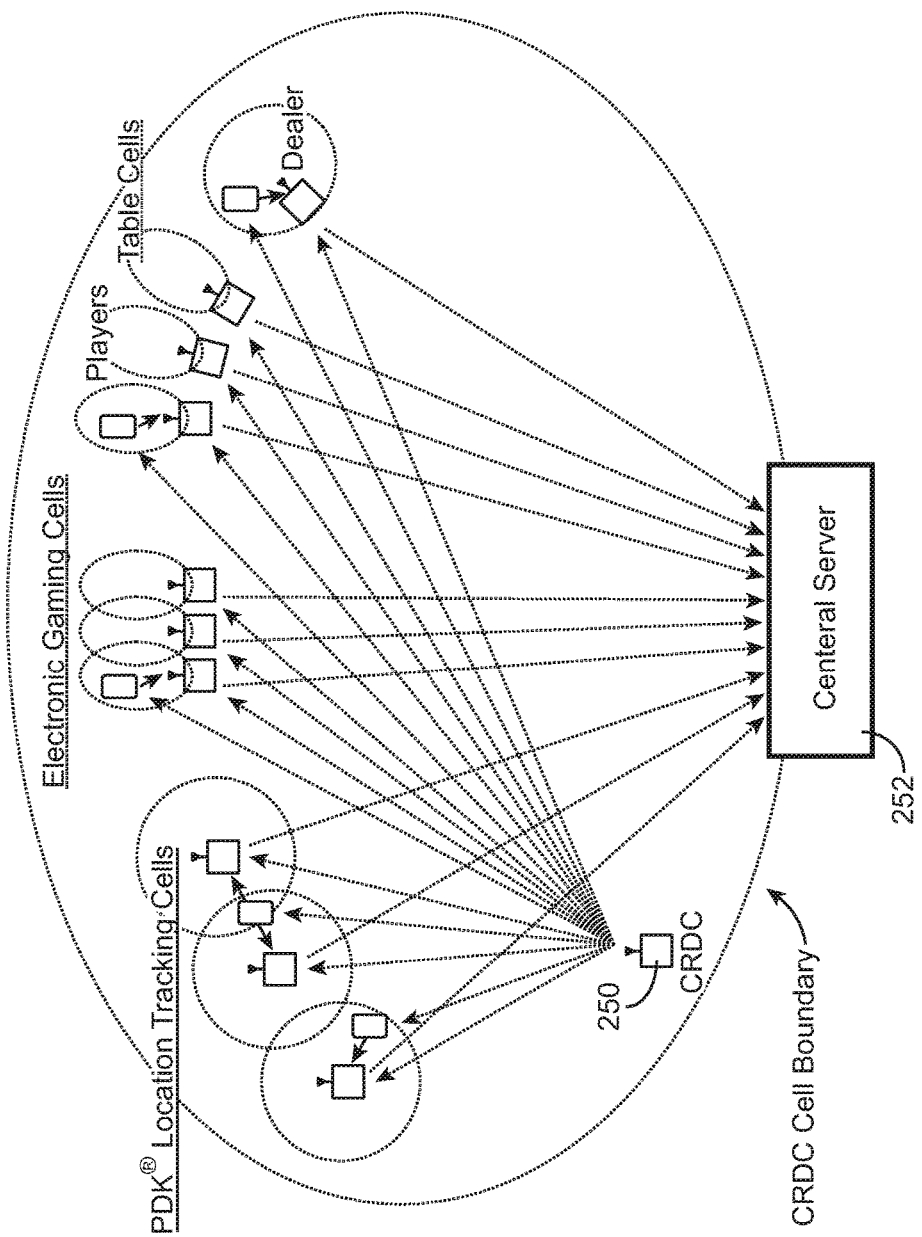
FIG. 33 shows a CRDC beacon to central server flow in accordance with one or more embodiments of the present invention.

The CRDC, PDK location tracking RDCs, and gambling table RDCs, may interoperate in a system such as that shown in FIG. 33. FIG. 33 shows a graphical representation of the sequence of events that may occur when a c-beacon is transmitted in, for example, a casino application. As shown in FIG. 33, first, a CRDC 250 transmits the c-beacon to all RDCs and PDKs (shown, but not labeled) within the CRDC's cell radius. All of the RDCs and PDKs setup and synchronize their timing to the beacon. Next, each PDK, in its appropriate timeslot, transmits a PDK location response ID. Any RDC that is in the vicinity of the PDK's response receives the PDK location response ID and logs specific information related to the reception. Then, each RDC packetizes the information received from the PDK and, through a wired back channel, relays the information to a central server 252. The central server 252 may then utilize this information to indicate to an operator, by either graphical or text format, the geographic location of each player.

Figure 34:
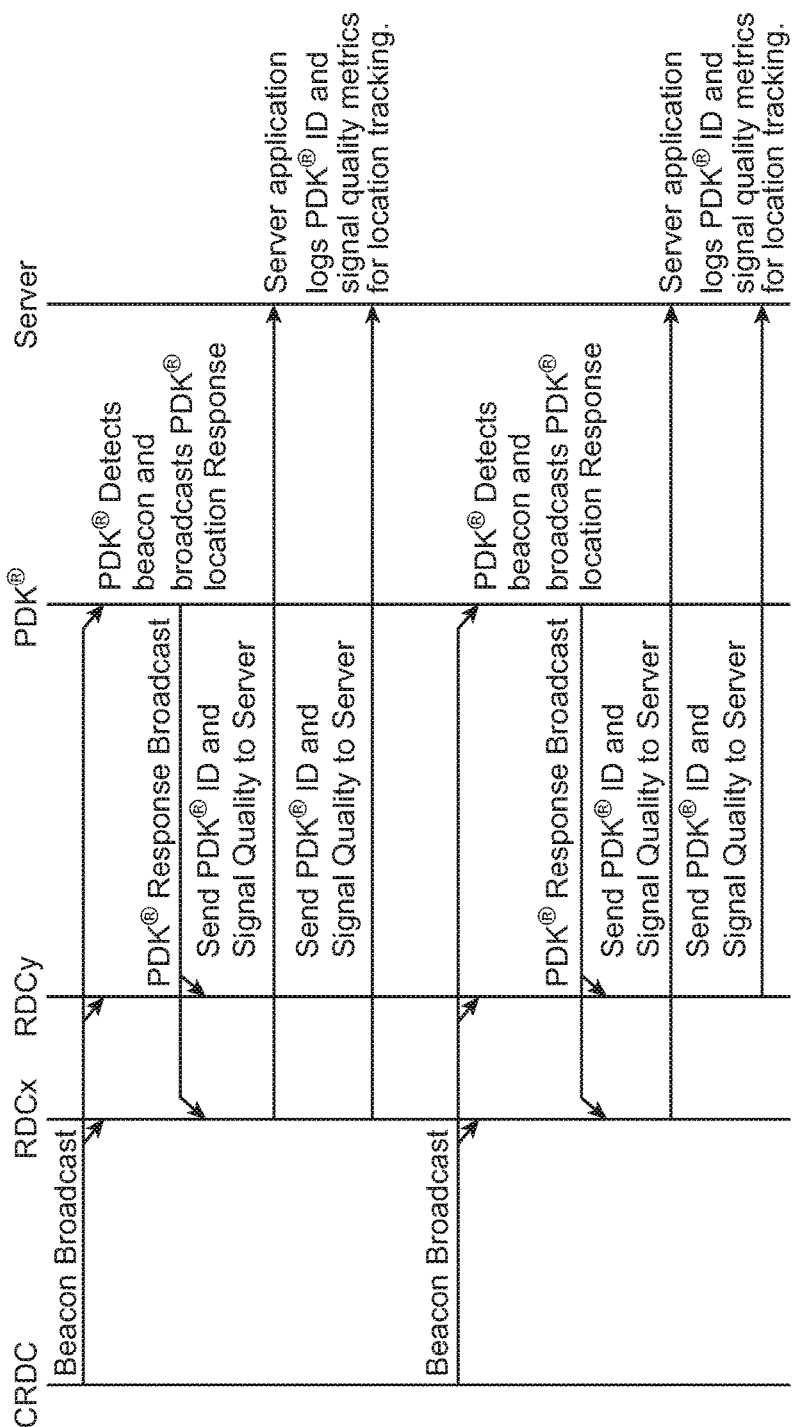
FIG. 34 shows a CRDC beacon to central server handshake in accordance with one or more embodiments of the present invention.

Representing the flow in a different manner, the interactions for a single PDK is shown in FIG. 34. In addition to providing location tracking information, when the PDK outputs a PDK location response ID, certain events may occur from an RDC based device. In the event the RDC based device is an electronic game, via the central server, the electronic game may entice the player over to it by flashing information on the screen related to that specific player. In one example, an electronic gaming machine may offer the player a free game, gaining the player's attention and ultimately enticing the player to play the game. In order to identify the player, further steps may be taken between the PDK and the RDC that are described below.

In the event the RDC device is used for location tracking, it may perform further interrogation of the PDK to determine whether the PDK is legitimate. A more detailed description of such interrogation is provided below.

Figure 35:
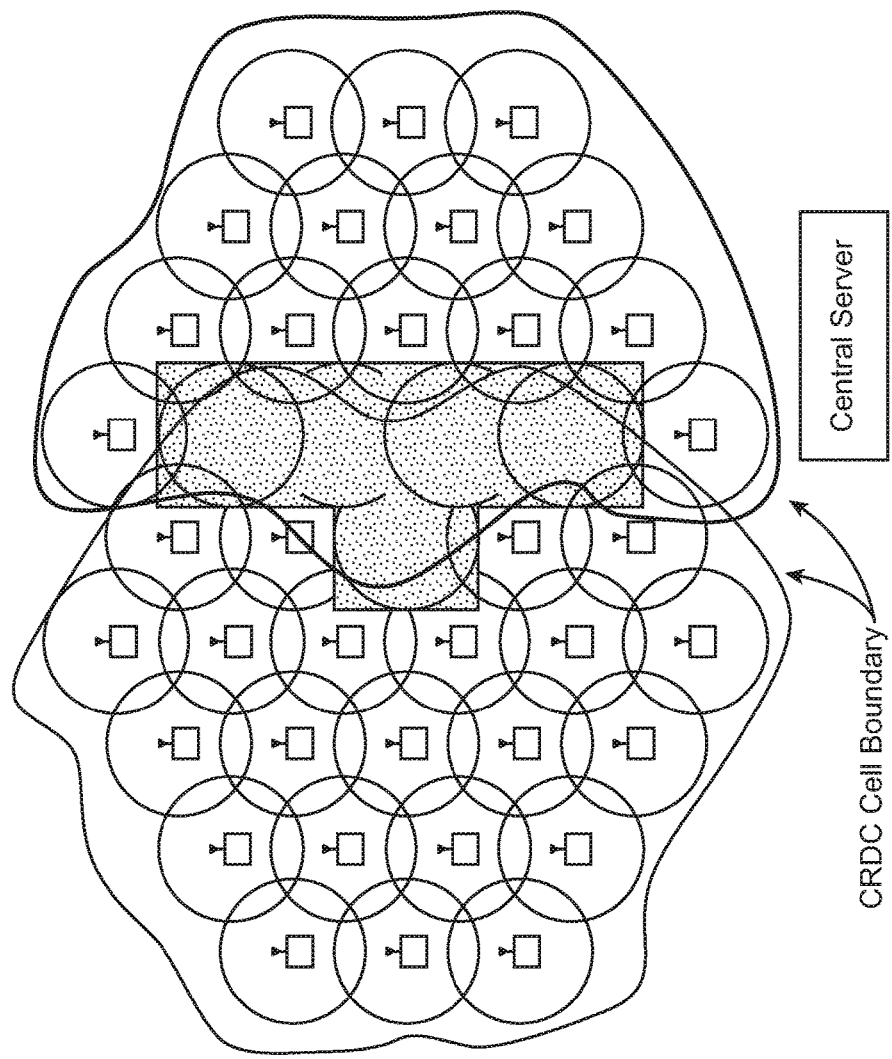
FIG. 35 shows a configuration of overlapping CRDC cells in accordance with one or more embodiments of the present invention.

Now referring to FIG. 35, it shows two CRDCs with overlapping cell coverage, but not to the point where each CRDC can see the other CRDC. As shown in FIG. 35, the CRDC cells are non-uniform in nature due to obstructions blocking the transmit radio path. The CRDC cell overlap may cause a number of RDCs to be in each CRDC cell. It is envisioned that other CRDCs may overlap in the same region if they are placed above and below the RDC microcellular structure. In this case, for example, up to 4 channels may be occupied just for CRDC beacon transmission.

Due to the possibility of interferers in the coverage area of the CRDC, the central server may manually configure the CRDC, or the central server may also instead or additionally have the capability to auto-configure. In the case the central server performs manual configuration, upon initial installation, power up, and provisioning, the CRDC is configured to remain in a dormant state until the central server interacts with the device and instructs it to perform specific tasks. The central server may first instruct the CRDC to enable the receiver, scan all channels, and report back the findings of each channel. When the CRDC scans each channel, it collects signal quality metrics and any IEEE 802.15.4 radio transmissions. The operator of the central server may then analyze all of the signal quality metric information and any IEEE 802.15.4 framing information to determine the best channel the CRDC should transmit its beacon on. Once determined, the operator at the central server may command the CRDC to store the specific channel that it will transmit on and enable it to begin transmitting. The operator may then select the next CRDC and perform the same operations, until all CRDCs have been configured in the network.

In an automatic configuration mode, the CRDC scans each channel and collects signal quality metrics and determines if other IEEE 802.15.4 devices (including another CRDC) are present. The CRDC may then select the quietest channel to begin its beacon transmission on. Further, it is noted that it may be recommend that initial auto-configuration of a CRDC occur when there is a single CRDC present. This recommendation is based on the fact that the CRDC may have overlapping coverage with another CRDC as shown in FIG. 35, but the CRDC is not aware of the overlap, causing two CRDCs to transmit their beacons on the same channel. Eventually, due to potential timing inaccuracies in the CRDCs, they may overlap and become direct interferers to RDCs and PDKs in the overlapping area. An exception to this recommendation is when the system is configured to allow the CRDC to report back the channel that it occupies (or intends to occupy) to the central server, and the server can then analyze the CRDC channel lineup on all CRDCs and reassign a channel for any given CRDC.

Once a channel has been assigned and stored in a local non-volatile memory of the CRDC, upon next power up, the CRDC scans all channels again and return to their last assigned channel provided that it is not occupied by an interferer or by another CRDC beacon. In such a case, the CRDC may have to again go through the initialization process.

Although a synchronized system may lead to higher throughput and may possibly lead to better battery life, in one or more embodiments, it may not be necessary for CRDCs to be synchronized. Because each CRDC operates on a separate channel, there may be no timing-specific consideration that needs to be addressed between CRDCs. Instead, a concern may relate to how the PDK aligns to multiple unsynchronized CRDCs. From a PDK location-tracking standpoint, the PDK may be required to lock to a single CRDC beacon. The CRDC beacon will indicate to PDKs what other channels a CRDC may be located on. The PDK may not need to attempt receiving from any other CRDC, provided the signal quality metrics for the current CRDC it is monitoring has sufficient signal quality to receive error free data. In the case the signal quality degrades, the PDK may then periodically switch to other channel(s) to determine if a better signal quality can be obtained. If a better signal quality is determined to be on an alternate channel, the PDK may then immediately switch to the alternate channel, provided it is not in association with an RDC at that instance in time. If the PDK has begun association to an RDC, the PDK may have to attempt to finish the association before switching to the alternate channel. It is noted that once a PDK is in association with a RDC, the PDK is no longer required to monitor the CRDC beacon, until the association ends between the devices by releasing the link or by the PDK leaving the RDC cell.

When an RDC is powered up for the first time, the RDC may not be aware of the network it belongs to or its configuration within the network. The RDC may default to a single cell configuration. For this reason, RDCs placed in a CRDC cell configuration may by default remain in a dormant state upon its first initial power up in the network. This may allow the central server to configure any specific information related to the network into the RDC prior to operation. Some of this information may include, for example, the site ID, a local RDC ID, and other parameters related to the wireless transmission protocol. The site ID is important, because the property owner may not want their RDCs to become associated with another property; thus, the RDC should synchronize to beacons transmitted with that site's ID. The RDC ID is used in communication between a PDK and RDC; hence, there should be one RDC ID per RDC device in the network. Other application-dependent parameters may include how the unit operates when associated with a PDK and whether the RDC sends data back to the server when data is ready, or if the server must poll the RDC for the information. The central server may then command the RDC to enable its receiver and scan all channels to determine the signal quality of each channel and which CRDCs may be received by the RDC. The operator of the central server may allow the RDC to automatically select which CRDC Beacon to lock to, or can command the RDC to select a specific CRDC beacon. After reviewing the channel list for signal quality, the system may then command which channels the RDC can use for alternate channels for RDC-PDK communications, or the system may command the RDC to automatically select the alternate channels. The system may then place the RDC in operation mode, and the RDC then tunes to the selected CRDC beacon channel and remains there listening for CRDC beacons and any PDK that sends a PDK location response ID. While receiving the c-beacon, the RDC may configure its timeslot information similar to that described above. This defines the superframe structure as well as defining which timeslots (odd or even) the RDC is permitted to communicate with a PDK on the beacon channel.

In the background, on the alternate wireless link described above with reference to FIG. 9, the RDC may continue to scan the alternate channels, updating its list of clear channels. This updated list may then be used when a RDC determines it wants to extend its communication with a PDK in association mode and selects which channel that communication will occur on. The RDC, in operational mode, may perform frame and slot alignment to the CRDC and listen for a PDK location tracking response. On a periodic basis, the RDC may send information back to the central server indicating that it is still operational and indicating the status of the communications channels (e.g., CRDC beacon, alternate channels).

In one or more embodiments, a registration RDC may be used to initially enable and to configure a PDK. The registration RDC may have a small cell coverage area by design, measured, for example, in inches. This may require that the unregistered PDK must be in extremely close proximity, e.g., placed on the registration RDC housing, to communicate with the registration RDC, reducing the likelihood of RF eavesdroppers gaining access to PDK setup information.

The registration RDC may be directly connected to a central server. In addition to specific security features, the registration RDC installs and configures service provider information located on the central server (described above with reference to FIGS. 6 and 7). Such information may include the service provider ID, secret key, and other parameters that the service provider wants to designate for access within their network. These other parameters may vary in size in the PDK and may be defined by the host system to meet the needs of the property. Information transferred to a PDK may include, for example, the service provider site ID, the service provider's assigned PDK ID, the service provider's secret service ID, the service provider's secret key, and service provider specific access information.

Now describing an example of an operation in accordance with one or more embodiments, once a system has been installed and properly provisioned, a rated player may walk into the casino. They are greeted by a host and walked over to the registration desk, where the player's information, already in the central server, is linked to a PDK that is given to the player and assigned with specific privileges. The player places the PDK in their pocket and begins to walk throughout the casino. Once the PDK leaves the registration cell, the PDK enters discovery mode and scans the channels for a c-Beacon. If the PDK does not locate the c-beacon, it continues to scan for an undetermined period of time until it either goes into battery save mode or finds a c-beacon.

Once the PDK finds a c-Beacon, the PDK determines if the c-beacon is a particular type of network and the site ID is in its local service provider database. If the site ID is not in the database, the PDK ignores that c-beacon and keeps looking for other c-beacons on other channels until one is found that is in its local database. Once a valid c-beacon containing a site ID that is in the PDK's local database is found, the PDK extracts the CRDC channel availability flags and checks the other channels in the CRDC channel availability list. The PDK then determines which CRDC has the best signal quality metrics. The PDK switches to that channel and begins receiving c-beacons. The PDK extracts the CRDC and network configuration information as described above. This information may define the framing structure and how the PDK should operate within the network. The PDK then applies the c-beacon parameters to its radio transceiver parameters, configuring the sleep interval and response superframe and timeslot information. Because the PDK has just received a c-beacon, the PDK is now aware of the current superframe count. The PDK then configures its timer to wake up just prior to the expected superframe count that it may communicate on.

Figure 36:
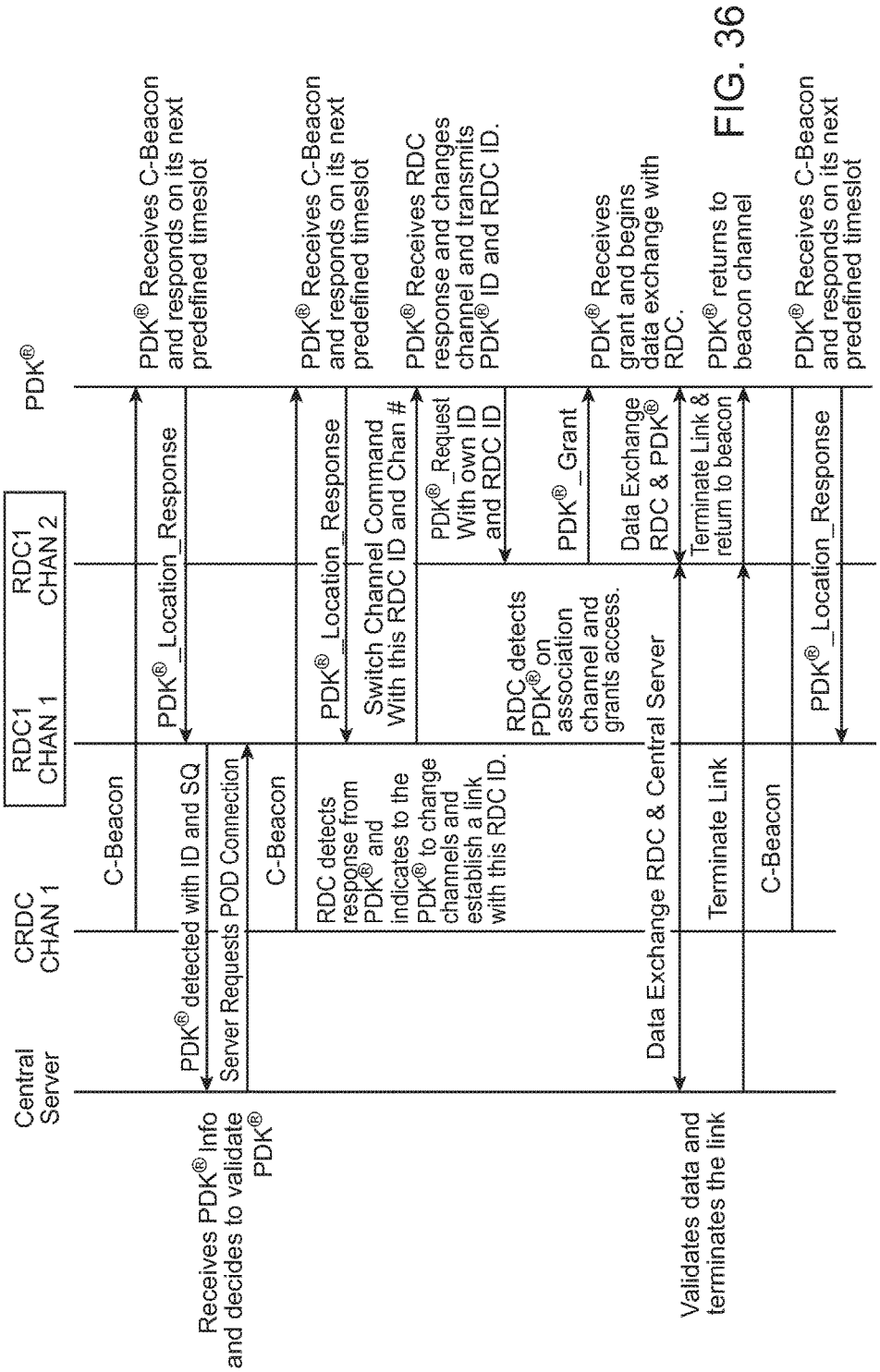
FIG. 36 shows a c-beacon handoff for RDC-PDK communication in accordance with one or more embodiments of the present invention.

Now also referring to FIG. 36, when the sleep timer expires, the PDK may wake up, listen for a specific c-beacon, and verify the superframe count. It then waits a predetermined period of time for its slot to be available and performs CSMA-CA, and if no other device is attempting to respond, it responds with its PDK location tracking response. If another device was detected on the channel, the PDK may then reset its timers and wait for the next predefined superframe and timeslot to wake up and attempt again.

It is noted that a PDK in accordance with one or more embodiments may be powered by an internal battery of, for example, a type commonly used to power small electronic devices such as watches, calculators, and mobile computing devices. The power of such a client device battery is consumed when the PDK is active. In an effort to reduce and/or minimize battery consumption, in one or more embodiments, the active time of a PDK as a percentage of total time may be reduced by management of transmission and reception times. For example, as described above, a network in accordance with one or more embodiments may be designed to configure time slots (e.g., frames), groups of time slots (e.g., superframes), and/or coordinating beacon superframes (e.g., c-superframes) in a manner such that a client device is caused to both listen and respond within specific time slots. Because these time slots are configured by the network, they may be precisely predicted, thereby allowing the client device to set a timer, return to sleep mode, and waken when a specific, time-slotted interaction is expected or required of the client device. Further, in one or more embodiments, because a network in accordance with one or more embodiments may implement programmable c-superframe lengths, an operator or system may individually tailor performance to maximize (or at least improve) battery life and/or minimize (or at least reduce) system inter-message latency without requiring access of the client device itself or physical alteration of the client device.

When the PDK responds with a PDK location tracking response, every RDC within local proximity that can receive the response may log the response message in its database along with signal quality metrics and a timestamp. They will then send the information back to the central server. The response may be sent by the server polling the RDC or by the RDC if it has data to send. Once the central server receives the PDK information from one or multiple RDCs, the server may then determine if any further communication with the PDK is necessary. If, for example, the system wants to validate the PDK, it can perform a validation. The server may then send a command to a specific RDC to set up communications with a specific PDK and wait for a response from that RDC. Because the communication between the RDC and the central server may not be instantaneous, the RDC may have to wait for the next PDK location tracking response. After performing CSMA-CA, it may immediately instruct the PDK to switch to the alternate channel. If, during the CSMA-CA, the RDC detected another device on the channel, the RDC may wait for the next PDK location tracking response from that PDK and then re-attempt PDK channel reassignment. The PDK may then switch to the alternate channel, perform CSMA-CA, and send a link request to that specific RDC ID with its own ID included. The RDC, looking for the link request with its specific ID and a particular PDK ID, detects the request and then responds with a link grant. Further, the RDC may alert the central server of the link, and a data exchange occurs with information the server is interested in collecting by interrogating that PDK. After the data exchange occurs, the central server commands the RDC to terminate the link. The RDC may then terminate the link, and the PDK may returns to the c-Beacon channel, re-synchronizing to the beacon, and begin monitoring for its timeslot. The PDK may then continue to send responses back to all RDCs in its immediate vicinity when its specific superframe count and timeslot are valid.

It is noted that the foregoing description detailing a process of PDK validation and interrogation relates to one or more embodiments. However, in one or more other embodiments, the central server may have also altered the service provider information within the PDK.

If, during the switch to the alternate channel for RDC to PDK communications, the PDK determines the channel is occupied or the PDK does not receive a link grant back from the RDC, the PDK may perform one or more additional attempts. If after all attempts, the PDK does not receive a response from an RDC, that PDK may return to the c-beacon channel, realign to the beacon, and then begin sending its PDK location tracking ID.

If the RDC was unable to receive the link request from the PDK on the alternate channel, for a predefined period of time, the RDC may flag the error and continue listening on the channel. If the same RDC is again instructed to establish communications with the same PDK, the RDC may choose to use a different alternate channel and redirect the PDK to the new alternate channel for communications.

Figure 37:
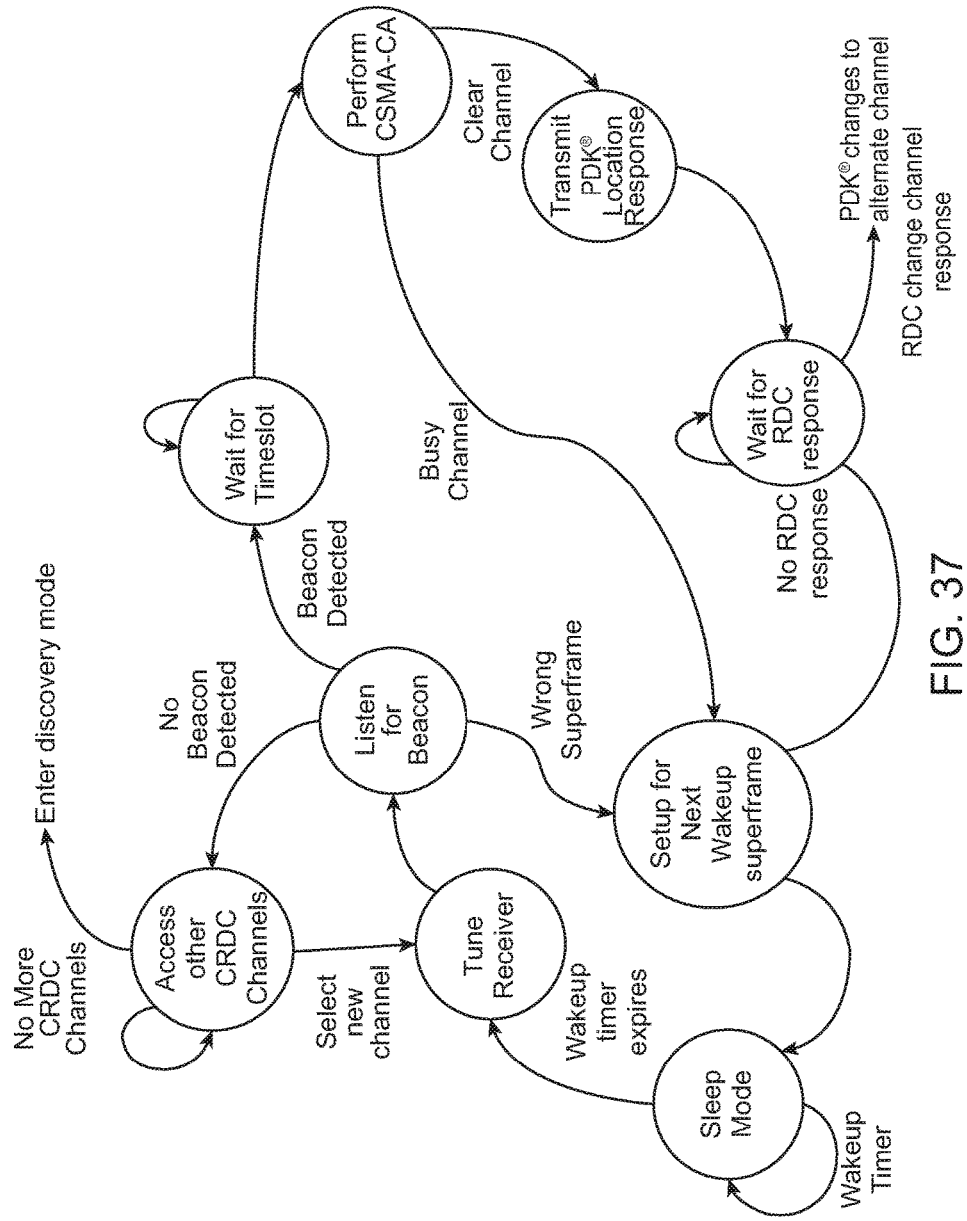
FIG. 37 shows a PDK wakeup and response state flow in accordance with one or more embodiments of the present invention.

Now referring to FIG. 37, it shows a PDK wakeup and response flow in a CRDC coordinated system. For purposes of describing FIG. 37, it is assumed that the PDK has acquired system synchronization and has gone into the sleep mode after setting its timers to wake up on the next predefined superframe. The PDK remains in sleep mode until the wakeup timer expires and wakes up the PDK. The PDK then enables and tunes its receiver to the c-beacon channel and listens for the beacon for a predefined period of time. If no beacon is detected, the PDK checks for other CRDC channel available flags in its local memory. It then reassesses signal quality and beacons on the alternate CRDC channels.

After the PDK assesses the other CRDC channels and no beacon is found, the PDK goes back into rediscovery mode scanning all channels looking for a c-beacon. If no c-Beacon is found, the PDK then starts its deep sleep mode. In the event that other CRDC channels are present, the PDK assesses the signal quality of each channel and selects the best channel. The PDK then selects that channel and tunes to it listening for the CRDC beacon.

When the PDK receives the beacon, it checks all of the parameters associated with it including the superframe count. If the PDK determines the superframe count is not the correct one for it to wake up and respond on, it sets its internal sleep timer to wake up just before the next expected superframe it should respond to and returns to sleep mode. If the PDK determines that the beacon is on the PDK's expected superframe count, the PDK then stays awake, but stops listening until just before its expected timeslot. The PDK may then perform CSMA-CA to determine if the channel is busy. If the PDK determines the channel is busy, the PDK may again set its internal sleep timer for the next expected superframe and return to the sleep mode.

If the PDK finds the channel to be available, the PDK then transmits its location tracking response and waits for one additional timeslot for a response from an RDC. If the PDK receives a response from an RDC, it then performs the command sent by the RDC (e.g., to switch to the alternate communications channel). If the PDK does not receive a response from an RDC, the PDK may again set its internal sleep timer to wake up just before the next expected superframe it should respond to and then return to sleep mode.

As described above with reference to FIG. 31, in one or more embodiments, an RDC may be located within an electronic game on an electronic gaming floor. Each game may have an integrated dual wireless link RDC, such as that described above with reference to FIG. 9. The RDC may be used for PDK location tracking and PDK association. There are various approaches in integrating an RDC into an electronic game or other equipment housing. In one approach, shown in FIG. 38, the integration of the RDC is from a physical perspective; no electrical connections exist between the RDC and the game. In this configuration, the RDC and electronic game need not even reside within the same enclosure; they coexist as two physically close, but separate, devices. They may not be connected in any way other than physical proximity. The purpose of placing them in close physical proximity is to allow the RDC to perform proximity detection for any player carrying a PDK that may be positioned near the front of the machine. In this configuration, each device (RDC and electronic game) may have separate connections to a central server (or an external data concentrator) used to connect both devices to a single wired connection back to the server. It is noted that the game may operate autonomously, with the possible exception of responses to any commands sent to it by the server. In this case, the RDC may provide both proximity detection and association with PDKs.

Figure 39:
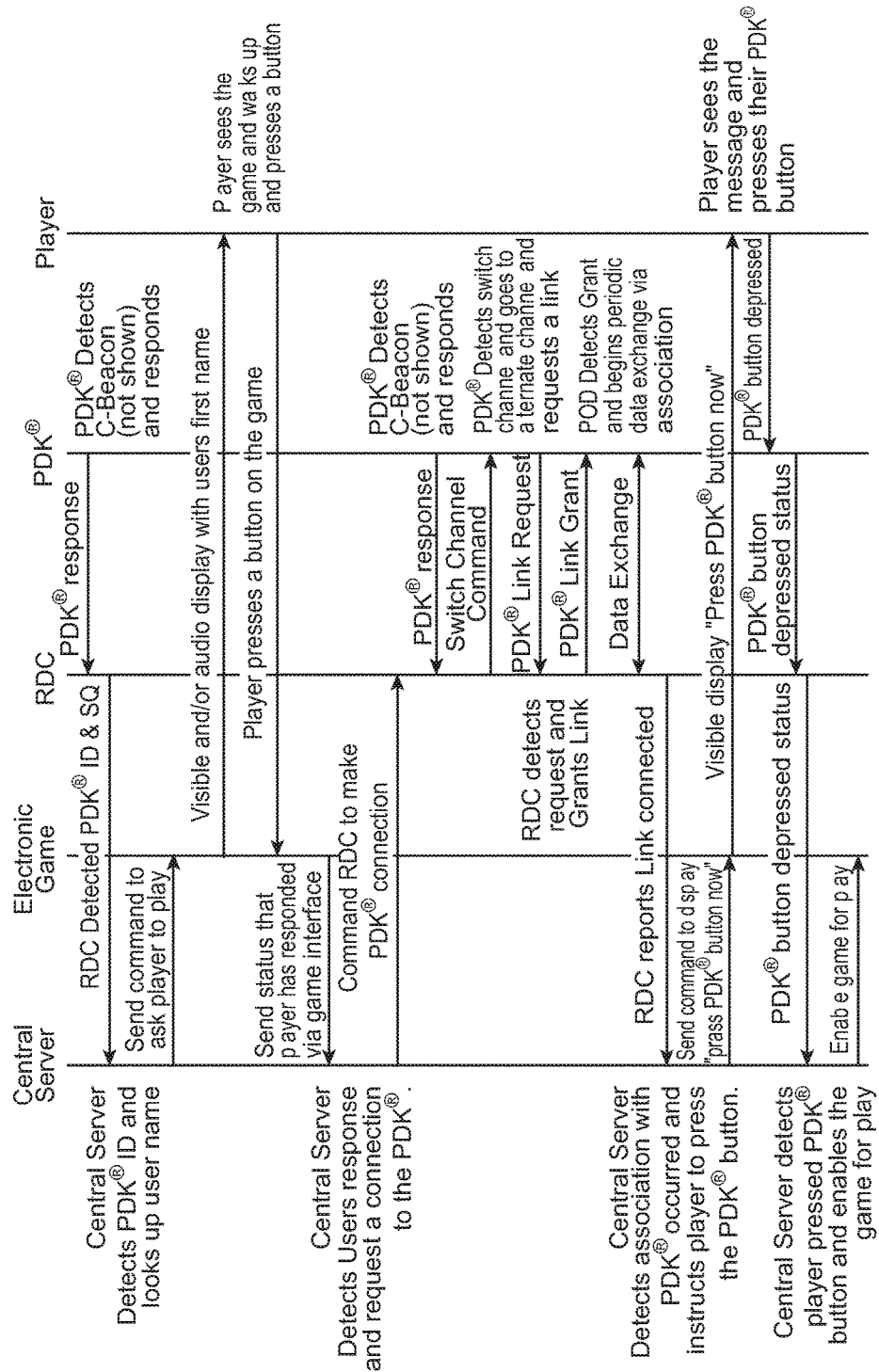
FIG. 39 shows an electronic game player tracking and game enable handshake in accordance with one or more embodiments of the present invention.

Now also referring to FIG. 39, it shows an example of a handshake that may take place from the time a player carrying a PDK is detected to the time the game is enabled for that player. For purposes of clarity, the CRDC is not shown in FIG. 39. The handshake starts by the PDK detecting a c-beacon. Each time the c-beacon is detected on the expected superframe and timeslot, the PDK may send out a PDK location tracking response.

The RDC near the game detects the response and sends the PDK's information back to the central server. The server realizes the user is close to the game and may send a command back to the game instructing it to display a message for the player in an effort to entice the player to play. In this example, the player may see the message and sit down at the game and press a button to commence play. In turn, the game sends a message back to the server indicating that the button has been pressed. The server then requests the RDC to make a connection with the player's PDK. Upon the next c-beacon, the player's PDK responds and the RDC receives the response. The RDC then transmits back to the PDK to change to another channel for association mode to begin. It is noted that up until this time, the PDK was in tracking mode. The PDK then switches to the alternate channel indicated by the RDC and sends out a PDK link request with both the PDK ID and the RDC ID. The RDC detects the request and sends back a PDK link grant. The PDK and the RDC then exchange secure information to establish trust, prior to establishing a secure link for validation of the PDK. The RDC may also lower its RF power and instruct the PDK to lower its RF power in order to enforce close proximity Periodic data exchange may continue to between the RDC and PDK.

After the secure link is established, the RDC may report back to the central server that the link is established between the RDC and PDK. The central server may then send a command to the game to display a message, which the game then displays. The player may see the message on the screen and presses his PDK's button causing it to transmit this event over the secure link to the RDC. The RDC relays this information back to the server. When the central Server receives the button press message, it can enable the game so that the player may begin playing.

Figure 40:
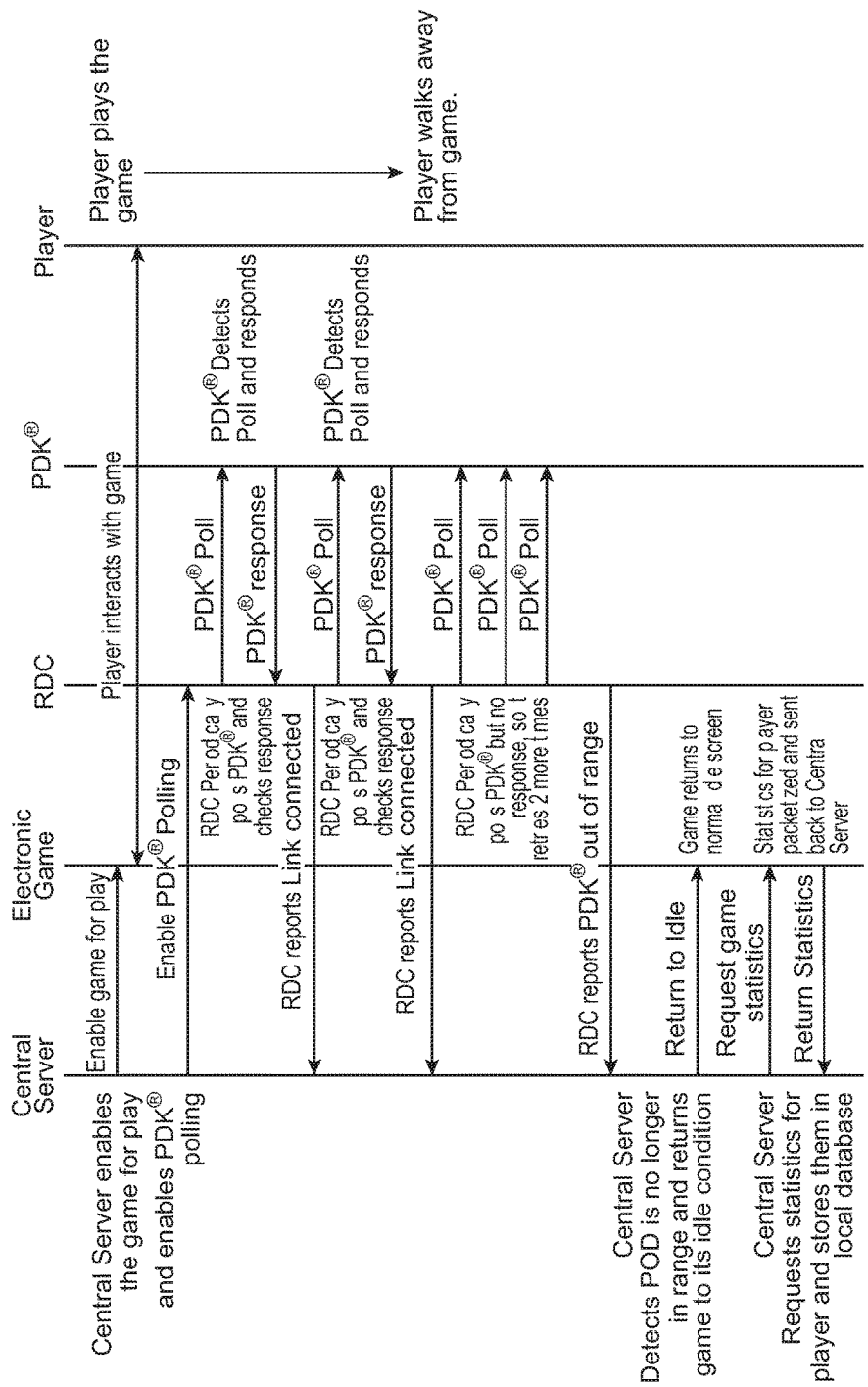
FIG. 40 shows an electronic game player association handshake in accordance with one or more embodiments of the present invention.

The handshake continues as shown in FIG. 40. After the game has been enabled for the player to play, the server may then send a command to the RDC to start polling the player's PDK. The RDC then periodically polls the PDK and may have returned the responses of each poll back to the server, as shown in FIG. 40.

Still referring to the example being described with reference to FIGS. 39 and 40, the player may continue to play the game for a while, then finishes and decides to leave. When the player exits the coverage area of the RDC near the game, the communications link is broken. The RDC attempts to poll the PDK, but receives no response. The RDC continues a few more times with no response. The RDC then reports back to the central server that the link was lost and the PDK is out of range. The central server then sends a message to the game to return it to an idle state so that another player can play, then requests the game to send back the player's game play information (if not already obtained), which the server logs.

As described above with reference to FIGS. 39 and 40, a central server may be the communications medium linking an RDC to a game. It communicates with the game, tying the PDK to that game. If either device loses connection to the central server, game play may stay enabled.

Figure 41:
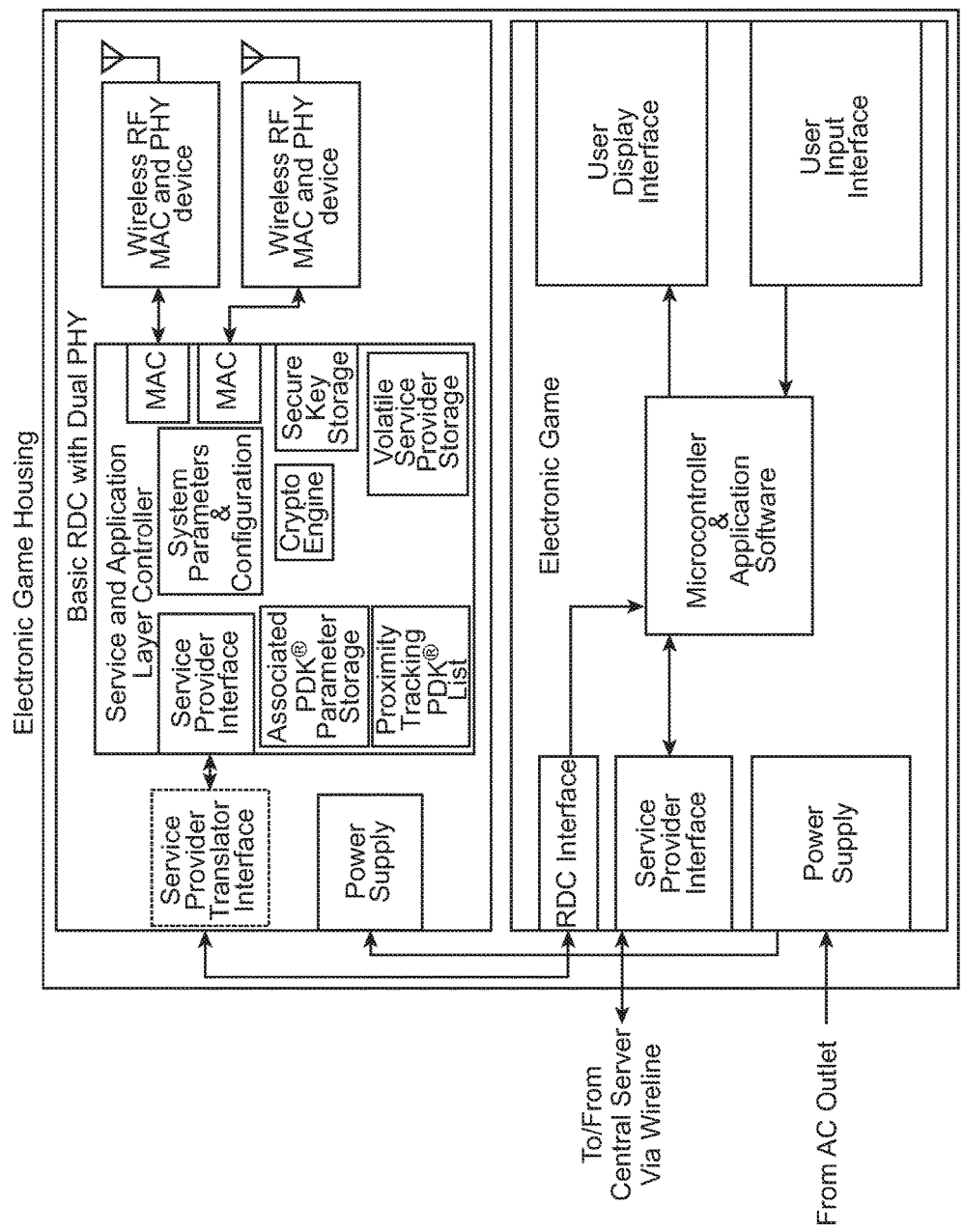
FIG. 41 shows a configuration of an electronic game with an integrated RDC in accordance with one or more embodiments of the present invention.

Now referring to FIG. 41, it shows an electronic game with an integrated RDC, internally connected to communicate directly with the game. Thus, all power and communication for the RDC may go through the electronic game. In this configuration, both the RDC and game reside within the same game enclosure where they jointly coexist. All information exchanged between the RDC and Bally Central Server must flow through the electronic game's controller and network interface. The purpose of placing them in the same enclosure allows the RDC to perform proximity detection for any player carrying a PDK® that may be positioned near the front of the machine.

Figure 38:
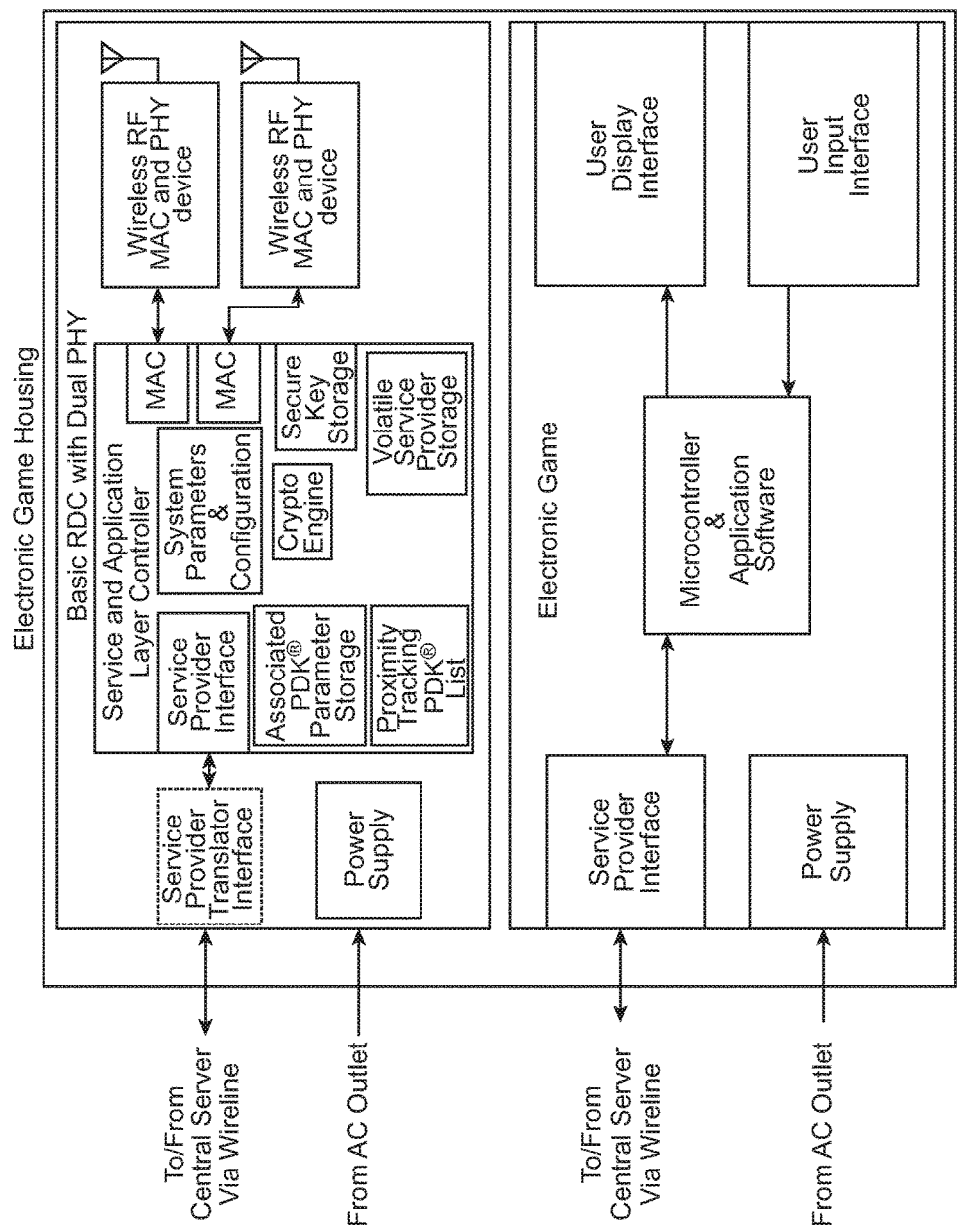
FIG. 38 shows a configuration of an electronic game with an integrated RDC in accordance with one or more embodiments of the present invention.
Figure 42:
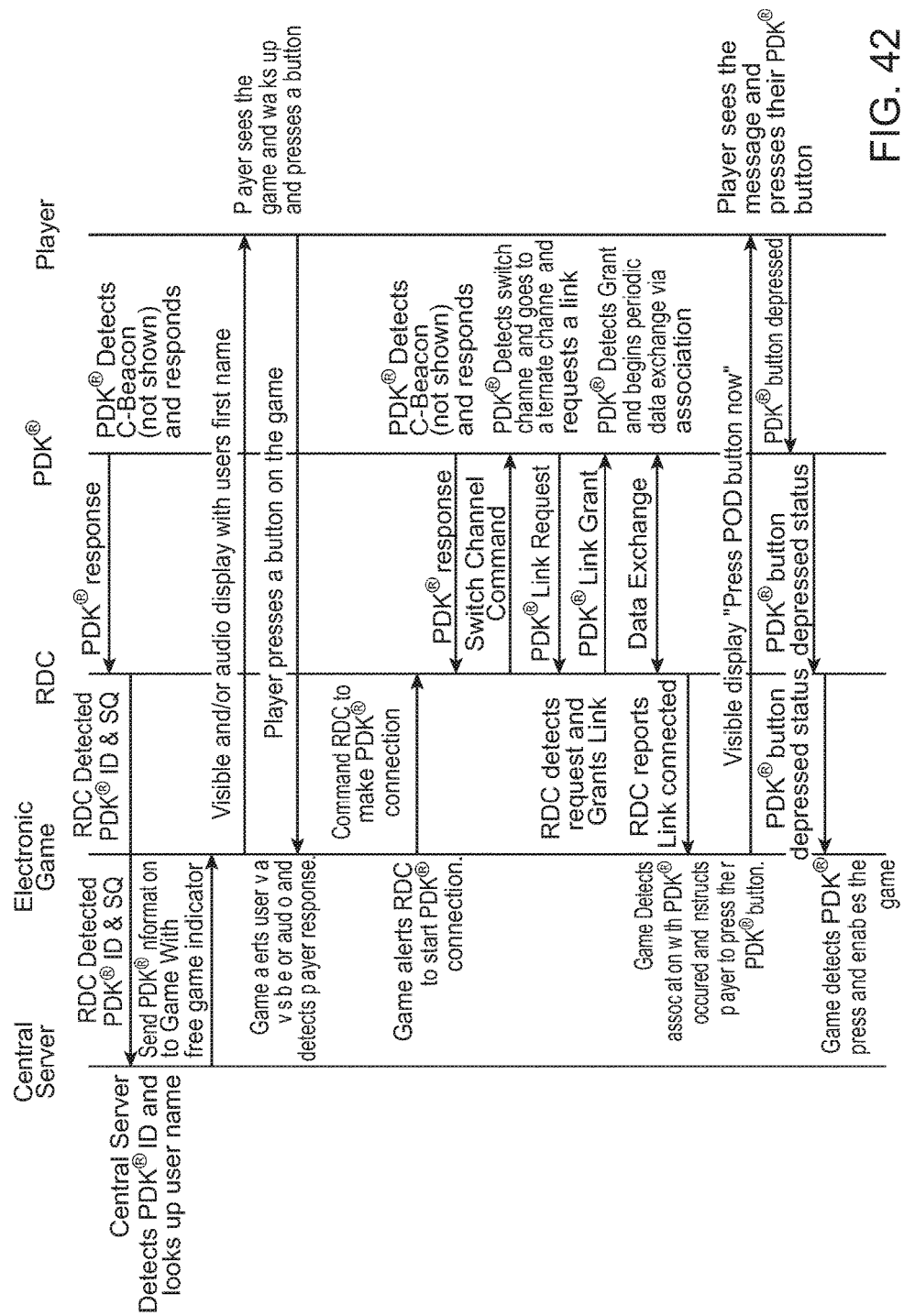
FIG. 42 shows an electronic game player tracking and game enable handshake in accordance with one or more embodiments of the present invention.

At least one difference in the configuration shown in FIG. 41 relative to the configuration shown in FIG. 38 is that the game's internal controller may act to reduce the traffic loading on the back-end network and perform more local verification of the communications link between the PDK and the RDC. To illustrate a difference in interaction between these two configurations, reference is made to the handshake diagram shown in FIG. 42. More particularly, FIG. 42 shows a handshake that may take place from the time a player carrying a PDK is detected to the time the game is enabled for that player. For purposes of clarity, the CRDC is not shown in FIG. 42. The handshake starts by the PDK detecting a c-beacon. Each time the c-beacon is detected on the expected superframe and timeslot, the PDK sends out a PDK location tracking response. The RDC within the game detects the response and sends the PDK information back to a central server via the game's internal controller. The server is made aware that the user is close to the game and sends a command back to the game controller instructing the game to, for example, give the user a free game along with optionally displaying the user's name. The game then displays a message for the player in an effort to entice the player to play. The player may then see the message, sit down at the game, and press a button to commence game play. In turn, the game controller detects the button press and requests the RDC to make a connection with the player's PDK. Upon the next c-beacon, the PDK responds and the RDC receives the response. The RDC may then transmit back to the PDK a command to change to an alternate channel for association. The player's PDK then switches to the alternate channel indicated by the RDC and sends out a PDK link request with both the PDK ID and the RDC ID. The RDC detects the request and sends back a PDK link grant. The PDK and the RDC may then exchange secure information to establish trust, prior to establishing a secure link for validation of the PDK. The RDC may also lower its RF power and instruct the PDK to lower its RF power in order to enforce close proximity Periodic data exchange may then continue between the RDC and PDK.

After the secure link is established, the RDC reports back to the game controller that the link is established between the RDC and PDK. The game may then display an instructional message for game play. The player may see the message on the screen and presses the player's PDK button, causing the PDK to transmit this event over the secure link to the RDC. The RDC may then send this information back to the game controller. When the game controller receives the button press message, it can enable the game so that the player can begin playing.

Figure 43:
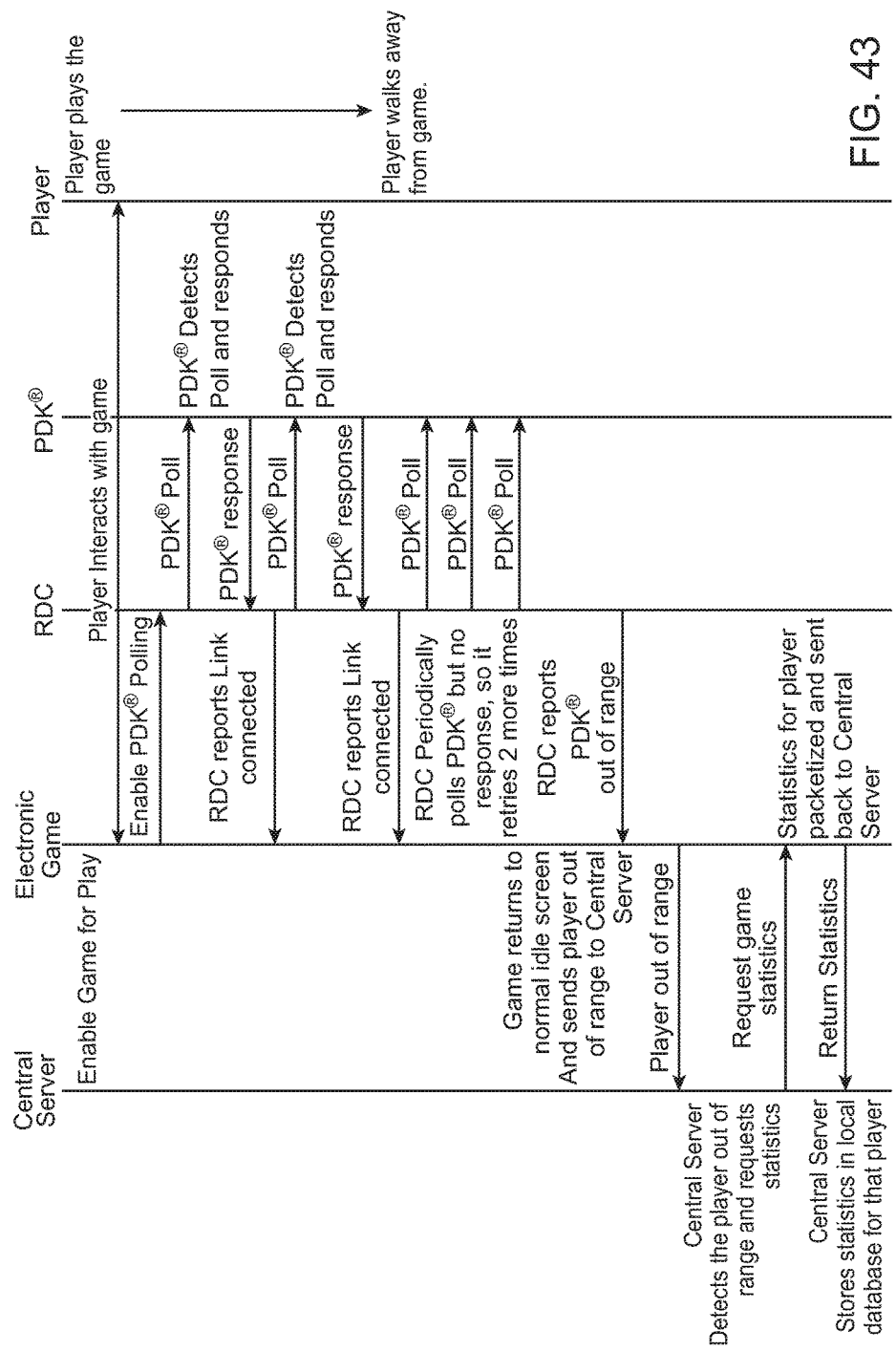
FIG. 43 shows an electronic game player association handshake in accordance with one or more embodiments of the present invention.

The handshake continues as shown in FIG. 43. After the game was enabled for the player to play, the game controller sends a command to the RDC to start polling the player's PDK. The RDC then periodically polled his PDK and had the option of returning the responses of each poll back to the controller, as shown in FIG. 43.

Returning to the example described above with reference to FIGS. 42 and 43, the player may continue to play the game for a while, then finishes and decides to leave. When the player exits the coverage area of the RDC near the game, the communications link is broken. The RDC attempts to poll the PDK, but receives no response. The RDC may continue a few more times, with no response. The RDC then reports back to the game controller that the link was lost and the PDK is out of range. The game controller returns itself to an idle state so that another player can play and indicates back to the central server that the PDK is out of range. The server may then request the game to send the player's game play information (if not already received), which is then logged.

As described above with reference to FIGS. 42 and 43, in one or more embodiments, the game controller may become more involved in the RDC to PDK association, thereby potentially reducing the back-end system network's traffic loading relative to that experienced with the configuration where an RDC is electrically separate from the game controller. The game controller may also react faster to the user walking out of range and may not require any response from the server in order to maintain the link. It is further noted that a broken link between the central server, game controller, and RDC may not result in any loss of any interaction between the RDC and the game controller.

Device Configuration and Installation

Figure 44:
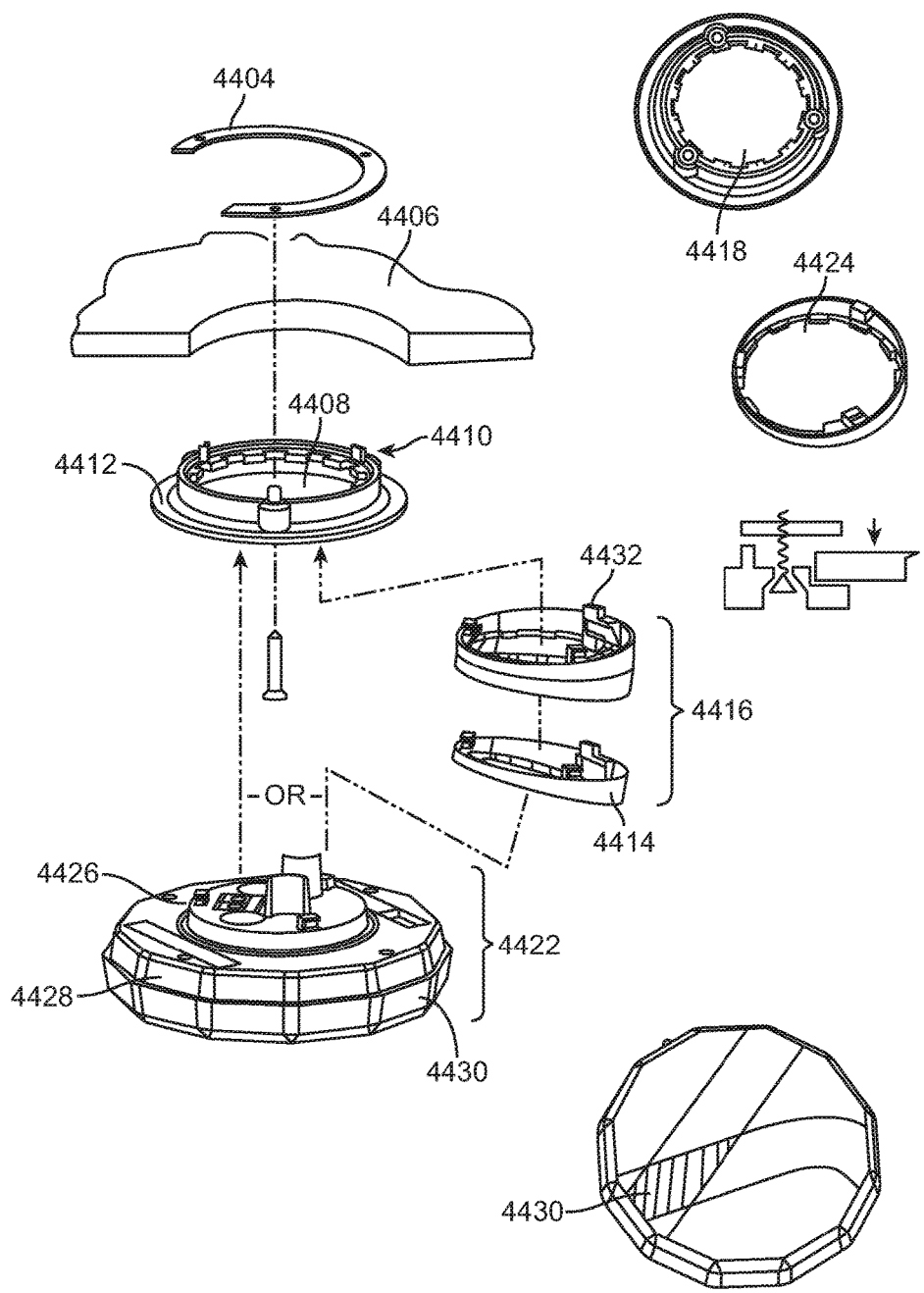
FIG. 44 shows the mounting of a housing in accordance with one or more embodiments of the present invention.

Now referring to FIG. 44, the mounting of a housing in accordance with one or more embodiments of the present invention is illustrated. In one embodiment, the housing 4422 comprises a housing back 4428 and a housing front 4430 which are joined together to enclose electrical components such as electrical components comprising a RDC or a CRDC. For example, the antenna and circuitry that comprise a CRDC or a RDC are enclosed within the housing 4422. In some embodiments, the housing front 4430 and housing back 4428 are joined without the use of one or more of a tool and separate fasteners. For example, the housing front 4430 and housing back 4428 are threaded together, joined by an interference fit, or joined using one or more clips. In one embodiment, the housing 4422 is predominantly circular as illustrated. In one embodiment, the housing 4422 is predominantly circular because it houses one or more antennae that are circular. As illustrated, the housing 4422 can be mounted on building material 4406 during installation. Examples building material include but are not limited to wood, plywood, gypsum, fiberboard, fiberglass, ceiling tiles, etc. and may be a component of wall, ceiling, floor, beam, etc.

In the illustrated embodiment, a bracket comprising a bracket back 4404 and a bracket face plate 4412 is used to attach a housing 4422, 4423 to building material 4406 during installation. As illustrated, a bracket back 4404 is placed on the back side of a cut-out in the building material 4406 and the bracket face plate 4412 is placed on the opposite side of the cut-out. The bracket back 4404 and the bracket face plate 4412 are then interconnected, for example, using one or more fasteners such as a screw, so that the building material is "sandwiched" between the two bracket pieces 4404, 4412. In one embodiment, the fasteners are used at equidistant points and each fastener is directed through its own aperture. In some embodiments, one or more of the bracket back 4404 and the bracket face plate 4412 include structure such as a set of posts 4410, which limit the minimum space between the bracket back 4404 and the bracket face plate 4412, for example, in order to minimize the risk of over tightening the two pieces when fastening and cracking the building material 4406.

In one embodiment, once the bracket 4404, 4412 is attached to the building material 4406, the housing back 4422, specifically, the housing back 4426 may be attached directly to the bracket 4412 or can be attached to one or more aiming annuli 4414. In some embodiments, the housing back 4426 is attached to the bracket 4412 or an aiming annulus 4414 without the use of separate fasteners and without the use of any tools. For example, one or more of the housing 4422, bracket face plate 4412 and aiming annulus 4414 are a molded plastic part including one or more of a clip, tab, tooth, groove, slot, etc. which can attach one component to the other without the use of a tool or separate fastener.

In one embodiment, the housing back 4426 has a plurality of structures 4426 protruding perpendicular from the back of the housing back 4426. In one such embodiment, each structure 4426 is shaped approximately like an upside-down capital "L" attached to the back of the housing back 4426. In one such embodiment, the plurality of structures 4426 are capable of interface with a plurality "teeth" 4418, 4424 on one or more of the bracket face plate 4412 and an aiming annulus 4414, respectively, in order to attach the housing back 4426 to the other component 4412, 4414.

As illustrated, the aiming annulus 4414 includes an annular extrusion wherein the two annular faces of the annular extrusion are non-parallel giving the aiming annulus 4414 a wedge-like shape when viewed in profile. In other words the aiming annulus 4414 has a shape similar to a short piece of pipe with the ends cut non-parallel to one another. It will be recognized that, while the aiming annulus 4414 is described as an annular extrusion, the aiming annulus 4414 is not necessarily created using an extrusion process. The aiming annulus 4414 may be created, for example, using injection molding.

The annular shape of the aiming annulus 4414 allows any wiring for power and/or signal to the housing 4408 to be enclosed. The wedge-like shape of the aiming annulus 4414 beneficially allows the housing 4422 to be mounted at an angle non-parallel with the surface the bracket 4404, 4412 attached to, i.e., the aiming annulus 4414 enables a housing 4422 and its enclosed components to be aimed. Aiming the housing 4422 is beneficial, for example, it enables an installer to optimize the coverage of the RDC or CRDC enclosed in the housing 4422.

In some embodiments, the aiming of the housing 4422 is determined at least in part by one or more of the angle of the two annular faces of an aiming annulus 4414 and the number of aiming annuli used. For example, multiple aiming annuli 4414 having varying angles between the planes of the two annular faces (not shown) may be manufactured and made available to an installer allowing the installer to select and attach the aiming annulus 4414 with the desired angle. For another example, the aiming annuli 4414 have a uniform angle between the two annular faces and an installer attaches multiple aiming annuli 4416 in order to achieve the desired angle.

In some embodiments, the aiming of the housing 4422 is determined at least in part by the rotational positioning of one or more of the bracket 4404, 4412, the housing 4422 and one or more aiming annuli 4414 relative to each other. For example, in the illustrated embodiment, the bracket face plate 4412 is shown having a plurality of tooth-like structures 4418 on its inner ring. The aiming annulus 4414 is shown having a plurality of similar tooth-like structures 4424 on the interior of the annular extrusion and structures 4432 capable of attaching the aiming annulus 4414 to another aiming annulus 4414 or to the bracket face plate 4412. In some embodiments, the tooth-like structures 4418, 4424 of the bracket face plate 4412 and an aiming annulus 4414 have compatible dimensions. In one embodiment, the structures 4432 comprise structural components with the compatible dimensions as the structures 4426 on the housing back 4426.

In some embodiments, one or more of the structures 4426, 4432 and tooth-like structures 4418, 4424 serve to limit the relative rotational motion of one component to another, for example, structures 4432 of the aiming annulus 4414 fit between the "teeth" 4418 of bracket face plate 4418 such that the components 4412, 4414 cannot rotate relative to each other. In some embodiments, one or more of the structures 4426, 4432 and tooth-like structures 4418, 4424 serve two purposes, for example, to attach one component to another and to limit rotational motion of one component to another. For example, in one embodiment, the structures 4426 of the housing back 4426 are inserted between the gaps of the tooth-like structures 4424 of the aiming annulus 4414 and a twist of the housing back 4426 relative to the aiming annulus 4414 causes the structures 4426 to interlock with the tooth-like structures 4424. Such an embodiment, may, therefore, attach the housing back 4426 to an aiming annulus 4414 without the use of a tool or separate fastener and for further rotational motion of the two components to be limited. If a modification of the aiming is desired, a reverse twist will cause the structures 4426 to release the tooth-like structures 4424 at which point the structures 4426 can be aligned with different gaps between the tooth-like structures 4424 and twisted into a new rotational position. In one embodiment, the reverse twist used to unlock two components requires torque that exceeds the torque normally exerted by the components themselves on the interconnection in order to ensure that the components do not separate in the mounted position due to their own mass. Limiting rotation of one or more of the components 4412, 4414 and 4426 relative to each other beneficially maintains the aiming of the housing 4422.

Figure 45:
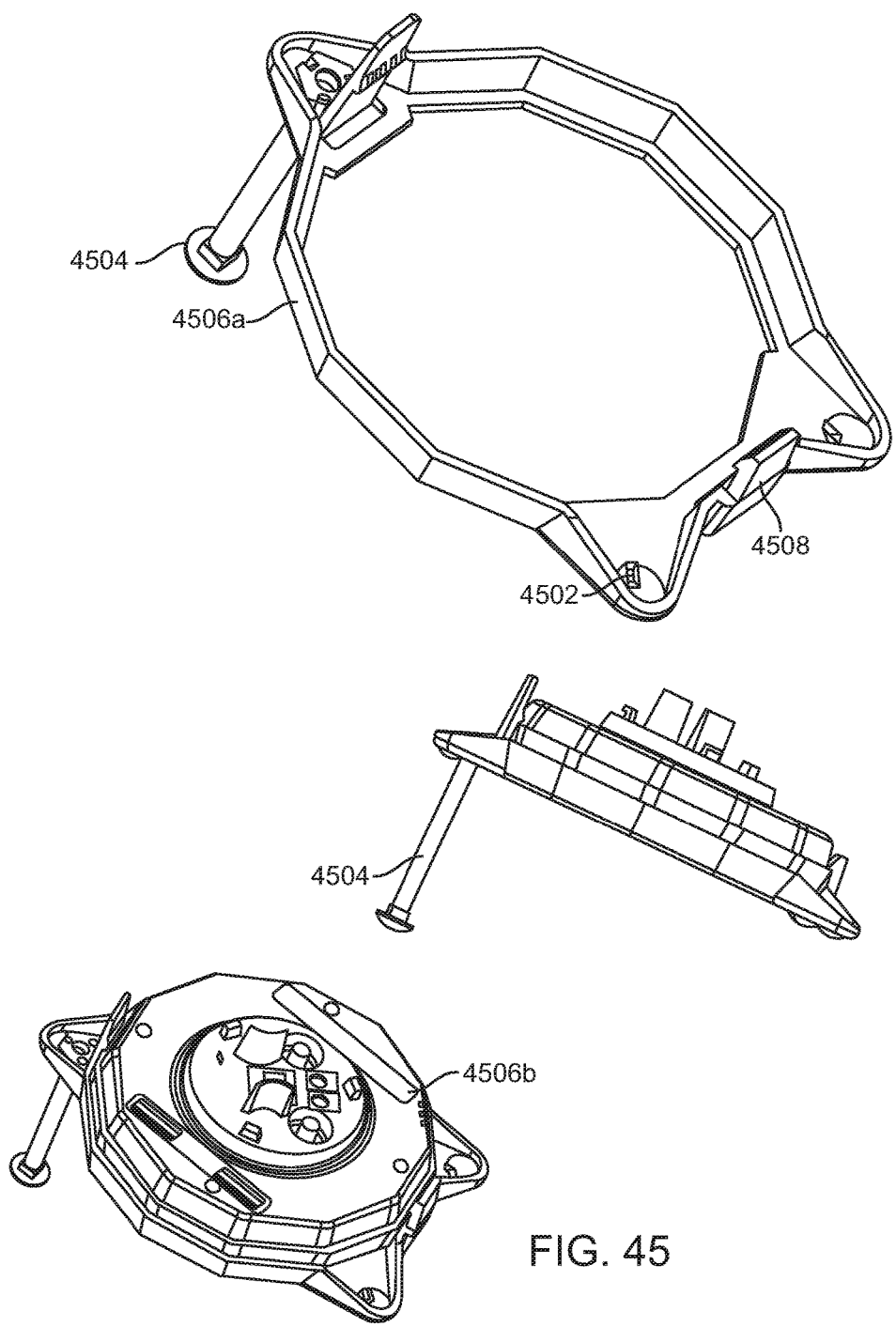
FIG. 45 shows the mounting of a housing in accordance with one or more embodiments of the present invention.

Now referring to FIG. 45, another mounting of a housing in accordance with one or more embodiments of the present invention is illustrated. It may at times be desirable to mount a housing behind building material, e.g., when creating a cut-out in building material is unnecessary. Housing front 4506a enables such mounting to occur. In the illustrated embodiment, housing front 4506a includes clips 4508, apertures 4502 and a carriage bolt 4504. In the illustrated embodiment, the clips 4508 allow the housing front 4506*a* to attach to a housing back 4506*b*. In one embodiment, the housing back 4506*b* is the same as the housing back 4426 of FIG. 44. The apertures 4502 allow the housing face to be fastened, e.g., by screw or nail, to building material. The carriage bolt 4504 is threaded in one embodiment. The carriage bolt's 4504 effective length, when adjusted, adjusts the angle of the housing front 4506 relative to the building material on which housing front 4506*a* is mounted allowing the housing and its enclosed components (e.g., a RDC or CRDC) to be aimed.

Figure 46:
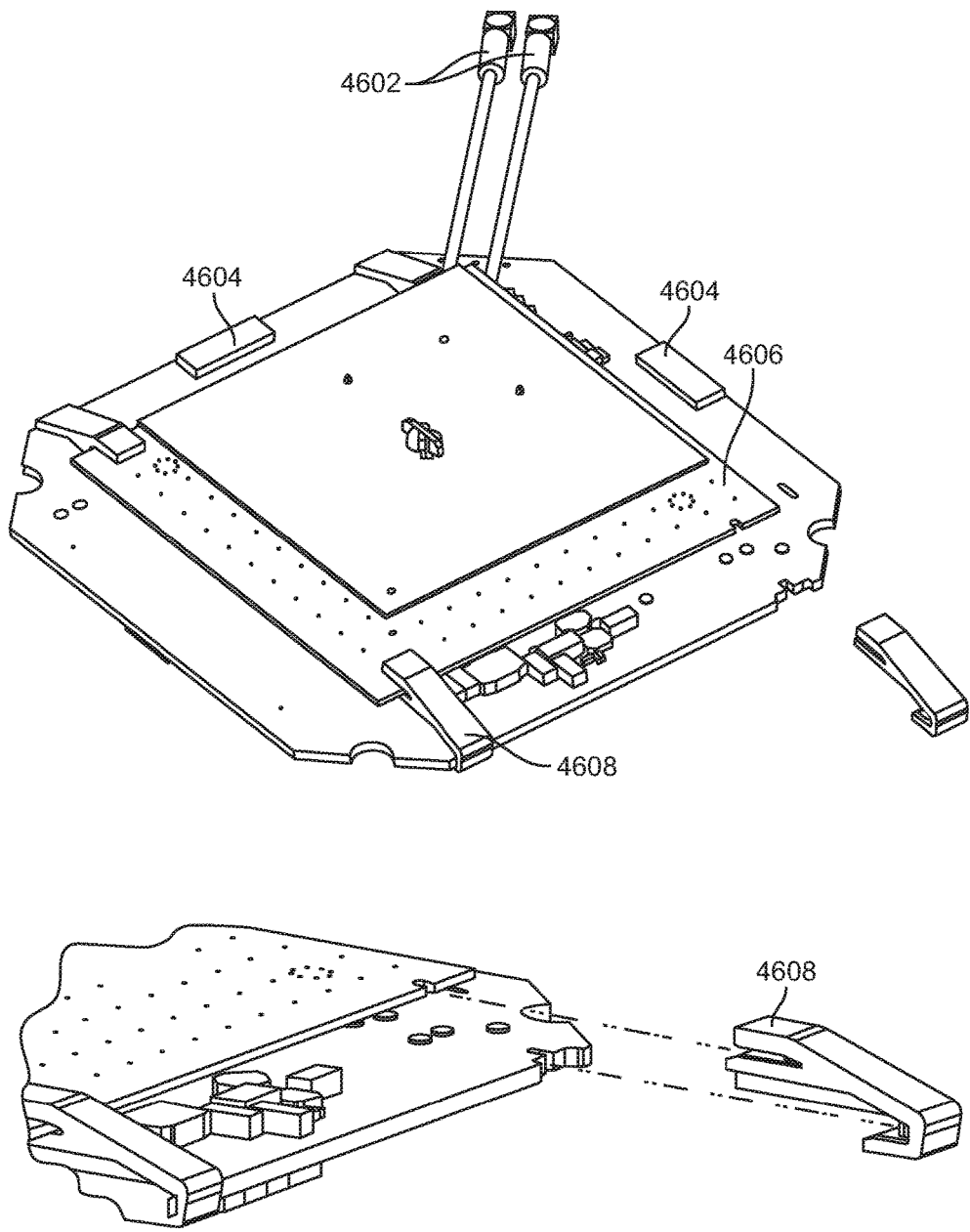
FIG. 46 shows the configuration of electronics within a housing in accordance with one or more embodiments of the present invention.

Now referring to FIG. 46, a configuration of the electronics that may be enclosed within a housing in accordance with one or more embodiments of the present invention is illustrated. For example, the electronics comprising a CRDC or a RDC are illustrated. In one embodiment, one or more of the RDC and CRDC comprises two antennas 4604 oriented such that they are not parallel to each other. In one such embodiment, the two antenna 4604 are oriented such that they are orthogonal to one another. The orthogonal orientation of the two antennas beneficially ensures that a signal between one or more of a RDC, a CRDC and a PDK will not be lost due to the orientation of one device relative to another. For example, when a PDK and a RDC each have a single antenna it is possible to position the PDK in an orientation that severs the signal between the PDK and RDC even if the PDK is well within the range of the RDC. The inclusion of a second and orthogonal antenna in the RDC may preclude such a scenario from occurring. Moreover, inclusion of two orthogonal antennas allows for additional signal quality metrics. For example, assume almost no signal from a PDK is being picked up on the first antenna and a strong signal is being picked up from the PDK by the second antenna, in one embodiment, those signal quality metrics are used to determine the orientation of a PDK.

In one embodiment, the electronics comprise two antenna jacks 4602. The antenna jacks 4602 allow for the attachment of antenna. For example, assume the integrated antenna pair 4604 is omnidirectional. In some circumstances it will be desirable for the antenna to be direction (e.g., only detect a PDK when the PDK is in front), the antenna jacks allow for directional antenna to be easily attached to the rest of the existing electronics.

In some embodiments, an external antenna plugged into an antenna jack 4602 overrides an integrated antenna 4604. In one such embodiment, the external antenna makes use of the same firmware used for the integrated antenna 4604. The addition of the antenna jacks 4602 and ability for external antennae to override the internal antennae beneficially allows for the system to be easily modified by adding different antenna without having to reconfigure other aspects of the device resulting in a large degree of flexibility without complicated or time-consuming modifications.

Reflector stand-off clips 4608 are also depicted. A reflector stand-off clip 4608 beneficially allows for the easy assembly of the various components comprising one or more of a RDC and a CRDC. Specifically, the reflector stand-off clip 4608 allows for the reflector 4606 to be mounted at the proper location in relationship to one or more of the antennae 4604 and the also to allow for the reflector to be mounted above the underlying electronics without coming into contact with those electronics.

Figure 47:
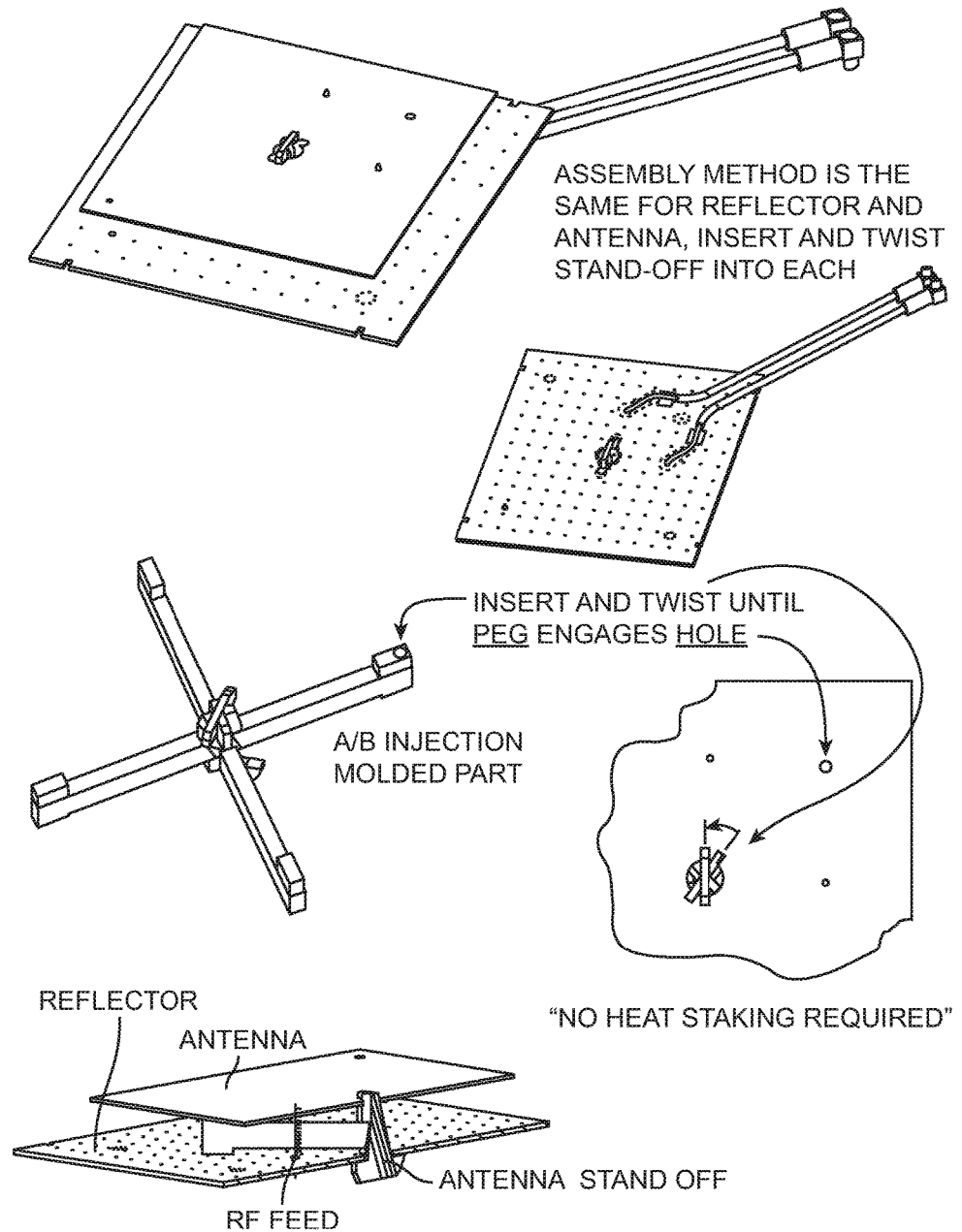
FIG. 47 shows the configuration of electronics within a housing in accordance with one or more embodiments of the present invention.

Now referring to FIG. 47, further details regarding the configuration of electronics that may be enclosed in a housing in accordance with one or more embodiments of the present invention are illustrated.

Figure 48:
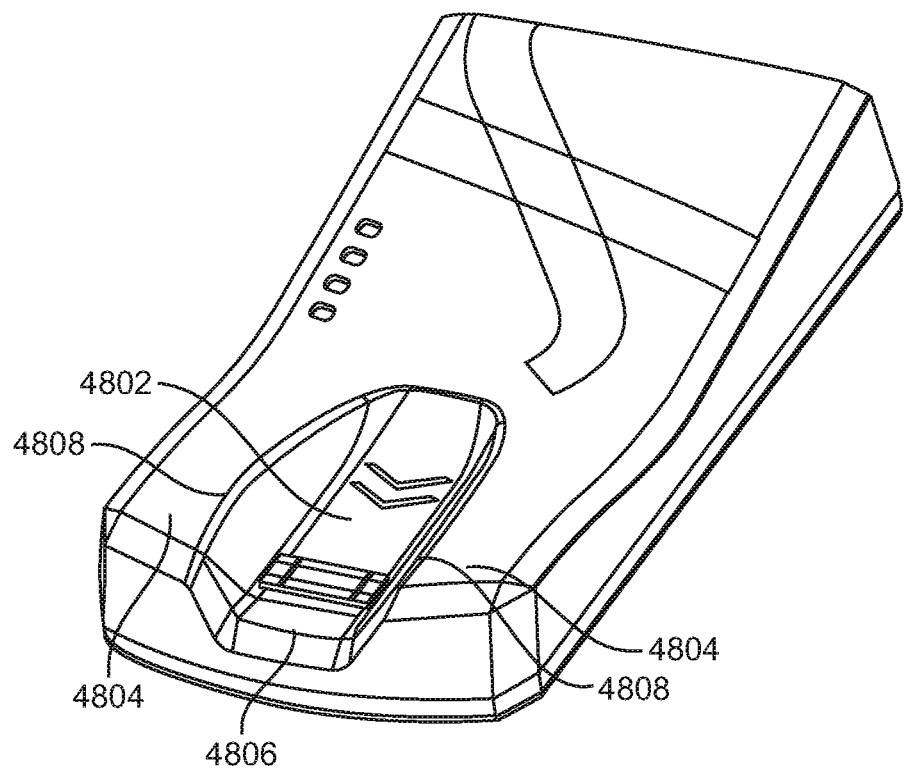
FIG. 48 shows a biosensor in accordance with one or more embodiments of the present invention.

Now referring to FIG. 48, a biosensor in accordance with one or more embodiments of the present invention. In the illustrated embodiment, the biosensor is a fingerprint reader. A user drags his/her finger down the groove 4802 toward the front edge 4806 allowing the biosensor to read the user's fingerprint. In one embodiment, the front edge 4806 is chamfered as illustrated to prevent the user's finger from contacting the housing and tipping the device during a finger swipe. In one embodiment, the groove 4802 separates two antenna housed within the biosensor in addition to guiding a user's finger during a finger swipe. In one embodiment, the two antennae are oriented orthogonally to each other. In one embodiment, the two antenna are located on opposite sides of and physically separated by the groove 4802, and the groove creates a radome 4804 for each antenna. The creation of the radomes 4804 and physical separation of the antennae by the groove enhance the performance of the antennae.

In some embodiments, the surface of the groove 4802 on which the user's finger runs along has a width that measures 0.5 inches and a length of 1.875 inches. In such embodiments, the measurement of the space between each randome edge 4808 is 0.875 inches. In such embodiments, these measurements and shapes described above creates a preferred structure that allows accurate finger reading for users having various finger sizes.

Figure 49:
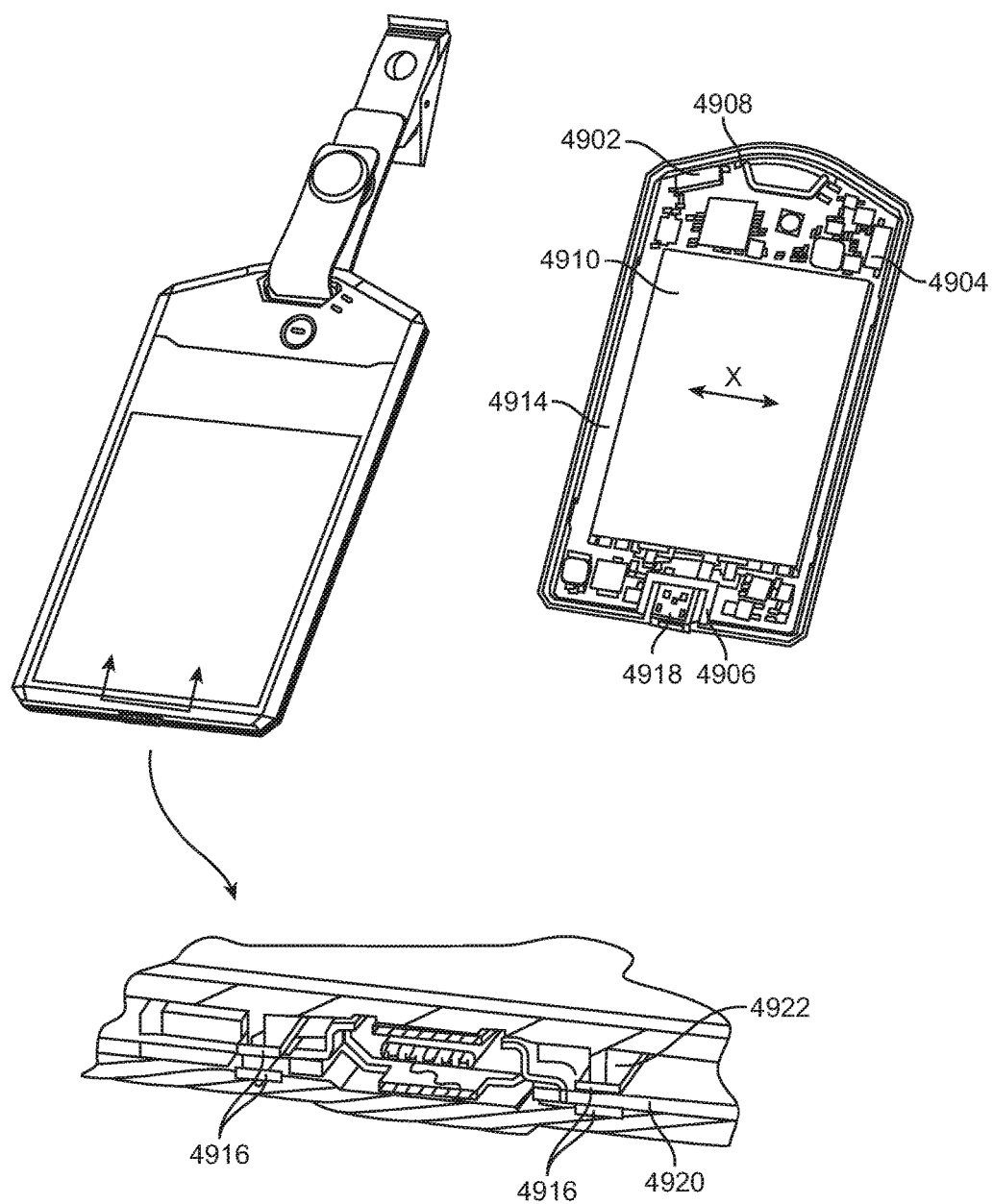
FIG. 49 shows a PDK in accordance with one or more embodiments of the present invention.

Now referring to FIG. 49, a PDK in accordance with one or more embodiments of the present invention is illustrated. In one embodiment, the PDK comprises two antennas 4902 and 4904 oriented such that they are not parallel to each other. In one such embodiment, the two antennas 4902 and 4904 are oriented such that they are orthogonal to one another. The orthogonal orientation of the two antennae 4902 and 4904 beneficially ensures that a signal between a RDC and a PDK will not be lost due to the orientation of one device relative to the other. For example, when a PDK and a RDC each have a single antenna it is possible to position the PDK in an orientation that severs the signal between the PDK and RDC even if the PDK is well within the range of the RDC. The inclusion of a second and orthogonal antenna in the PDK may preclude such a scenario from occurring.

In the illustrated embodiment, the PDK further comprises a battery 4910 which fits into a cut-out 4914 in a printed circuit board ("PCB"), a USB or other port 4918 and a conductor 4908 such as wire or sheet metal to bridge the PCB ground plane in order to optimize antenna performance In some embodiments, it is desirable for the PDK to be waterproof. For example, the PDK may be a badge worn by a healthcare provider in a hospital and therefore needs to be cleaned and sanitized regularly. In the illustrated embodiment, the PDK is housed in a plastic shell where the edges may be fused. However, fusing the perimeter of the plastic shell does not waterproof the port 4918. In one embodiment, the port 4918 is sealed using one or more horseshoe gaskets 4906. For example, in one embodiment, a horseshoe gasket 4906 is placed on each side of the PCB surrounding the port 4918 between the PCB and the outer plastic shell. In one such embodiment, the plastic shell has one or more ridges that align with the gasket. The ridges are compressed into the gasket and the perimeter of the shell is fused creating a waterproof seal that isolates the internal components of the PDK from the port 4918 and the rest of the external environment. The cross section illustrated in FIG. 49 shows the two horseshoe gaskets 4916 that isolate the port located on both sides of the PCB 4920 and compressed by a ridge 4922 in the shell to create a waterproof seal.

While the invention has been described with respect to a limited number of embodiments, those skilled in the art, having benefit of the above description, will appreciate that other embodiments may be devised which do not depart from the scope of the present invention as described herein. Accordingly, the scope of the present invention should belimited only by the appended claims.

What is claimed is:

1. A system comprising a biometric reader device, the biometric reader device comprising:
   two antennae oriented orthogonal to each other;
   a biosensor located between the two orthogonal antennae and capable of performing a biometric reading of a user's finger; and
   a housing comprising a groove that guides the user's finger to the biosensor, the groove physically separating the two orthogonal antennae and effectively creating a radome for each of the two orthogonal antennae.

2. The system of claim 1, wherein the housing further comprises a chamfered front edge at an end of the groove, wherein the chamfered front edge prevents the user's finger from tipping the biometric reader device during a finger swipe.

3. The system of claim 1, wherein the two orthogonal antennae are the only antennae in the biometric reader device.

4. The system of claim 1, wherein the biometric reader device is configured to communicate securely with one of a reader decoder circuit or a personal digital key.

5. The system of claim 1, wherein a secure communication between the biometric reader device and one of a reader decoder circuit or a personal digital key comprises an authentication of a biometric reading.

6. The system of claim 1, further comprising a reader decoder circuit that authorizes communication between the biometric reader device and one of a reader decoder circuit or a personal digital key.

7. The system of claim 1, wherein each of the two radomes has a radome edge, the distance between the two radome edges is approximately 0.875 inches.

8. The system of claim 1, wherein the bottom of the groove is approximately 0.5 inches in width.

9. The system of claim 1, wherein the bottom of the groove is approximately 1.875 inches in length.

10. The system of claim 1, wherein the biosensor is located at the bottom of the groove, the groove narrowing in at least one dimension to guide the user's finger toward the biosensor.

11. A method for performing a biometric reading of a user's finger on a wireless device, the method comprising:
    receiving, in a groove of a device housing, the user's finger, wherein the groove physically separates two orthogonal antennae and effectively creates a radome for each of the two orthogonal antennae;
    guiding, within the groove, the user's finger to a biosensor located between the two orthogonal antennae, the biosensor capable of performing a biometric reading of the user's finger; and
    reading the user's finger with the biosensor.

12. The method of claim 11, wherein the device housing further comprises a chamfered front edge at an end of the groove, wherein the chamfered front edge prevents the user's finger from tipping the device housing during a finger swipe.

13. The method of claim 11, wherein the two orthogonal antennae are the only antennae in the device.

14. The method of claim 11, wherein the wireless device is configured to communicate securely with one of a reader decoder circuit or a personal digital key.

15. The method of claim 11, wherein a secure communication between the wireless device and one of a reader decoder circuit or a personal digital key comprises an authentication of a biometric reading.

16. The method of claim 11, further comprising a reader decoder circuit that authorizes communication between the wireless device and one of a reader decoder circuit or a personal digital key.

17. The method of claim 11, wherein each of the two radomes has a radome edge, the distance between the two radome edges is approximately 0.875 inches.

18. The method of claim 11, wherein the bottom of the groove is approximately 0.5 inches in width.

19. The method of claim 11, wherein the bottom of the groove is approximately 1.875 inches in length.

20. The method of claim 11, wherein the biosensor is located at the bottom of the groove, the groove narrowing in at least one dimension to guide the user's finger toward the biosensor.

* * * * *